(12) United States Patent
Bryhn et al.

(10) Patent No.: US 8,399,516 B2
(45) Date of Patent: Mar. 19, 2013

(54) ALPHA-SUBSTITUTED OMEGA-3 LIPIDS THAT ARE ACTIVATORS OR MODULATORS OF THE PEROXISOME PROLIFERATORS-ACTIVATED RECEPTOR (PPAR)

(75) Inventors: Morten Bryhn, Svelvik (NO); Anne Kristin Holmeide, Oslo (NO); Jenny Rosman, Marstrand (SE)

(73) Assignee: Pronova Biopharma Norge AS, Baerum (NO)

( * ) Notice: Subject to any disclaimer, the term of this patent is extended or adjusted under 35 U.S.C. 154(b) by 518 days.

(21) Appl. No.: 12/446,615

(22) PCT Filed: Nov. 1, 2007

(86) PCT No.: PCT/IB2007/003305
§ 371 (c)(1),
(2), (4) Date: May 19, 2009

(87) PCT Pub. No.: WO2008/053331
PCT Pub. Date: May 8, 2008

(65) Prior Publication Data
US 2010/0035990 A1    Feb. 11, 2010

Related U.S. Application Data

(60) Provisional application No. 60/855,733, filed on Nov. 1, 2006.

(30) Foreign Application Priority Data

Nov. 1, 2006 (SE) ........................................ 0602310

(51) Int. Cl.
*A01N 37/00* (2006.01)
(52) U.S. Cl. ........................... 514/560; 554/80; 554/224
(58) Field of Classification Search .................. 514/560; 554/80, 224
See application file for complete search history.

(56) References Cited

U.S. PATENT DOCUMENTS

| | | | |
|---|---|---|---|
| 2,836,628 | A | 5/1958 | Miller |
| 4,132,719 | A | 1/1979 | Mohrbacher et al. |
| 4,264,517 | A | 4/1981 | Liang |
| 4,647,685 | A | 3/1987 | Bonjouklian et al. |
| 5,422,371 | A | 6/1995 | Liao et al. |
| 5,502,077 | A | 3/1996 | Breivik et al. |
| 5,656,667 | A | 8/1997 | Breivik et al. |
| 5,698,594 | A | 12/1997 | Breivik et al. |
| 6,365,628 | B1 | 4/2002 | Berge |
| 6,689,812 | B2 | 2/2004 | Peet et al. |
| 7,550,613 | B2 | 6/2009 | Bryhn et al. |
| 8,034,845 | B2 | 10/2011 | Bryhn et al. |
| 2004/0162348 | A1 | 8/2004 | Peet et al. |
| 2006/0135610 | A1 | 6/2006 | Bortz et al. |

FOREIGN PATENT DOCUMENTS

| | | |
|---|---|---|
| EP | 1 300 470 A1 | 4/2003 |
| EP | 1 310 249 A1 | 5/2003 |
| EP | 1 426 047 A1 | 6/2004 |
| EP | 1 466 597 A1 | 10/2004 |
| EP | 1 544 281 A1 | 6/2005 |
| EP | 1544281 A1 * | 6/2005 |
| JP | 57-149400 | 9/1982 |
| JP | 59-204175 | 11/1984 |
| JP | 63-88159 | 4/1988 |
| JP | 05-000974 | 1/1993 |
| JP | 06-240289 | 8/1994 |
| JP | 6-293789 | 10/1994 |
| JP | 7-53488 | 2/1995 |
| JP | 10-195023 | 7/1998 |
| JP | 2002-180082 | 6/2002 |
| JP | 2004-182674 | 7/2004 |
| JP | 2003-283858 | 2/2005 |
| WO | WO 97/44063 | 11/1997 |
| WO | WO 99/26620 | 6/1999 |
| WO | WO 99/26661 | 6/1999 |
| WO | WO 02/052955 A1 | 7/2002 |
| WO | WO 03/092673 A1 | 11/2003 |
| WO | WO 2004/012727 A1 | 2/2004 |
| WO | WO 2004/043894 A1 | 5/2004 |
| WO | WO 2004/071504 A1 | 8/2004 |
| WO | WO 2004/078166 A2 | 9/2004 |

(Continued)

OTHER PUBLICATIONS

Larsen, Laila N. et al., Biochemical Pharmacology (1998), 55(4), 405-411.*

(Continued)

*Primary Examiner* — Deborah D Carr
(74) *Attorney, Agent, or Firm* — Finnegan, Henderson, Farabow, Garrett & Dunner, LLP

(57) ABSTRACT

Omega-3 lipid compounds of the general formula (I):

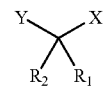

wherein $R_1$ and $R_2$ are the same or different and may be selected from a group of substituents consisting of hydrogen, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group; X represents a carboxylic acid or a derivative thereof, a carboxylate, a carboxylic anhydride or a carboxamide; and Y is a $C_6$ to $C_{22}$ alkene with two or more double bonds, having E and/or Z configuration, are disclosed. Also disclosed are pharmaceutical compositions and lipid compositions comprising such compounds, and to such compounds for use as medicaments in particular for the treatment of cardiovascular and metabolic diseases.

51 Claims, No Drawings

FOREIGN PATENT DOCUMENTS

| | | | |
|---|---|---|---|
| WO | WO 2004078166 A2 * | 9/2004 | |
| WO | WO 2004/085582 A2 | 10/2004 | |
| WO | WO 2005/060954 A1 | 7/2005 | |
| WO | WO 2005060954 | * | 7/2005 |
| WO | WO 2006/117664 A1 | 11/2006 | |
| WO | WO 2006/117668 A1 | 11/2006 | |
| WO | WO 2007/107869 A2 | 9/2007 | |
| WO | WO 2007/116027 A1 | 10/2007 | |
| WO | WO 2010/006085 A1 | 1/2010 | |

OTHER PUBLICATIONS

Vaagenes, Hege et al., Lipids (1998), 33(11), 1131-1137.*
Kato, Tadahiro et al., Biochemistry, (2003), 42(32), 9779-9788.*
Larsen, Laila N. et al., Lipids, (2005), 40(1), 49-57.*
Chem. Abstract, 1996:483717; Synthesis of C2- elongated polyunsaturated fatty acids.*
Berger, A. et al., "Structural Requirements of Sphingosylphosphocholine and Sphingosine-l-phosphate for Stimulation of Activator Protein-1 Activity," *Molecular Pharmacol.* (1996) 50:451-457.
Bonjouklian, R. et al., "Studies of the Antitumor Activity of (2-Alkoxyalkyl)- and (2-Alkoxyalkenyl)phosphocholines," *J. Med. Chem.* (1986) 29:2472-2477.
CAPlus Abstract for Kaufmann, H. P. and Kirschnek, A., "Fatty aldehydes. IV. Preparation of fatty aldehydes containing more than one double bond," *Fette, Seifen, Anstrichmittel* (1958) 60:1125-1132.
CAPlus Abstract, AN 1996:483717, for Kuklev, D. V., et al., "Synthesis of C2-elongated polyunsaturated fatty acids," *Bioorganischeskaya Khimiya* (1996) 22(3):219-222.
Cateni, F. et al., "Total Synthesis of a Natural Cerebroside from Euphorbiaceae," *Helv. Chim. Acta* (2007) 90:282-290.
Copending U.S. Appl. No. 12/447,092, filed Apr. 24, 2009.
Copending U.S. Appl. No. 12/446,249, filed Apr. 20, 2009.
Copending U.S. Appl. No. 12/446,615, filed Apr. 22, 2009.
Eichelberger, U. et al., "Synthesis of analogues of the 2-Oalkyl glycerate part of the moenomycins," *Tetrahedron* (2002) 58:545-559.
Granlund, L. et al., "Effects of structural changes of fatty acids on lipid accumulation in adipocytes and primary hepatocytes," *Biochimica et Biophysica Acta* (2005) 1687:23-30.
International Search Report for PCT/IB2007/004588 (U.S. Appl. No. 12/447,092) dated Nov. 21, 2008.
International Search Report for PCT/IB2007/004613 (U.S. Appl. No. 12/446,249) dated Apr. 16, 2009.
International Search Report for PCT/IB2007/003305 (U.S. Appl. No. 12/446,615) dated Mar. 20, 2008.
Itoh, T. et al., "Synthesis of docosahexaenoic acid derivatives designed as novel PPARγ agonists and antidiabetic agents," *Bioorganic & Med. Chem.* (2006) 98-108.
Kato, T. et al., "Abnormal Catabolites of Unsaturated Fatty Acids by in Vitro Reaction of Crude Enzyme from Infected Higher Plants," *Chem. Lett.* (1994) 4:761-762.
Kaufmann, H. P. and Kirschnek, A., "Fatty aldehydes. IV. Preparation of fatty aldehydes containing more than one double bond," *Fette, Seifen, Anstrichmittel* (1958) 60:1125-1132.
Kinsho, T. and Mori, K., "Synthesis of 3-Deoxy Analogs of Sphingolipids," *Agric. Biol. Chem.* (1989) 53(10):2785-2790.
Kuklev, D. V., et al., "Synthesis of C2-elongated polyunsaturated fatty acids," *Bioorganischeskaya Khimiya* (1996) 22(3):219-222.
Larsen, L. et al., "Sulfur-Substituted and α-Methylated Fatty Acids as Peroxisome Proliferator-Activated Receptor Activators" *Lipids* (2005) 40(1):49-57.
Larsen, L. N. et al., "α- and β- Alkyl-Substituted Eicosapentaenoic Acids: Incorporation into Phospholipids and Effects on Prostaglandin H Synthase and 5-Lipoxygenase" *Biochemical Pharmacology* (1998) 55(4):405-411.
Magrioti, V. et al., "Synthesis and in Vivo Anti-Inflammatory Activity of Long-chain 2-Amino-alcohols," *Bioorg. & Med. Chem. Lett.* (2003) 13:375-377.
Mangold, H. K., "Syntheses of Unsaturated Fatty Aldehydes," *J. Org. Chem.* (1959) 24:405-407.
Meyer A. et al., "Biosynthesis of Docosaheaenoic Acid in *Euglena gracilis*: Biochemical and Molecular Evidence for the Involvement of a Δ4-Fatty Acyl Group Desaturase" *Biochemistry* (2003) 42(32):9779-9788.
Pfeffer, P. E. et al., "A Anions of Carboxylic Acids. V. A Simple High Yield Presentation of α-Alkylhydracrylic Acids and α-Alkylacrylic Acids," *J. Org. Chem.* (1972) 37(8):1256-1258.
Sinha, S. C. and Keinan, E., "Total Synthesis of (+)-Aspicilin. The Naked Carbon Skeleton Strategy vs the Bicorganic Approach," *J. Org. Chem.* (1997) 62:377-386.
Vaagenes, H. et al., "Low Doses of Eicosapentaenoic Acid, Docosahexaenoic Acid, and Hypolipidemic Eicosapentaenoic Acid Derivatives Have No Effect on Lipid Peroxidation in Plasma" *Lipids* (1998) 33(11):1131-1137.
van der Linde, R. et al., "Synthesis of 2-substituted cis-8,cis-11,cis-14-eicosatrienoic acids, precursors for 2-substituted prostaglandins," *J. Royal Netherlands Chem. Soc.* (1975) 94(12):257-261.
Van Dorp, D. A. "Essential Fatty Acids and Prostaglandins," *Acta Biologica et Medica Germanica* (1976) 35(8-9):1041-1049.
Written Opinion for PCT/IB2007/004588 dated Nov. 21, 2008.
Written Opinion for PCT/IB2007/004613 dated Apr. 16, 2009.
Written Opinion for PCT/IB2007/003305 dated Mar. 20, 2008.
Combs, Colin K., et al., "Inflammatory Mechanisms in Alzheimer's Disease: Inhibition of β-Amyloid Stimulated Proinflammatory Responses and Neurotoxicity by PPARγ Agonists," *The Journal of Neuroscience* (2000) 20(2):558-567.
Copending U.S. Appl. No. 12/740,377, filed Apr. 29, 2010.
English abstract of JP 05-000974.
English abstract of JP 06-240289.
English abstract of JP 10-195023.
English Translation of JP 2003-283858.
Flock, Solveig, et al. "Syntheses of Some Polyunsaturated Sulfur and Oxygen-containing Fatty Acids Related to Eicosapentaenoic and Docosahexaenoic Acids" *Acta Chemica Scandinavica* (1999) 53:436-445.
International Search Report for PCT/IB2008/003666 (U.S. Appl. No. 12/740,377) dated Mary 24, 2009.
Nishikawa, M. et al., "Low-calorie omega-3 fatty acid glyceride health food," Database CAPLUS Chemical Abstracts XP002518330, STN Database Accession No. 2002:480253.
Notice of Allowance dated Jun. 8, 2011, from U.S. Appl. No. 12/111,589.
Office Action dated Apr. 14, 2010, from U.S. Appl. No. 12/111,589.
Office Action dated Aug. 6, 2009, from U.S. Appl. No. 12/111,589.
Office Action dated Jul. 14, 2010, from U.S. Appl. No. 12/111,589.
Office Action dated Jul. 24, 2008, from U.S. Appl. No. 11/417,252.
Office Action dated Nov. 29, 2007, from U.S. Appl. No. 11/417,252.
Tockizawa, K. et al., "Effects of phospholipids containing docosahexaenoic acid on differentiation and growth of HL-60 human promyelocytic leukemia cells," *J. Jpn. Oil Chem. Soc.* (1997) vol. 46, pp. 383-390.
Williams, J. et al., "Quantitative method for the profiling of the endocannabinoid metabolome by LC-Atmospheric Pressure Chemical Ionization-MS," *Anal. Chem.* (2007) vol. 79, pp. 5582-5593.
Willson, Timothy M., et al., "The PPARs: From Orphan Receptors to Drug Discovery," *Journal of Medicinal Chemistry* (2000) 43(4):527-550.
Banker, Gilbert S. et al., Modem Pharmaceutics, Marcel Dekker, New York, 1996, p. 451 and 596.
Copending U.S. Appl. No. 13/225,855, filed Sep. 6, 2011.
Desarnaud, F. et al., "Anandamide Amidohydrolase Activity in Rate Brain Microsomes," Journal of Biological Chemistry (1995) 270(11):6030-6035.
English Abstract of JP 2002-180082.
English Abstract of JP 2004-182674.
English Abstract of JP 57-149400.
English Abstract of JP 59-204175.
English Abstract of JP 6-293789.
English Abstract of JP 63-88159.
English Abstract of JP 7-53488.
English translation of Japanese Office Action in related application, JP 2008-509528; Dec. 6, 2011.

International Preliminary Report on Patentability for PCT/IB2006/001155 (U.S. Appl. No. 11/417,252) dated Nov. 6, 2007.
International Preliminary Report on Patentability for PCT/IB2007/004588 (U.S. Appl. No. 12/447,092) dated Mar. 27, 2009.
International Preliminary Report on Patentability for PCT/IB2007/004613 (U.S. Appl. No. 12/446,249) dated May 5, 2009.
International Preliminary Report on Patentability for PCT/IB2007/003305 (U.S. Appl. No. 12/446,615) dated Jan. 26, 2009.
International Preliminary Report on Patentability for PCT/IB2008/003666 (U.S. Appl. No. 12/740,377) dated May 4, 2010.
International Search Report for PCT/IB2006/001155 (U.S. Appl. No. 11/417,252) dated Aug. 10, 2006.
International Search Report for PCT/IB2011/000250 (U.S. Appl. No. 13/574,132) dated May 31, 2011.
Meyer, U.A., "Overview of Enzymes of Drug Metabolism," *Pharmacokinetics and Biopharmaceutics* (1996) 24:449-459.
Notice of Allowance dated Feb. 10, 2009, from U.S. Appl. No. 11/417,252.
Office Action dated Jul. 3, 2012, from U.S. Appl. No. 13/225,855.
Office Action dated May 17, 2012, from U.S. Appl. No. 12/447,092.
Supplementary European Search Report; EP 06 74 4648; Jun. 9, 2010.
Vaagenes, H., et al., "Methylated Eicosapentaenoic Acid and Tetradecylthioacetic Acid: Effects on Fatty Acid Metabolism", *Biochemical Pharmacology* (1999) 58:1133-1143.
West, Anthony R., *Solid State Chemistry and its Applications*, Wiley, New York, 1988, pp. 358 and 365.
Willumsen, N., et al., "On the effect of 2-deuterium- and 2-methyl-eicosapentaenoic acid derivatives on triglycerides, peroxiscomal β-oxidation and platelet aggregation in rats," *Biochimica et Biophysica Acta* (1998) 1369:193-203.
Wolff, Manfred E., *Burger's Medicinal Chemistry and Drug Discovery*, Fifth Ed., vol. 1: Principles and Practice, John Wiley & Sons, 1995, pp. 975-977.

* cited by examiner

ALPHA-SUBSTITUTED OMEGA-3 LIPIDS THAT ARE ACTIVATORS OR MODULATORS OF THE PEROXISOME PROLIFERATORS-ACTIVATED RECEPTOR (PPAR)

This is a national stage application under §371 of International Application No. PCT/IB2007/003305, filed Nov. 1, 2007, which claims the benefit of priority to Swedish Application No. 0602310-5, filed Nov. 1, 2006, and U.S. Provisional Application No. 60/855,733, filed Nov. 1, 2006. Each of these applications is incorporated herein by reference.

TECHNICAL FIELD

The present invention relates to omega-3 lipid compounds of the general formula (I):

(I)

It also relates to pharmaceutical compositions and lipid compositions comprising such compounds, and to such compounds for use as medicaments, in particular for the treatment of cardiovascular and metabolic diseases.

BACKGROUND OF THE INVENTION

Dietary polyunsaturated fatty acids (PUFAs) have effects on diverse physiological processes impacting normal health and chronic diseases, such as the regulation of plasma lipid levels, cardiovascular and immune functions, insulin action, and neuronal development and visual function. Ingestion of PUFAs (generally in ester form, e.g. in glycerides or phospholipids) will lead to their distribution to virtually every cell in the body with effects on membrane composition and function, eicosanoid synthesis, cellular signaling and regulation of gene expression.

Variations in distribution of different fatty acids/lipids to different tissues in addition to cell specific lipid metabolism, as well as the expression of fatty acid-regulated transcription factors, is likely to play an important role in determining how cells respond to changes in PUFA composition. (Benatti, P. Et al, J. Am. Coll. Nutr. 2004, 23, 281).

PUFAs or their metabolites have been shown to modulate gene transcription by interacting with several nuclear receptors. These are the peroxisome proliferators-activated receptors (PPARs), the hepatic nuclear receptor (HNF-4), liver X receptor (LXR), and the 9-cis retinoic acid receptor (retinoic X receptor, RXR). Treatment with PUFAs can also regulate the abundance of many transcriptional factors in the nucleus, including SREBP, NFkB, c/EBPβ, and HIF-1α. These effects are not due to direct binding of the fatty acid to the transcription factor, but involve mechanisms that affect the nuclear content of the transcription factors.

The regulation of gene transcription by PUFAs have profound effects on cell and tissue metabolism and offer a credible explanation for the involvement of nutrient-gene interactions in the initiation and prevention or amelioration of diseases such as obesity, diabetes, cardiovascular disorders, immune-inflammatory diseases and cancers (Wahle, J., et al, Proceedings of the Nutrition Society, 2003, 349).

Fish oils rich in the omega-3 polyunsaturated fatty acids eicosapentaenoic acid (EPA) and docosahexaenoic acid (DHA), have been shown to reduce the risk of cardiovascular diseases partly by reduction of blood triglyceride concentration. This favorable effect mainly results from the combined effects of inhibition of lipogenesis by decrease of SPEBP-1 and stimulation of fatty acid oxidation by activation of PPAR-α in the liver.

Omega-3 polyunsaturated fatty acids in fish oil have been reported to improve the prognosis of several chronic inflammatory diseases characterized by leukocyte accumulation and leukocyte-mediated tissue injury, including atherosclerosis, IgA nephropathy, inflammatory bowel disease, rheumatoid arthritis, psoriasis, etc. (Mishra, A., Arterioscler. Thromb. Vasc. Biol., 2004, 1621).

Due to their limited stability in vivo and their lack of biological specificity, PUFAs have not achieved widespread use as therapeutic agents. Chemical modifications of the omega-3 polyunsaturated fatty acids have been performed by several research groups in order to change or increase their metabolic effects.

For example, the hypolipidemic effects of EPA was potentiated by introducing methyl or ethyl in α-position of EPA ethyl ester. (Vaagenes et. al Biochemical Pharm. 1999, 58, 1133).

In a recent work published by L. Larsen (Larsen, L. et al, Lipids, 2005, 40, 49) the authors show that the α-methyl derivatives of EPA and DHA increased the activation of the nuclear receptor PPAR and thereby the expression of L-FABP compared to EPA/DHA. The authors suggest that delayed catabolism of these α-methyl PUFAs contribute to their increased effects.

Nuclear receptors (NRs) constitute a large and high conserved family of ligand activated transcriptional factors that regulate diverse biological processes such as development, metabolism, and reproduction. It is recognized that ligands for these receptors might be used in the treatment of common diseases such as atherosclerosis, diabetes, obesity, and inflammatory diseases. As such, NRs have become important drug targets, and the identification of novel NR ligands is a subject of much interest.

The activity of many nuclear receptors is controlled by the binding of small, lipophilic ligands that include hormones, metabolites such as fatty acids, bile acids, oxysterols and xeno- and endobiotics. Nuclear receptors can bind as monomers, homodimers, or RXR heterodimers to DNA.

The transcription factor NF-κB is an inducible eukaryotic transcription factor of the rel family. It is a major component of the stress cascade that regulate the activation of early response genes involved in the expression of inflammatory cytokines, adhesion molecules, heat-shock proteins, cyclooxygenases, lipoxygenases, and redox enzymes.

Zhao, G. et al (Biochemical and Biophysical Research Comm., 2005, 909) suggest that the anti-inflammatory effects of PUFAs in human monocytic THP-1 cells are in part mediated by inhibition of NF-κB activation via PPAR-γ activation. Others have suggested that the anti-inflammatory effect of PUFAs is mediated through a PPAR-α dependent inhibition of NF-κB activation.

To sum up, there is vast ongoing research in the field of PUFAs, and in particular omega-3 polyunsaturated fatty acids. However, their pharmaceutical potential has not yet been fully evaluated, and there is thus a continuing need for further evaluation and development of such compounds in order to increase their medical usefulness.

SUMMARY OF THE INVENTION

One object of the present invention is to provide omega-3 lipid compounds having pharmaceutical activity.

This object is achieved by an omega-3 lipid compound of formula (I):

(I)

wherein
R$_1$ and R$_2$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group; and X represents a carboxylic acid or a derivative thereof, a carboxylate, a carboxylic anhydride or a carboxamide, Y is a C$_{16}$ to C$_{22}$ alkene with two or more double bonds, having E and/or Z configuration or any pharmaceutically acceptable complex, salt, solvate or pro-drug thereof, with the provisos that:

R$_1$ and R$_2$ are not simultaneously a hydrogen atom or a fluorine atom; and the compound of formula (I) is not:
  a 2-substituted (all-Z)-4,7,10,13,16,19-docosahexaenoic acid in the form of a carboxylic acid, a carboxylate, a carboxylic anhydride or a carboxamide;
  (all-Z)-2-methyl-5,8,11,14,17 eicosapentaenoic acid, or its ethyl ester;
  (all-Z)-2-ethyl-5,8,11,14,17 eicosapentaenoic acid, or its ethyl ester;
  (all-Z)-2,2-dimethyl-5,8,11,14,17 eicosapentaenoic acid, or its ethyl ester;
  (all-Z)-2-benzyl-5,8,11,14,17 eicosapentaenoic acid, or its ethyl ester; or
  (all-Z)-2-hydroxy-9,12,15-octadecatrienoic acid, or its ethyl ester.
  (all-Z)-2-carboxy-6,9,12,15,18,21-tetracosahexaenoic acid
  ethyl (all-Z)-2-ethoxycarbonyl-6,9,12,15,18,21-tetracosahexaenoate In particular, the present invention relates to omega-3 lipid compounds of formula (I) wherein:

Y is a C$_{16}$-C$_{20}$ alkene with 2-6 double bonds;

Y is a C$_{16}$-C$_{20}$ alkene with 2-6 methylene interrupted double bonds in Z configuration;

Y is a C$_{16}$-C$_{20}$ alkene with 3-5 double bonds;

Y is a C$_{16}$-C$_{20}$ alkene with 3-5 methylene interrupted double bonds in Z configuration;

Y is a C$_{20}$ alkene with 5 double bonds in Z-configuration;

Y is a C$_{20}$ alkene with 5 methylene interrupted double bonds in Z configuration;

Y is a C$_{16}$ alkene with 3 double bonds in Z-configuration; or

Y is a C$_{16}$ alkene with 3 methylene interrupted double bonds in Z configuration.

The invention also relates to salts of the compound of formula (I). Such salts may be represented by

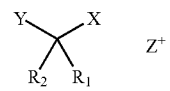

wherein X is COO$^-$,
Z$^+$ is selected from the group consisting of Li$^+$, Na$^+$, K$^+$, NH$_4^+$,

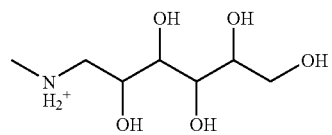

Meglumine,

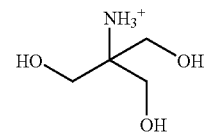

Tris(hydroxymethyl)aminomethane,

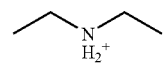

Diethylamine,
and

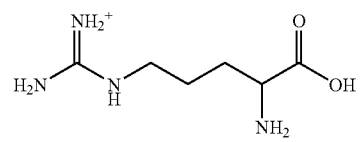

Arginine;
or by

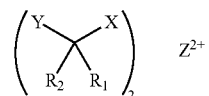

wherein X=COO$^-$,
Z$^{2+}$ is selected from the group consisting of Mg$^{2+}$, Ca$^{2+}$,

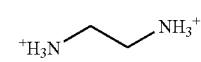

Ethylenediamine,
and

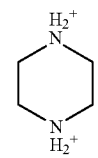

piperazine.

Another representative salt is

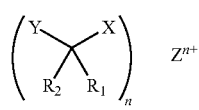

wherein X is COO⁻,
$Z^{n+}$ is

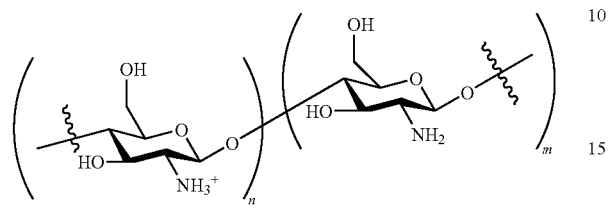

Chitosan

Furthermore, the present invention relates to compounds of formula (I), wherein X is a carboxylic acid in the form of a phospholipid. Such compounds may be represented by the following formulas,

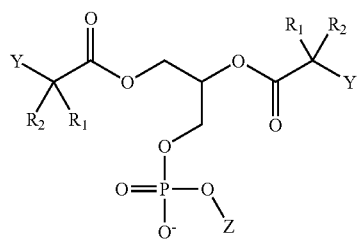

(II)

wherein
Z is

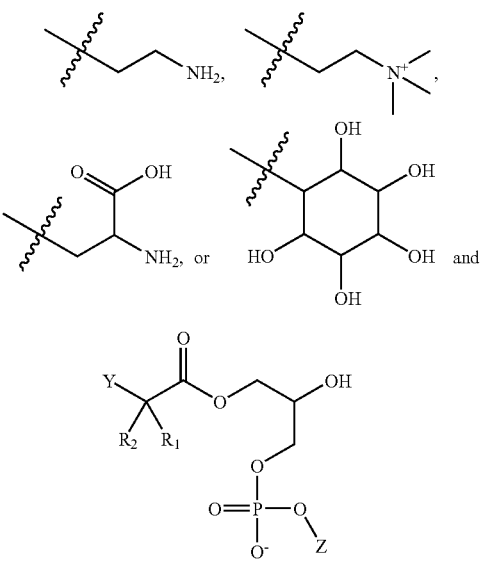

and (III)

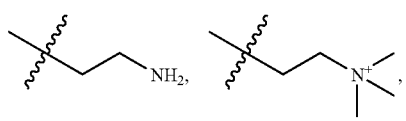

wherein
Z is

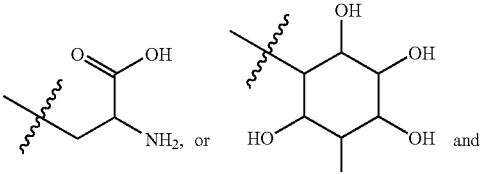

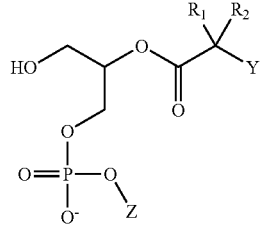

, or (IV)

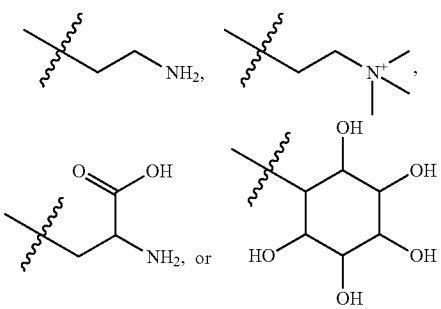

wherein
Z is

, or

Compounds of formula (I), wherein X is a carboxylic acid in the form of a triglyceride, a 1-monoglyceride and a 2-monoglyceride are also included in the present invention. These are hereinafter represented by the formulas (V), (VI) and (VII), respectively.

(V)

(VI)

(VII)

More precisely, the present invention relates to an omega-3 lipid compound selected from the group consisting of:
- (all-Z)-9,12,15-octadecatrienoic acid
- (all-Z)-6,9,12,15-octadecatetraenoic acid
- (all-Z)-7,10,13,16,19-docosapentaenoic acid
- (all-Z)-11,14,17-eicosatrienoic acid
- (all-Z)-6,9,12,15,18,21-tetracosahexaenoic acid
- (4E,8Z,11Z,14Z,17Z)-4,8,11,14,17-eicosapentaenoic acid
- (5E,8Z,11Z,14Z,17Z)-5,8,11,14,17-eicosapentaenoic acid
- (all-Z)-8,11,14,17-eicosatetraenoic acid
- (4E,7Z,10Z,13Z,16Z,19Z)-4,7,10,13,16,19-docosahexaenoic acid in the form of a carboxylic acid, or a derivative thereof, a carboxylate, a carboxylic anhydride or a carboxamide, or any pharmaceutically acceptable complex, salt, solvate or pro-drug thereof, wherein said compound is substituted at carbon 2 counted from the functional group of the omega-3 lipid compound, with at least one substituent selected from the group consisting of:

a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group with the provisos that the omega-3 lipid compound is not

- substituted with two hydrogen atoms
- (all-Z)-2-carboxy-6,9,12,15,18,21-tetracosahexaenoic acid
- ethyl (all-Z)-2-ethoxycarbonyl-6,9,12,15,18,21-tetracosahexaenoate
- (all-Z)-2-hydroxy-9,12,15-octadecatrienoic acid, or its ethyl ester Examples of salts of the above mentioned compounds include

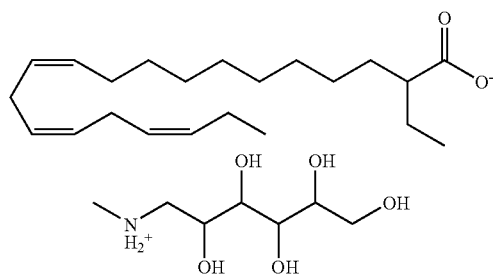

(all-Z)-2-ethyl-11,14,17-eicosatrienoic acid meglumine salt,

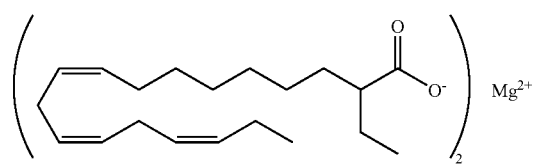

(all-Z)-2-ethyl-9,12,15-octadecatrienoic acid magnesium salt,

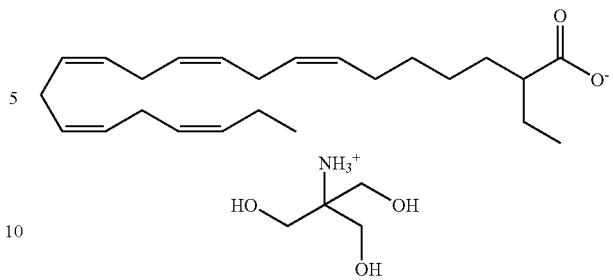

(all-Z)-2-ethyl-7,10,13,16,19-docosapentaenoic acid tris(hydroxymethy)aminomethane salt,

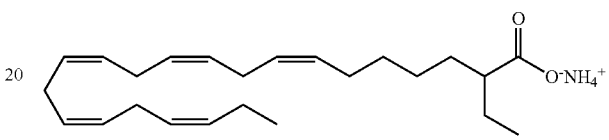

(all-Z)-2-ethyl-7,10,13,16,19-docosapentaenoic acid ammonium salt

In addition, the present invention relates to an omega-3 lipid compound, which is derived from (all-Z)-5,8,11,14,17-eicosapentaenoic acid (EPA). Such a compound can be represented by the following formula

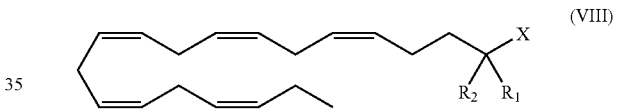

(VIII)

in the form of a carboxylic acid, or a derivative thereof, a carboxylate, a carboxylic anhydride or a carboxamide, represented by X or any pharmaceutically acceptable complex, salt, solvate or pro-drug thereof, wherein $R_1$ and $R_2$ are the same or different and may be selected from the group consisting of a hydrogen atom, a hydroxy group, a $C_3$-$C_7$ alkyl group, a halogen atom, an alkoxy group, an acyloxy group, an acyl group, an alkenyl group, an alkynyl group, an alkylthio group, an alkoxycarbonyl group, a carboxy group, an alkylsulfinyl group, an alkylsulfonyl group, an amino group, and an alkylamino group with the proviso that $R_1$ and $R_2$ are not simultaneously a hydrogen atom. Typically, $R_1$ and $R_2$ are selected from a hydrogen atom, a $C_3$-$C_7$ alkyl group, an alkoxy group, an alkylthio group, an amino group, an alkylamino group, an alkoxycarbonyl group, and a carboxy group. More typically $R_1$ and $R_2$ are selected from a hydrogen atom, a $C_3$-$C_7$ alkyl group, preferably propyl, a $C_1$-$C_7$ alkoxy group, preferably methoxy, ethoxy or propoxy, a $C_1$-$C_7$ alkylthio group, preferably methylthio, ethylthio, or propylthio, an amino group, a $C_1$-$C_7$ alkylamino group, preferably an ethylamino or diethylamino group, a $C_1$-$C_7$ alkoxycarbonyl group, and a carboxy group.

the compound is substituted at carbon 2, counted from the functional group of the omega-3 lipid compound, with two substituents, represented by $R_1$ and $R_2$, selected from the group consisting of a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, with the proviso that said compound is not 2,2,-dimethyl-5,8,11,14,17 eicosapentaenoic acid. Typically, $R_1$ and $R_2$ are selected from an alkyl group, an alkoxy group, an alkylthio group, an amino group, an alkylamino group, an alkoxycarbonyl group, and a carboxy group. More typically, $R_1$ and $R_2$ are selected from a $C_1$-$C_7$ alkyl group, preferably methyl, ethyl, or propyl, a $C_1$-$C_7$ alkoxy group, preferably methoxy, ethoxy or propoxy, a $C_1$-$C_7$ alkylthio group, preferably methylthio, ethylthio, or propylthio, an amino group, a $C_1$-$C_7$ alkylamino group, preferably ethylamino or diethylamino, a $C_1$-$C_7$ alkoxycarbonyl group, and a carboxy group.

In the compounds of formulas (I) and (VIII), X typically represents an carboxylate or a carboxylic acid. However, X may also be a derivative of a carboxylic acid in the form of phospholipid or a tri-di, or monoglyceride.

Furthermore, the present invention relates to an omega-3 lipid compound, which is derived from (all-Z)-5,8,11,14,17-eicosapentaenoic acid (EPA), represented by formula (VIII)

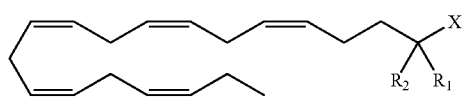

(VIII)

in the form of a phospholipid, a tri-, di-, or monoglyceride, a carboxylate, a carboxylic anhydride or a carboxamide, represented by X, or any pharmaceutically acceptable complex, salt, solvate or pro-drug thereof, wherein $R_1$ and $R_2$ are the same or different and may be selected from the group consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, with the proviso that $R_1$ and $R_2$ are not simultaneously a hydrogen atom. The compound of formula (VIII) is not any one of (all-Z)-2-methyl-5,8,11,14,17 eicosapentaenoic acid, or its ethyl ester;

(all-Z)-2-ethyl-5,8,11,14,17 eicosapentaenoic acid, or its ethyl ester;

(all-Z)-2,2-dimethyl-5,8,11,14,17 eicosapentaenoic acid, or its ethyl ester.

Typically, $R_1$ and $R_2$ are the same or different and are selected from a hydrogen atom, an alkyl group, an alkoxy group, an alkylthio group, an amino group, an alkylamino group, an alkoxycarbonyl group, and a carboxy group. More typically, $R_1$ and $R_2$ are selected from a hydrogen atom, a $C_1$-$C_7$ alkyl group, preferably methyl, ethyl, or propyl, a $C_1$-$C_7$ alkoxy group, preferably methoxy, ethoxy or propoxy, a $C_1$-$C_7$ alkylthio group, preferably methylthio, ethylthio, or propylthio an amino group, a $C_1$-$C_7$ alkylamino group, preferably ethylamino or diethylamino, a $C_1$-$C_7$ alkoxycarbonyl group, and a carboxy group.

In compounds of formula (VIII) above, X may represent a carboxylate or a carboxylic acid. However, X may also be represented by a carboxylic acid in the form of a phospholipid according to the formulas (II), (III) and (IV) specified above. Examples of such compounds include:

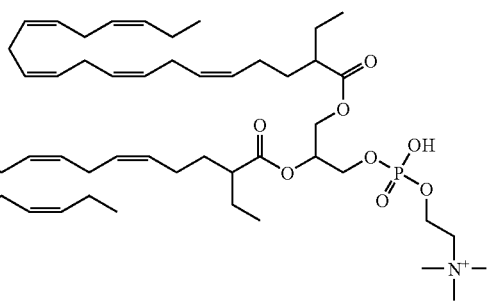

1,2-Di((all-Z)-2-ethyl-5,8,11,14,17-eicosapentaenoyl)-sn-glycero-3-phosphocholine,

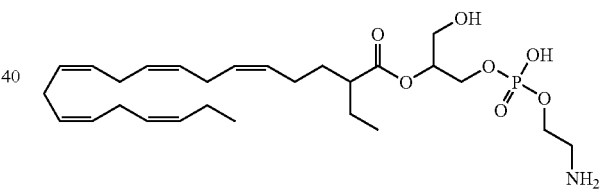

2-(all-Z)-2-ethyl-5,8,11,14,17-eicosapentaenoyl-sn-glycero-3-phosphoethanolamine Furthermore X may also be represented by a carboxylic acid in the form of a triglyceride according to formula (V) above. An example of such a compound is

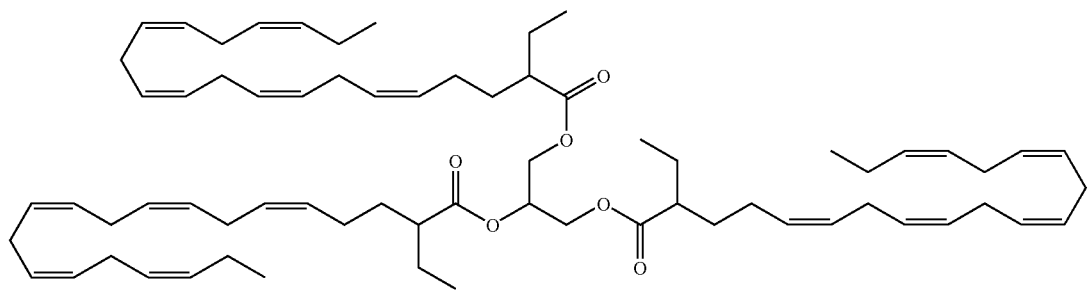 [SMILES: CC/C=C\C/C=C\C/C=C\C/C=C\C/C=C\CCC(CC)C(=O)OCC(COC(=O)C(CC)CC/C=C\C/C=C\C/C=C\C/C=C\C/C=C\CC)OC(=O)C(CC)CC/C=C\C/C=C\C/C=C\C/C=C\C/C=C\CC]

1,2,3-tris((all-Z)-2-ethyl-5,8,11,14,17-eicosapentaenoyl)-sn-glycerol.

X may also be represented by a carboxylic acid in the form of a 2-monoglyceride of formula (VII). An example of such a compound is

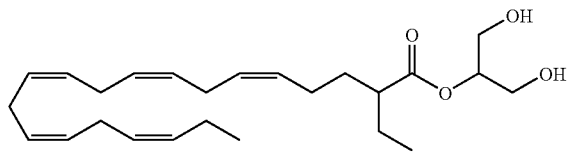 [SMILES: CC/C=C\C/C=C\C/C=C\C/C=C\C/C=C\CCC(CC)C(=O)OC(CO)CO]

2-((all-Z)-2-ethyl-5,8,11,14,17-eicosapentaenoyl)-sn-glycerol

In a compound according to the invention, said alkyl group may be selected from the group consisting of methyl, ethyl, n-propyl, isopropyl, n-butyl, iso-butyl, sec.-butyl, and n-hexyl; said halogen atom may be fluorine; said alkoxy group may be selected from the group consisting of methoxy, ethoxy, propoxy, isopropoxy, sec.-butoxy, phenoxy, benzyloxy, $OCH_2CF_3$, and $OCH_2CH_2OCH_3$; said alkenyl group may be selected from the group consisting of allyl, 2-butenyl, and 3-hexenyl; said alkynyl group may be selected from the group consisting of propargyl, 2-butynyl, and 3-hexynyl; said aryl group may be selected from a benzyl group, and a substituted benzyl group; said alkylthio group may be selected from the group consisting of methylthio, ethylthio, isopropylthio, and phenylthio; said alkoxycarbonyl group may be selected from the group consisting of methoxycarbonyl, ethoxycarbonyl, propoxycarbonyl, and butoxycarbonyl; said alkylsulfinyl group may be selected from the group consisting of methanesulfinyl, ethanesulfinyl, and isopropanesulfinyl; said alkylsulfonyl group may be selected from the group consisting of methanesulfonyl, ethanesulfonyl, and isopropanesulfonyl; and said alkylamino group may be selected from the group consisting of methylamino, dimethylamino, ethylamino, and diethylamino.

The derivative of a carboxylic acid may be a phospholipid, or a tri-, di-, or monoglyceride, i.e. the compound according to the invention may exist in the form of a phospholipid, a tri-, di- or monoglyceride, or in the form of a free acid.

According to the present invention, said carboxylate group may be selected from the group consisting of ethyl carboxylate, methyl carboxylate, n-propyl carboxylate, isopropyl carboxylate, n-butyl carboxylate, sec.-butyl carboxylate, and n-hexyl carboxylate, and said carboxamide group may be selected from the group consisting of primary carboxamide, N-methyl carboxamide, N,N-dimethyl carboxamide, N-ethyl carboxamide, and N,N-diethyl carboxamide.

Examples of compounds according to the invention are those in which X is ethylcarboxylate, and Y is a $C_{16}$ alkene with 3 methylene interrupted double bonds, located in Z configuration in positions 9, 12, and 15, wherein:
one of $R_1$ and $R_2$ is methyl and the other one is a hydrogen atom;
one of $R_1$ and $R_2$ is ethyl and the other one is a hydrogen atom;
one of $R_1$ and $R_2$ is propyl and the other one is a hydrogen atom;
one of $R_1$ and $R_2$ is methoxy and the other one is a hydrogen atom;
one of $R_1$ and $R_2$ is ethoxy and the other one is a hydrogen atom;
one of $R_1$ and $R_2$ is propoxy and the other one is a hydrogen atom;
one of $R_1$ and $R_2$ is thiomethyl and the other one is a hydrogen atom;
one of $R_1$ and $R_2$ is thioethyl and the other one is a hydrogen atom;
one of $R_1$ and $R_2$ is thiopropyl and the other one is a hydrogen atom;
one of $R_1$ and $R_2$ is ethylamino and the other one is a hydrogen atom;
one of $R_1$ and $R_2$ is diethylamino and the other one is a hydrogen atom; or
one of $R_1$ and $R_2$ is amino and the other one is a hydrogen atom.

Other examples of compounds according to the invention are those in which X is ethylcarboxylate, and Y is a $C_{20}$ alkene with 5 methylene interrupted double bonds located in Z configuration in positions 7, 10, 13, 16 and 19, wherein:
one of $R_1$ and $R_2$ is methyl and the other one is a hydrogen atom;
one of $R_1$ and $R_2$ is ethyl and the other one is a hydrogen atom;
one of $R_1$ and $R_2$ is propyl and the other one is a hydrogen atom;
one of $R_1$ and $R_2$ is methoxy and the other one is a hydrogen atom;
one of $R_1$ and $R_2$ is ethoxy and the other one is a hydrogen atom;
one of $R_1$ and $R_2$ is propoxy and the other one is a hydrogen atom;
one of $R_1$ and $R_2$ is thiomethyl and the other one is a hydrogen atom;
one of $R_1$ and $R_2$ is thioethyl and the other one is a hydrogen atom; or
one of $R_1$ and $R_2$ is thiopropyl and the other one is a hydrogen atom.

In the omega-3 lipid compound according to formula (I) of the present invention, $R_1$ and $R_2$ may be the same or different. When they are different, the compounds of formula (I) are capable of existing in stereoisomeric forms. It will be understood that the invention encompasses all optical isomers of the compounds of formula (I) and mixtures thereof, including racemates. Therefore, the present invention includes, where $R_1$ is different from $R_2$, compounds of formula (I) that are racemic or enantiomerically pure, either as the (S) or (R) enantiomer.

The present invention also relates to an omega-3 compound according of formula (I) for use as a medicament or for diagnostic purposes, for instance positron emission tomography (PET).

Further, the present invention relates to a pharmaceutical composition comprising an omega-3 lipid compound according to formula (I). The pharmaceutical composition may comprise a pharmaceutically acceptable carrier, excipient or diluent, or any combination thereof, and is suitably formulated for oral administration, e.g. in the form of a capsule or a sachet. A suitable daily dosage of the compound according to formula (I) is 1 mg to 10 g of said compound; 50 mg to 1 g of said compound, or 50 mg to 200 mg of said compound.

The present invention also relates to lipid composition comprising an omega-3 lipid compound according to formula (I). Suitably, at least 60% by weight, or at least 80% by weight of the lipid composition is comprised of said compound. The lipid composition may further comprise fatty acids selected from (all-Z)-5,8,11,14,17-eicosapentaenoic acid (EPA), (all-Z)-4,7,10,13,16,19-docosahexaenoic acid (DHA), (all-Z)-6,9,12,15,18-heneicosapentaenoic acid (HPA), and/or (all-Z)-7,10,13,16,19-docosapentaenoic acid (DPA), or derivatives thereof, i.e. presented in their alpha substituted form, and/or a pharmaceutically acceptable antioxidant, e.g. tocopherol.

Further, the invention relates to the use of an omega-3 lipid compound according to formula (I) for the production of a medicament for:

- activation or modulation of at least one of the human peroxisome proliferator-activated receptor (PPAR) isoforms, wherein said peroxisome proliferator-activated receptor (PPAR) is peroxisome proliferator-activated receptor (PPAR)α and/or γ.
- the treatment and/or the prevention of peripheral insulin resistance and/or a diabetic condition.
- reduction of plasma insulin, blood glucose and/or serum triglycerides.
- the treatment and/or the prevention of type 2 diabetes.
- the prevention and/or treatment of elevated triglyceride levels, and/or non-HDL cholesterol, LDL cholesterol and VLDL cholesterol levels
- the prevention and/or treatment of a hyperlipidemic condition, e.g. hypertriglyceridemia (HTG).
- increasing serum HDL levels in humans.
- the treatment and/or the prevention of obesity or an overweight condition.
- reduction of body weight and/or for preventing body weight gain.
- the treatment and/or the prevention of a fatty liver disease, e.g. non-alcoholic fatty liver disease (NAFLD).
- treatment of insulin resistance, hyperlipidemia and/or obesity or an overweight condition.
- the production of a medicament for the treatment and/or the prevention of an inflammatory disease or condition.

The invention also relates to a compound according to formula (I) for the treatment and/or prevention of the conditions listed above, and to methods for the treatment and/or prevention of the conditions listed above, comprising administering to a mammal in need thereof a pharmaceutically active amount of a compound according to formula (I).

According to the invention, introducing at least one substituent in the α-position of different polyunsaturated fatty acids leads to an accumulation of fatty acid derivatives in the NEFA pool, rather than incorporation into neutral lipids or oxidation of these fatty acids. The omega-3 lipid compounds according to the present invention accumulates in the intracellular NEFA pool and trigger local nuclear receptor activity to a greater extent than unsubstituted fatty acids.

Different substituents of the PUFAs according to the invention will give variable affinities of the derivatives to nuclear receptors, and in particular to the PPARs. Changes in affinity to the different receptor in addition to different co-factor recruitment lead to changes in the biological activity of these α-substituted lipid derivatives of formula (I).

Because different PUFAs accumulate differently in different tissues, these modified PUFAs have the potential for being tissue specific ligands for nuclear receptors. Because many of the nuclear receptors are distributed differently in different tissues it is important to make ligands that in vivo are able to target specified cells in order to bind and activate the target receptor.

In addition to being better ligands for nuclear receptors, the derivatives of the invention are not as easily degraded by α- and β-oxidation pathways as natural PUFAs due to substitution in α-position.

Nomenclature and Terminology

Fatty acids are straight chain hydrocarbons possessing a carboxyl (COOH) group at one end (α) and (usually) a methyl group at the other (ω) end. In physiology, fatty acids are named by the position of the first double bond from the ω end. The term ω-3 (omega-3) signifies that the first double bond exists as the third carbon-carbon bond from the terminal $CH_3$ end (ω) of the carbon chain. In chemistry, the numbering of the carbon atoms starts from the α end.

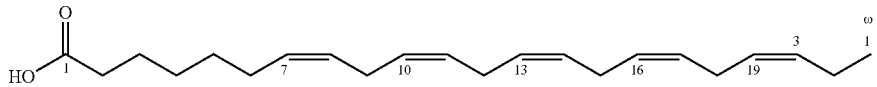 [SMILES: CC/C=C\C/C=C\C/C=C\C/C=C\C/C=C\CCCCCC(=O)O]

In addition, the present invention encompasses methods for manufacturing omega-3 lipid compounds according to formula (I).

DETAILED DESCRIPTION OF THE INVENTION

In the research work leading to the present invention, it was surprisingly found that omega-3 lipid compounds represented by the general formula (I) have a remarkably high affinity for the nuclear receptors of the PPAR family.

It is known that PPARα is the most promiscuous of the PPARs, interacting with both saturated and unsaturated fatty acids. PPARδ interacts with saturated and unsaturated fatty acids, albeit less efficiently than PPARα. PPARγ shows the most restricted fatty acid binding profile, interacting most efficiently with PUFAs and only weakly with monounsaturated fatty acids (Xu et al, Molecular Cell, 1999, 397-403).

The effects of the PUFAs on these nuclear receptors are not only a result of fatty acid structure and affinity to the receptor. Factors contributing to the composition of the intracellular non-esterified fatty acids (NEFA) levels are also important. This NEFA pool is affected by the concentration of exogenous fatty acids entering the cell and the amount of endogenous synthesised fatty acids, their removal via incorporation into lipids as well as their oxidation pathways. (Pawar, A. & Jump, D B, Journal of Biological chem., 2003, 278, 35931).

As used herein, the expression "methylene interrupted double bonds" relates to the case when a methylene group is located between to separate double bonds in a carbon chain of an omega-3 lipid compound.

Throughout this specification, the terms "2-substituted", substituted in position 2, and "substituted at carbon 2, counted from the functional group of the omega-3 lipid compound" refers to a substitution at the carbon atom denoted 2 in accordance with the above numbering of the carbon chain. Alternatively, such a substitution may be called an "alpha substitution".

Throughout this specification, the term "omega-3 lipid compound" (corresponding to (ω-3, or n-3) relates to a lipid compound having the first double bond at the third carbon-carbon bond from the ω end of the carbon chain, as defined above.

The basic idea of the present invention is an omega-3 lipid compound of formula (I):

wherein
$R_1$ and $R_2$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group;

X represents a carboxylic acid or a derivative thereof, a carboxylate, a carboxylic anhydride or a carboxamide; and Y is a $C_{16}$ to $C_{22}$ alkene with two or more double bonds, having E and/or Z configuration.

The resulting compound is an alpha substituted omega-3 lipid compound, i.e. an omega-e lipid compound substituted in position 2 of the carbon atom, counted from the carbonyl end. More particularly, the resulting compound is an alpha substituted polyunsaturated omega-3 fatty acid, which may be present as a carboxylic acid, or a derivative thereof, as a carboxylate, as a carboxylic anhydride or as a carboxamide. The present inventors have surprisingly found that the following omega-3 fatty acids are particularly suitable for being substituted in alpha position as outlined in formula (I):

(all-Z)-9,12,15-octadecatrienoic acid
(all-Z)-6,9,12,15-octadecatetraenoic acid
(all-Z)-7,10,13,16,19-docosapentaenoic acid
(all-Z)-11,14,17-eicosatrienoic acid
(all-Z)-6,9,12,15,18,21-tetracosahexaenoic acid
(4E,8Z,11Z,14Z,17Z)-4,8,11,14,17-eicosapentaenoic acid
(5E,8Z,11Z,14Z,17Z)-5,8,11,14,17-eicosapentaenoic acid
(all-Z)-8,11,14,17-eicosatetraenoic acid
(4E,7Z,10Z,13Z,16Z,19Z)-4,7,10,13,16,19-docosahexaenoic acid.

Among the possible substituents listed above, lower alkyl groups, in particular methyl and ethyl groups, have proven very useful for achieving the desired pharmaceutical activity. Other very useful substituents are lower alkylthio and lower alkylamino groups, e.g. having 1-3 carbon atoms. The substitution of either $R_1$ or $R_2$ with one of these suitable substituents, while the other one is hydrogen, is believed to provide the most efficient result.

(all-Z)-5,8,11,14,17-eicosapentaenoic acid (EPA) is another omega-3 fatty acid which has proven useful for substitution in its alpha position as suggested according to the present invention. For EPA, suitable substituents are lower alkylthio groups and lower alkylamino groups, e.g. having 1-3 carbon atoms. By analogy with the above, the substitution of either $R_1$ or $R_2$ with one of these substituents, while the other one is hydrogen, is believed to provide the most efficient result. The case when both $R_1$ and $R_2$ are ethyl is another suitable substitution of EPA.

Preferred omega-3 lipid compounds according to the present invention are divided into the following categories A-F:

Category A—(all-Z)-9,12,15-octadecatrienoic acid (alpha-linolenic acid, ALA) in the form of a carboxylic acid, or a derivative thereof, a carboxylate, a carboxylic anhydride or a carboxamide, substituted in position 2:

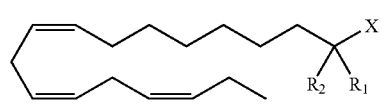

$Y=C_{16}$ alkene with 3 double bonds in Z-configuration in positions 9, 12 and 15

Category B—(all-Z)-7,10,13,16,19-docosapentaenoic acid (clupanodonic acid, DPA) in the form of a carboxylic acid, or a derivative thereof, a carboxylate, a carboxylic anhydride or a carboxamide, substituted in position 2:

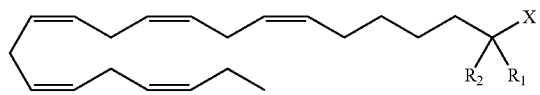

$Y=C_{20}$ alkene with 5 double bonds in Z-configuration in positions 7, 10, 13, 16 and 19

Category C—(all-Z)-11,14,17-eicosatrienoic acid in the form of a carboxylic acid, or a derivative thereof, a carboxylate, a carboxylic anhydride or a carboxamide, substituted in position 2:

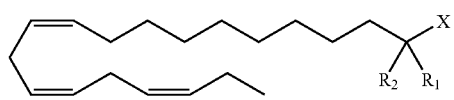

$Y=C_{18}$ alkene with 3 double bonds in Z-configuration in positions 11, 14, and 17

Category D—(4E,8Z,11Z,14Z,17Z)-eicosapentaenoic acid in the form of a carboxylic acid, or a derivative thereof, a carboxylate, a carboxylic anhydride or a carboxamide, substituted in position 2:

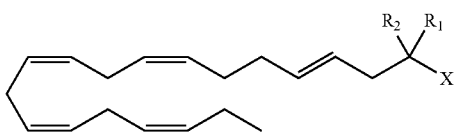

$Y=C_{18}$ alkene with 5 double bonds in positions 4, 8, 11, 14, and 17, where the double bonds in position 8, 11, 14 and 17 are in Z-configuration, and the double bond in position 4 is in E configuration Category E—(all-Z)-5,8,11,14,17-eicosapentaenoic acid (EPA) in the form of a carboxylic acid, or a derivative thereof, a carboxylate, a carboxylic anhydride or a carboxamide, substituted in position 2:

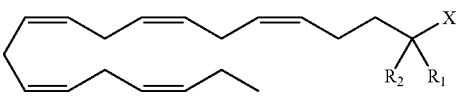

$Y=C_{18}$ alkene with 5 double bonds in Z-configuration in positions 5, 8, 11, 14, and 17.

Category F—(4E,7Z,10Z,13Z,16Z,19Z)-docosahexaenoic acid (trans-DHA) in the form of a carboxylic acid, or a derivative thereof, a carboxylate, a carboxylic anhydride or a carboxamide, substituted in position 2:

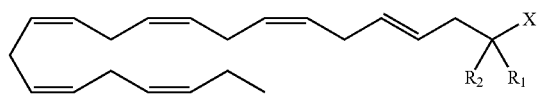

$Y=C_{20}$ alkene with 6 double bonds in positions 4, 7, 10, 13, 16, and 19, where the double bonds in position 7, 10, 13, 16, and 19 are in Z-configuration, and the double bond in position 4 is in E configuration.

Specific examples of preferred omega-3 lipid compounds according to the invention are:

Category A

EXAMPLES (1)-(12)

For all examples (1)-(12):
X=ethylcarboxylate
Y=$C_{16}$ alkene with 3 double bonds in Z-configuration in positions 9, 12 and 15

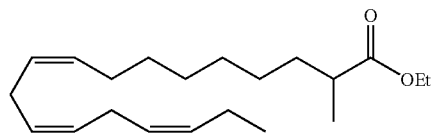 [SMILES: CC/C=C\C/C=C\C/C=C\CCCCCCC(C)C(=O)OCC]

Ethyl (all-Z)-2-methyl-9,12,15-octadecatrienoate (1)

$R_1$=methyl, and $R_2$=a hydrogen atom, or
$R_2$=methyl, and $R_1$=a hydrogen atom

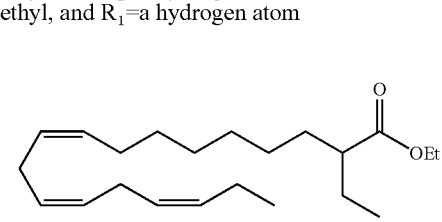

Ethyl (all-Z)-2-ethyl-9,12,15-octadecatrienoate (2)

$R_1$=ethyl, and $R_2$=a hydrogen atom, or
$R_2$=ethyl, and $R_1$=a hydrogen atom

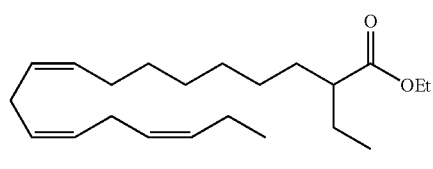

Ethyl (all-Z)-2-propyl-9,12,15-octadecatrienoate (3)

$R_1$=propyl, and $R_2$=a hydrogen atom, or
$R_2$=propyl, and $R_1$=a hydrogen atom

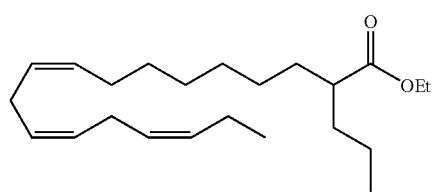 [SMILES: CC/C=C\C/C=C\C/C=C\CCCCCCC(CCC)C(=O)OCC]

Ethyl (all-Z)-2-methoxy-9,12,15-octadecatrienoate (4)

$R_1$=methoxy, and $R_2$=a hydrogen atom, or
$R_2$=methoxy, and $R_1$=a hydrogen atom

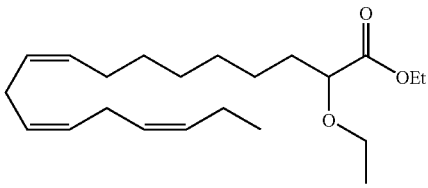 [SMILES: CC/C=C\C/C=C\C/C=C\CCCCCCC(OCC)C(=O)OCC]

Ethyl (all-Z)-2-ethoxy-9,12,15-octadecatrienoate (5)

$R_1$=ethoxy, and $R_2$=a hydrogen atom, or
$R_2$=ethoxy, and $R_1$=a hydrogen atom

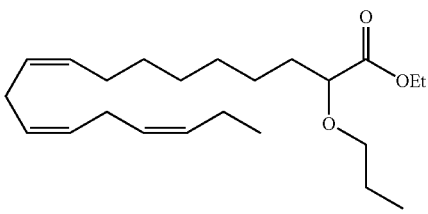

Ethyl (all-Z)-2-propoxy-9,12,15-octadecatrienoate (6)

$R_1$=propoxy, and $R_2$=a hydrogen atom, or
$R_2$=propoxy, and $R_1$=a hydrogen atom

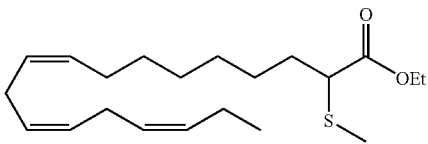 [SMILES: CC/C=C\C/C=C\C/C=C\CCCCCCC(SC)C(=O)OCC]

Ethyl (all-Z)-2-thiomethyl-9,12,15-octadecatrienoate (7)

$R_1$=methylthio, and $R_2$=a hydrogen atom, or
$R_2$=methylthio, and $R_1$=a hydrogen atom

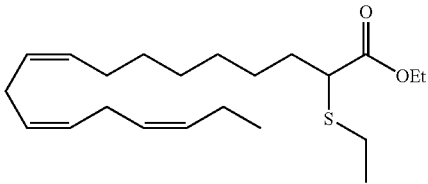 [SMILES: CC/C=C\C/C=C\C/C=C\CCCCCCC(SCC)C(=O)OCC]

Ethyl (all-Z)-2-thioethyl-9,12,15-octadecatrienoate (8)

$R_1$=ethylthio, and $R_2$=a hydrogen atom, or
$R_2$=ethylthio, and $R_1$=a hydrogen atom

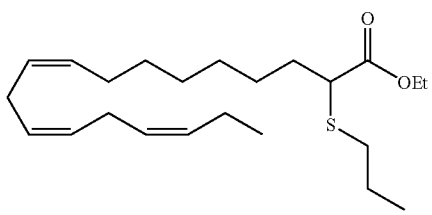 [SMILES: CC/C=C\C/C=C\C/C=C\CCCCCCC(SCCC)C(=O)OCC]

Ethyl (all-Z)-2-thiopropyl-9,12,15-octadecatrienoate (9)

$R_1$=propylthio, and $R_2$=a hydrogen atom, or
$R_2$=propylthio, and $R_1$=a hydrogen atom

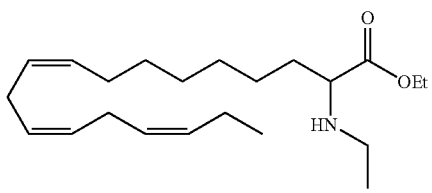 [SMILES: CC/C=C\C/C=C\C/C=C\CCCCCCC(NCC)C(=O)OCC]

Ethyl (all-Z)-2-ethylamino-9,12,15-octadecatrienoate (10)

$R_1$=ethylamino, and $R_2$=a hydrogen atom, or
$R_2$=ethylamino, and $R_1$=a hydrogen atom

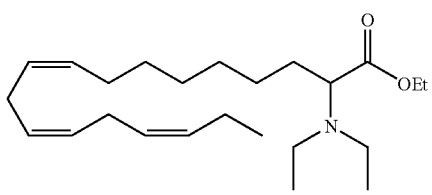 [SMILES: CC/C=C\C/C=C\C/C=C\CCCCCCC(C(=O)OCC)N(CC)CC]

Ethyl (all-Z)-2-diethylamino-9,12,15-octadecatrienoate (11)

$R_1$=diethylamino, and $R_2$=a hydrogen atom, or
$R_2$=diethylamino, and $R_1$=a hydrogen atom

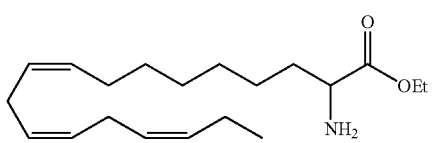

Ethyl (all-Z)-2-amino-9,12,15-octadecatrienoate (12)

$R_1$=amino, and $R_2$=a hydrogen atom, or
$R_2$=amino, and $R_1$=a hydrogen atom Category B

EXAMPLES (13)-(21)

For all examples (13)-(21):
X=ethylcarboxylate
Y=$C_{20}$ alkene with 5 double bonds in Z-configuration in positions 7, 10, 13, 16 and 19

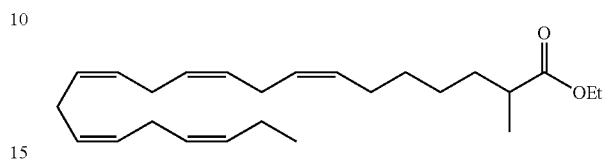

Ethyl (all-Z)-2-methyl-7,10,13,16,19-docosapentaenoate (13)

R=methyl, and $R_2$=a hydrogen atom, or
$R_2$ methyl, and $R_1$=a hydrogen atom

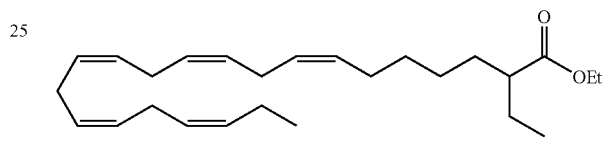

Ethyl (all-Z)-2-ethyl-7,10,13,16,19-docosapentaenoate (14)

$R_1$=ethyl, and $R_2$=a hydrogen atom, or
$R_2$=ethyl, and $R_1$=a hydrogen atom

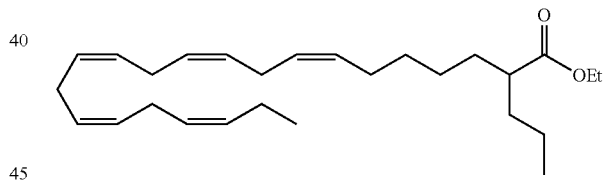

Ethyl (all-Z)-2-propyl-7,10,13,16,19-docosapentaenoate (15)

$R_1$=propyl, and $R_2$=a hydrogen atom, or
$R_2$=propyl, and $R_1$=a hydrogen atom

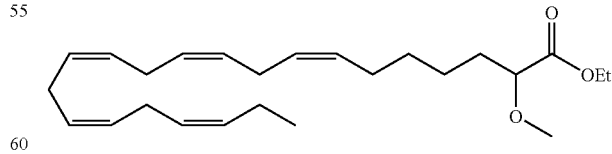

Ethyl (all-Z)-2-methoxy-7,10,13,16,19-docosapentaenoate (16)

$R_1$=methoxy, and $R_2$=a hydrogen atom, or
$R_2$=methoxy, and $R_1$=a hydrogen atom

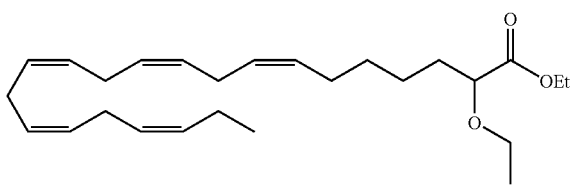 [SMILES: CC/C=C\C/C=C\C/C=C\C/C=C\C/C=C\CCCCC(CCC)C(=O)OCC]

Ethyl (all-Z)-2-ethoxy-7,10,13,16,19-docosapentaenoate (17)

$R_1$=ethoxy, and $R_2$=a hydrogen atom, or
$R_2$=ethoxy, and $R_1$=a hydrogen atom

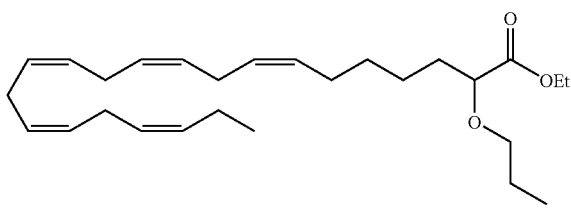 [SMILES: CC/C=C\C/C=C\C/C=C\C/C=C\C/C=C\CCCCC(SCCC)C(=O)OCC]

Ethyl (all-Z)-2-propoxy-7,10,13,16,19-docosapentaenoate (18)

$R_1$=propoxy, and $R_2$=a hydrogen atom, or
$R_2$=propoxy, and $R_1$=a hydrogen atom

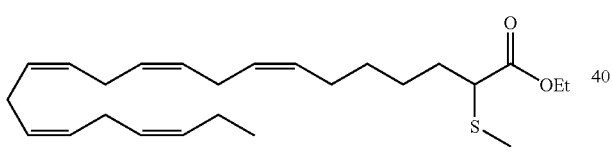

Ethyl (all-Z)-2-thiomethyl-7,10,13,16,19-docosapentaenoate (19)

$R_1$=methylthio, and $R_2$=a hydrogen atom, or
$R_2$=methylthio, and $R_1$=a hydrogen atom

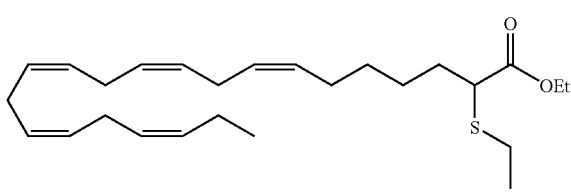

Ethyl (all-Z)-2-thioethyl-7,10,13,16,19-docosapentaenoate (20)

$R_1$=ethylthio, and $R_2$=a hydrogen atom, or
$R_2$=ethylthio, and $R_1$=a hydrogen atom

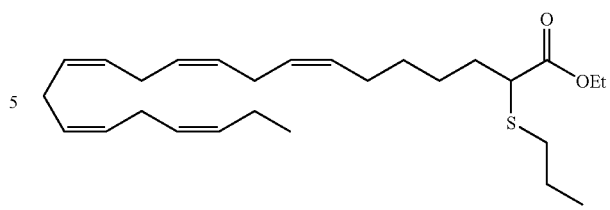

Ethyl (all-Z)-2-thiopropyl-7,10,13,16,19-docosapentaenoate (21)

$R_1$=propylthio, and $R_2$=a hydrogen atom, or
$R_2$=propylthio, and $R_1$=a hydrogen atom Category C EXAMPLES (23)-(24) and (27)-(35)

For all examples (23)-(24) and (27)-(35):
Y=$C_{18}$ alkene with 3 double bonds in Z-configuration in positions 11, 14, and 17

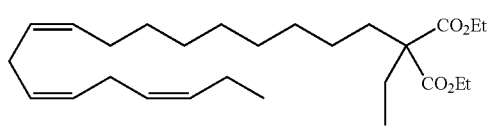 [SMILES: CC/C=C\C/C=C\C/C=C\CCCCCCCCC(CC)(C(=O)OCC)C(=O)OCC]

Ethyl (all-Z)-2-ethyl,2-ethoxycarbonyl-11,14,17-eicosatrienoate (23)

$R_1$=ethoxycarbonyl, and $R_2$=ethyl, or
$R_2$=ethoxycarbonyl, and $R_1$=ethyl
X=ethylcarboxylate

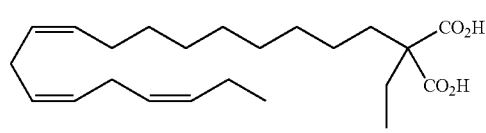 [SMILES: CC/C=C\C/C=C\C/C=C\CCCCCCCCC(CC)(C(=O)O)C(=O)O]

(all-Z)-2-ethyl,2-carboxy-11,14,17-eicosatrienoic acid (24)

$R_1$=carboxy, and $R_2$=ethyl, or
$R_2$=carboxy, and $R_1$=ethyl
X=acetic acid
For all examples (27)-(35):
X=ethylcarboxylate

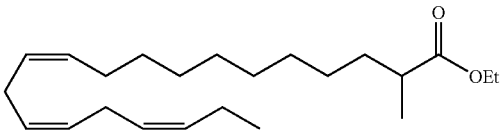 [SMILES: CC/C=C\C/C=C\C/C=C\CCCCCCCCC(C)C(=O)OCC]

Ethyl (all-Z)-2-methyl-11,14,17-eicosatrienoate (27)

$R_1$=methyl, and $R_2$=a hydrogen atom, or
$R_2$=methyl, and $R_1$=a hydrogen atom

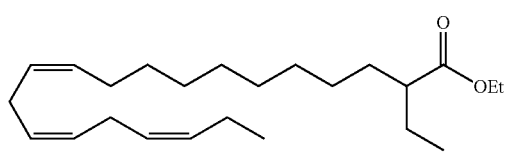 [SMILES: CC/C=C\C/C=C\C/C=C\CCCCCCCCC(CC)C(=O)OCC]

Ethyl (all-Z)-2-ethyl-11,14,17-eicosatrienoate (28)

$R_1$=ethyl, and $R_2$=a hydrogen atom, or
$R_2$=ethyl, and $R_1$=a hydrogen atom

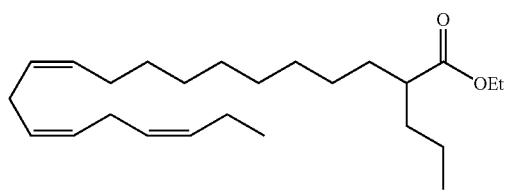 [SMILES: CC/C=C\C/C=C\C/C=C\CCCCCCCCC(CCC)C(=O)OCC]

Ethyl (all-Z)-2-propyl-11,14,17-eicosatrienoate (29)

$R_1$=propyl, and $R_2$=a hydrogen atom, or
$R_2$=propyl, and $R_1$=a hydrogen atom

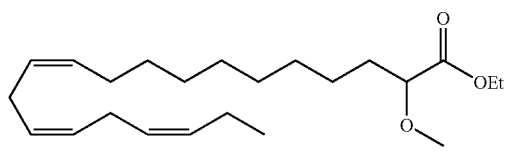 [SMILES: CC/C=C\C/C=C\C/C=C\CCCCCCCCC(OC)C(=O)OCC]

Ethyl (all-Z)-2-methoxy-11,14,17-eicosatrienoate (30)

$R_1$=methoxy, and $R_2$=a hydrogen atom, or
$R_2$=methoxy, and $R_1$=a hydrogen atom

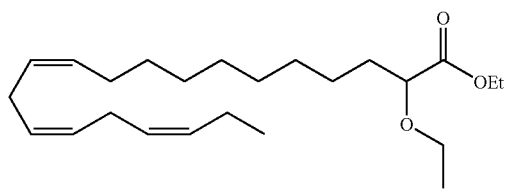 [SMILES: CC/C=C\C/C=C\C/C=C\CCCCCCCCC(OCC)C(=O)OCC]

Ethyl (all-Z)-2-ethoxy-11,14,17-eicosatrienoate (31)

$R_1$=ethoxy, and $R_2$=a hydrogen atom, or
$R_2$=ethoxy, and $R_1$=a hydrogen atom

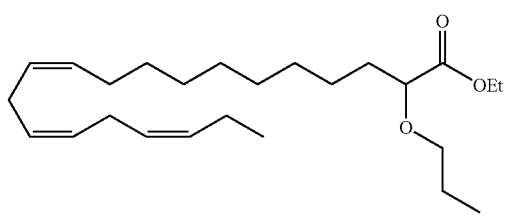 [SMILES: CC/C=C\C/C=C\C/C=C\CCCCCCCCC(OCCC)C(=O)OCC]

Ethyl (all-Z)-2-propoxy-11,14,17-eicosatrienoate (32)

$R_1$=propoxy, and $R_2$=a hydrogen atom, or
$R_2$=propoxy, and $R_1$=a hydrogen atom

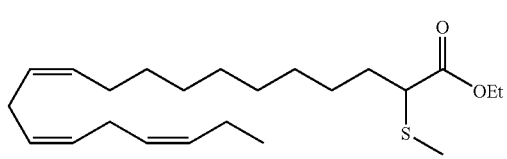

Ethyl (all-Z)-2-thiomethyl-11,14,17-eicosatrienoate (33)

$R_1$=methylthio, and $R_2$=a hydrogen atom, or
$R_2$=methylthio, and $R_1$=a hydrogen atom

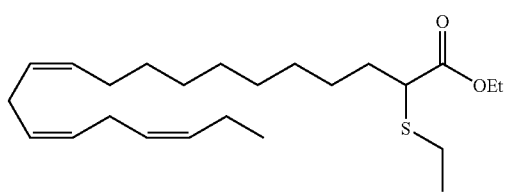

Ethyl (all-Z)-2-thioethyl-11,14,17-eicosatrienoate (34)

$R_1$=ethylthio, and $R_2$=a hydrogen atom, or
$R_2$=ethylthio, and $R_1$=a hydrogen atom

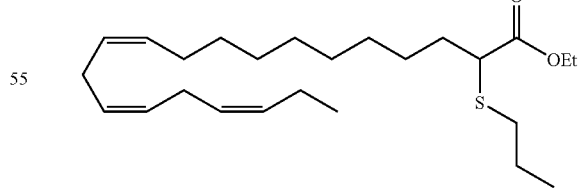

Ethyl (all-Z)-2-thiopropyl-11,14,17-eicosatrienoate (35)

$R_1$=propylthio, and $R_2$=a hydrogen atom, or
$R_2$=propylthio, and $R_1$=a hydrogen atom Category D

EXAMPLES (36)–(44)

For all examples (36)–(44)
Y=C$_{18}$ alkene with 5 double bonds in positions 4, 8, 11, 14, and 17, where the double bonds in position 8, 11, 14 and 17 are in Z-configuration, and the double bond in position 4 is in E configuration.
X=ethylcarboxylate

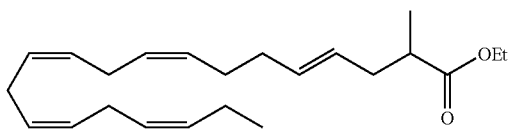 [SMILES: CC/C=C\C/C=C\C/C=C\C/C=C\CC/C=C/CC(C)C(=O)OCC]

Ethyl (4E,8Z,11Z,14Z,17Z)-2-methyl-4,8,11,14,17-eicosapentaenoate (36)

R$_1$=methyl, and R$_2$=a hydrogen atom, or
R$_2$=methyl, and R$_1$=a hydrogen atom

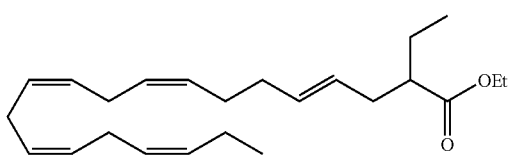

Ethyl (4E,8Z,11Z,14Z,17Z)-2-ethyl-4,8,11,14,17-eicosapentaenoate (37)

R$_1$=ethyl, and R$_2$=a hydrogen atom, or
R$_2$=ethyl, and R$_1$=a hydrogen atom

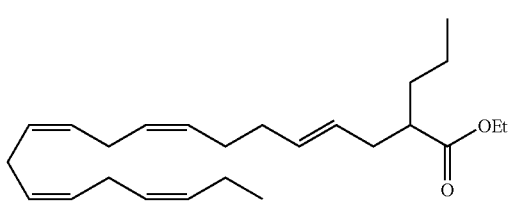 [SMILES: CC/C=C\C/C=C\C/C=C\C/C=C\CC/C=C/CC(CCC)C(=O)OCC]

Ethyl (4E,8Z,11Z,14Z,17Z)-2-propyl-4,8,11,14,17-eicosapentaenoate (38)

R$_1$=propyl, and R$_2$=a hydrogen atom, or
R$_2$=propyl, and R$_1$=a hydrogen atom

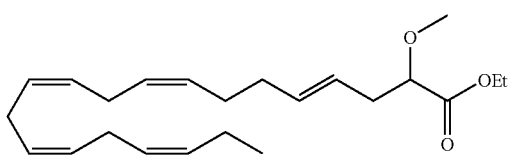

Ethyl (4E,8Z,11Z,14Z,17Z)-2-metoxy-4,8,11,14,17-eicosapentaenoate (39)

R$_1$=methoxy, and R$_2$=a hydrogen atom, or
R$_2$=methoxy, and R$_1$=a hydrogen atom

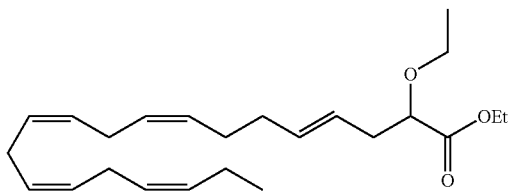 [SMILES: CC/C=C\C/C=C\C/C=C\C/C=C\CC/C=C/CC(OCC)C(=O)OCC]

Ethyl (4E,8Z,11Z,14Z,17Z)-2-etoxy-4,8,11,14,17-eicosapentaenoate (40)

R$_1$=ethoxy, and R$_2$=a hydrogen atom, or
R$_2$=ethoxy, and R$_1$=a hydrogen atom

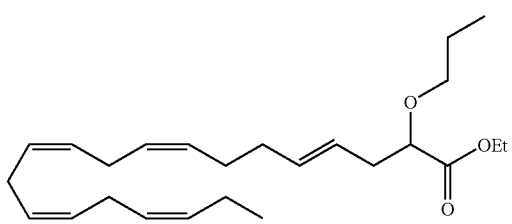

Ethyl (4E,8Z,11Z,14Z,17Z)-2-propoxy-4,8,11,14,17-eicosapentaenoate (41)

R$_1$=propoxy, and R$_2$=a hydrogen atom, or
R$_2$=propoxy, and R$_1$=a hydrogen atom

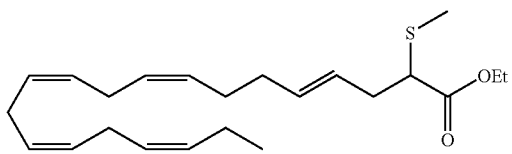

Ethyl (4E,8Z,11Z,14Z,17Z)-2-thiomethyl-4,8,11,14,17-eicosapentaenoate (42)

R$_1$=methylthio, and R$_2$=a hydrogen atom, or
R$_2$=methylthio, and R$_1$=a hydrogen atom

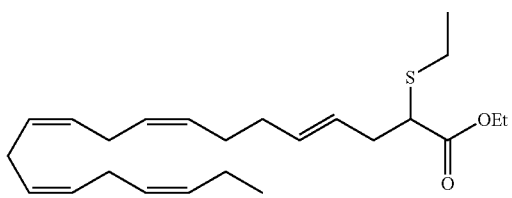

Ethyl (4E,8Z,11Z,14Z,17Z)-2-thioethyl-4,8,11,14,17-eicosapentaenoate (43)

R$_1$=ethylthio, and R$_2$=a hydrogen atom, or
R$_2$=ethylthio, and R$_1$=a hydrogen atom

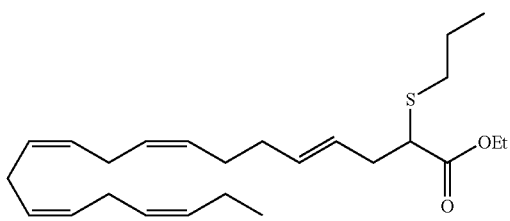 [SMILES: CC/C=C\C/C=C\C/C=C\C/C=C\CC/C=C/CC(OCCC)C(=O)OCC]

Ethyl (4E,8Z,11Z,14Z,17Z)-2-thiopropyl-4,8,11,14,17-eicosapentaenoate (44)

R$_1$=propylthio, and R$_2$=a hydrogen atom, or
R$_2$=propylthio, and R$_1$=a hydrogen atom Category E

EXAMPLES (45)-(50)

For all examples (45)-(50):

X=ethylcarboxylate
Y=C$_{18}$ alkene with 5 double bonds in Z-configuration in positions 5, 8, 11, 14, and 17.

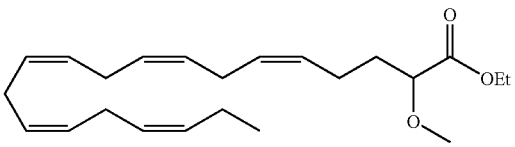 [SMILES: CC/C=C\C/C=C\C/C=C\C/C=C\C/C=C\CCC(OC)C(=O)OCC]

Ethyl (all-Z)-2-methoxy-5,8,11,14,17-eicosapentaenoate (45)

R$_1$=methoxy, and R$_2$=a hydrogen atom, or
R$_2$=methoxy, and R$_1$=a hydrogen atom

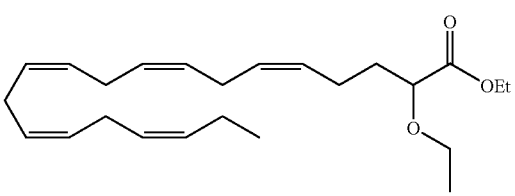 [SMILES: CC/C=C\C/C=C\C/C=C\C/C=C\C/C=C\CCC(OCC)C(=O)OCC]

Ethyl (all-Z)-2-ethoxy-5,8,11,14,17-eicosapentaenoate (46)

R$_1$=ethoxy, and R$_2$=a hydrogen atom, or
R$_2$=ethoxy, and R$_1$=a hydrogen atom

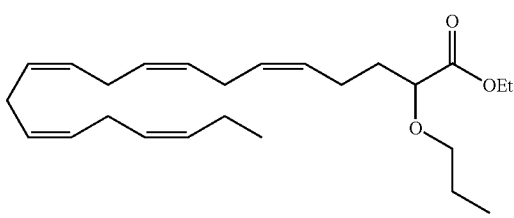 [SMILES: CC/C=C\C/C=C\C/C=C\C/C=C\C/C=C\CCC(OCCC)C(=O)OCC]

Ethyl (all-Z)-2-propoxy-5,8,11,14,17-eicosapentaenoate (47)

R$_1$=propoxy, and R$_2$=a hydrogen atom, or
R$_2$=propoxy, and R$_1$=a hydrogen atom

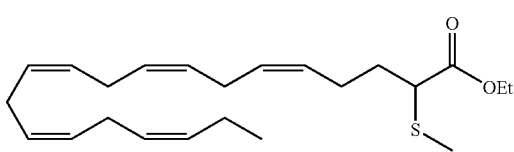

Ethyl (all-Z)-2-thiomethyl-5,8,11,14,17-eicosapentaenoate (48)

R$_1$=methylthio, and R$_2$=a hydrogen atom, or
R$_2$=methylthio, and R$_1$=a hydrogen atom

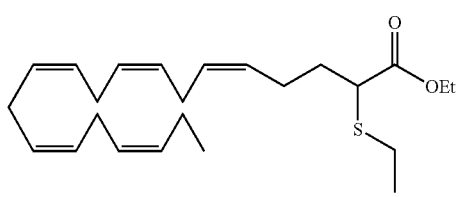 [SMILES: CC/C=C\C/C=C\C/C=C\C/C=C\C/C=C\CCC(SCC)C(=O)OCC]

Ethyl (all-Z)-2-thioethyl-5,8,11,14,17-eicosapentaenoate (49)

R$_1$=ethylthio, and R$_2$=a hydrogen atom, or
R$_2$=ethylthio, and R$_1$=a hydrogen atom

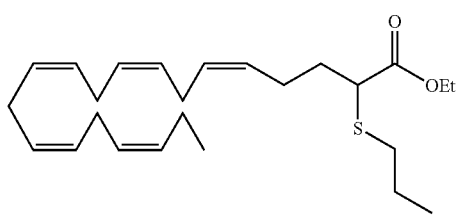 [SMILES: CC/C=C\C/C=C\C/C=C\C/C=C\C/C=C\CCC(SCCC)C(=O)OCC]

Ethyl (all-Z)-2-thiopropyl-5,8,11,14,17-eicosapentaenoate (50)

R$_1$=propylthio, and R$_2$=a hydrogen atom, or
R$_2$=propylthio, and R$_1$=a hydrogen atom

Category F

EXAMPLES (51)-(59)

For all examples (51)-(59):
X=ethylcarboxylate
Y=$C_{20}$ alkene with 6 double bonds in positions 4, 7, 10, 13, 16, and 19, where the double bonds in position 7, 10, 13, 16, and 19 are in Z-configuration, and the double bond in position 4 is in E configuration

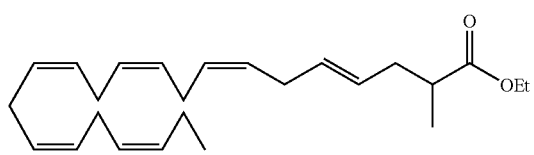

Ethyl 4E,7Z,10Z,13Z,16Z,19Z-2-methyl-4,7,10,13,16,19-docosahexaenoate (51)

$R_1$=methyl, and $R_2$=a hydrogen atom, or
$R_2$=methyl, and $R_1$=a hydrogen atom

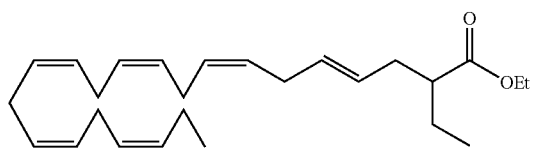 [SMILES: CC/C=C\C/C=C\C/C=C\C/C=C\C/C=C\C/C=C/CC(CC)C(=O)OCC]

Ethyl 4E,7Z,10Z,13Z,16Z,19Z-2-ethyl-4,7,10,13,16,19-docosahexaenoate (52)

$R_1$=ethyl, and $R_2$=a hydrogen atom, or
$R_2$=ethyl, and $R_1$=a hydrogen atom

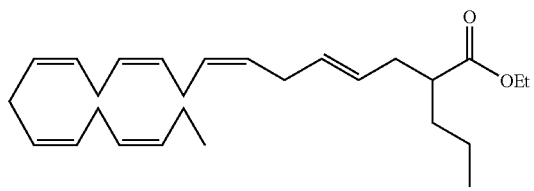 [SMILES: CC/C=C\C/C=C\C/C=C\C/C=C\C/C=C\C/C=C/CC(CCC)C(=O)OCC]

Ethyl 4E,7Z,10Z,13Z,16Z,19Z-2-propyl-4,7,10,13,16,19-docosahexaenoate (53)

$R_1$=propyl, and $R_2$=a hydrogen atom, or
$R_2$=propyl, and $R_1$=a hydrogen atom

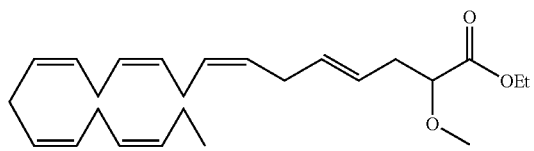

Ethyl 4E,7Z,10Z,13Z,16Z,19Z-2-metoxy-4,7,10,13,16,19-docosahexaenoate (54)

$R_1$=methoxy, and $R_2$=a hydrogen atom, or
$R_2$=methoxy, and $R_1$=a hydrogen atom

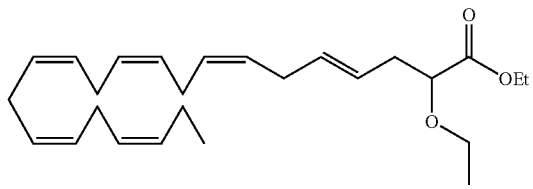 [SMILES: CC/C=C\C/C=C\C/C=C\C/C=C\C/C=C\C/C=C/CC(SCC)C(=O)OCC]

Ethyl 4E,7Z,10Z,13Z,16Z,19Z-2-ethoxy-4,7,10,13,16,19-docosahexaenoate (55)

$R_1$ ethoxy, and $R_2$=a hydrogen atom, or
$R_2$=ethoxy, and $R_1$=a hydrogen atom Ethyl 4E,7Z,10Z,13Z,16Z,19Z-2-propoxy-4,7,10,13,16,19-docosahexaenoate (56)

$R_1$=propoxy, and $R_2$=a hydrogen atom, or
$R_2$=propoxy, and $R_1$=a hydrogen atom Ethyl 4E,7Z,10Z,13Z,16Z,19Z-2-thiomethyl-4,7,10,13,16,19-docosahexaenoate (57)

$R_1$=methylthio, and $R_2$=a hydrogen atom, or
$R_2$=methylthio, and $R_1$=a hydrogen atom Ethyl 4E,7Z,10Z,13Z,16Z,19Z-2-thioethyl-4,7,10,13,16,19-docosahexaenoate (58)

$R_1$=ethylthio, and $R_2$=a hydrogen atom, or
$R_2$=ethylthio, and $R_1$=a hydrogen atom

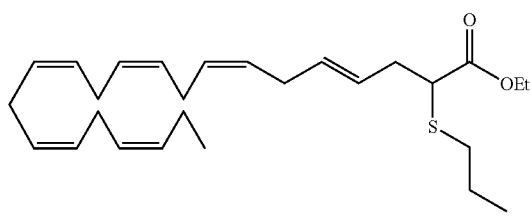 [SMILES: CC/C=C\C/C=C\C/C=C\C/C=C\C/C=C\C/C=C/CC(SCCC)C(=O)OCC]

Ethyl 4E,7Z,10Z,13Z,16Z,19Z-2-thiopropyl-4,7,10,13,16,19-docosahexaenoate (59)

$R_1$=propylthio, and $R_2$=a hydrogen atom, or
$R_2$=propylthio, and $R_1$=a hydrogen atom
Other Examples of Compounds According to the Invention Further preferred compounds include the following compounds/intermediates:

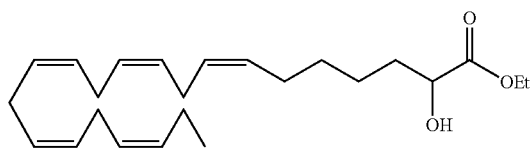 [SMILES: CC/C=C\C/C=C\C/C=C\C/C=C\C/C=C\CCCCC(O)C(=O)OCC]

Ethyl (all-Z)-2-hydroxy-7,10,13,16,19-docosapentaenoate (65)

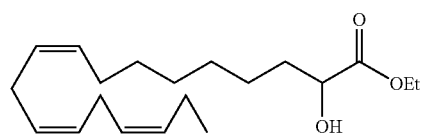

Ethyl (all-Z)-2-hydroxy-9,12,15-octadecatrienoate (61)

The compounds according to the categories A to F may be present as salts, as tri-, di-, and monoglycerides and phospholipids as discussed previously.

It is to be understood that the present invention encompasses any possible pharmaceutically acceptable complexes, solvates or pro-drugs of the omega-3 lipid compounds of formula (I).

"Prodrugs" are entities which may or may not possess pharmacological activity as such, but may be administered (such as orally or parenterally) and thereafter subjected to bioactivation (for example metabolization) in the body to form the agent of the present invention which is pharmacologically active.

A "pharmaceutically active amount" relates to an amount that will lead to the desired pharmacological and/or therapeutic effects, i.e. an amount of the omega-3 lipid compound which is effective to achieve its intended purpose. While individual patient needs may vary, determination of optimal ranges for effective amounts of the omega-3 lipid compound is within the skill of the art, Generally, the dosage regimen for treating a condition with the compounds and/or compositions of this invention is selected in accordance with a variety of factors, including the type, age, weight, sex, diet and medical condition of the patient.

By "a medicament" is meant an omega-3 lipid compound according to formula (I), in any form suitable to be used for a medical purpose, e.g. in the form of a medicinal product, a pharmaceutical preparation or product, a dietary product, a food stuff or a food supplement.

"Treatment" includes any therapeutic application that can benefit a human or non-human mammal. Both human and veterinary treatments are within the scope of the present invention. Treatment may be in respect of an existing condition or it may be prophylactic.

The omega-3 lipid compounds of formula (I) may be used on their own but will generally be administered in the form of a pharmaceutical composition in which the compounds of formula (I) (the active ingredient) are in association with a pharmaceutically acceptable carrier, excipient or diluent (including combinations thereof).

Acceptable carriers, excipients and diluents for therapeutic use are well known in the pharmaceutical art, and can be selected with regard to the intended route of administration and standard pharmaceutical practice. Examples encompass binders, lubricants, suspending agents, coating agents, solubilising agents, preserving agents, wetting agents, emulsifiers, sweeteners, colourants, flavouring agents, odourants, buffers, suspending agents, stabilising agents, and/or salts.

A pharmaceutical composition according to the invention is preferably formulated for oral administration to a human or an animal. The pharmaceutical composition may also be formulated for administration through any other route where the active ingredients may be efficiently absorbed and utilized, e.g. intravenously, subcutaneously, intramuscularly, intranasally, rectally, vaginally or topically.

In a specific embodiment of the invention, the pharmaceutical composition is shaped in form of a capsule, which could also be a microcapsule generating a powder or a sachet. The capsule may be flavoured. This embodiment also includes a capsule wherein both the capsule and the encapsulated composition according to the invention is flavoured. By flavouring the capsule it becomes more attractive to the user. For the above-mentioned therapeutic uses the dosage administered will, of course, vary with the compound employed, the mode of administration, the treatment desired and the disorder indicated.

The pharmaceutical composition may be formulated to provide a daily dosage of e.g. 5 mg to 10 g; 50 mg to 1 g; or 50 mg to 200 g of the omega-3 lipid compound. By a daily dosage is meant the dosage per 24 hours.

The dosage administered will, of course, vary with the compound employed, the mode of administration, the treatment desired and the disorder indicated. Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The omega-3 lipid compound and/or the pharmaceutical composition of the present invention may be administered in accordance with a regimen of from 1 to 10 times per day, such as once or twice per day. For oral and parenteral administration to human patients, the daily dosage level of the agent may be in single or divided doses.

A further aspect of the present invention relates to a lipid composition comprising omega-3 lipid compounds of formula (I). The lipid composition may comprise in the range of 60 to 100% by weight of the omega-3 lipid compounds of formula (I), all percentages by weight being based on the total weight of the lipid composition. For example, at least 60%, at least 70%, at least 80%, or at least 95% by weight of the lipid composition is comprised of omega-3 lipid compounds of formula (I).

The lipid composition may further comprise at least one of the fatty acids (all-Z)-5,8,11,14,17-eicosapentaenoic acid (EPA), (all-Z)-4,7,10,13,16,19-docosahexaenoic acid (DHA), (all-Z)-6,9,12,15,18-heneicosapentaenoic acid (HPA), (all-Z)-7,10,13,16,19-docosapentaenoic acid (DPA, n-3), (all-Z)-8,11,14,17-eicosatetraenoic acid (ETA, n-3), (all-Z)-4,7,10,13,16-Docosapentaenoic acid (DPA, n-6) and/or (all-Z)-5,8,11,14-eicosatetraenoic acid (ARA), or derivatives thereof, i.e. present in their alpha substituted forms.

In specific embodiments of the invention, the lipid composition is a pharmaceutical composition, a nutritional composition or a dietary composition.

The lipid composition may further comprise an effective amount of a pharmaceutically acceptable antioxidant, e.g tocopherol or a mixture of tocopherols, in an amount of up to 4 mg per g, e.g. 0.05 to 0.4 mg per g, of tocopherols, of the total weight of the lipid composition.

The omega-3 compounds and compositions according to the invention are useful for the treatment of a wide range of diseases and conditions, as will be described in more detail below.

There are two major forms of diabetes mellitus. One is type 1 diabetes, which is known as insulin-dependent diabetes mellitus (IDDM), and the other one is type 2 diabetes, which is also known as non-insulin-dependent diabetes mellitus (NIDDM).

Type 2 diabetes is related to obesity/overweight and lack of exercise, often of gradual onset, usually in adults, and caused by reduced insulin sensitivity, so called periferral insulin resistance. This leads to a compensatory increase in insulin production. This stage before developing full fetched type 2 diabetes is called the metabolic syndrome and characterized by hyperinsulinemia, insulin resistance, obesity, glucose intolerance, hypertension, abnormal blood lipids, hypercoagulopathia, dyslipidemia and inflammation. Thus, the present invention provides the use of an omega-3 lipid compound of formula (I) for the manufacturing of a medicament for the treatment and/or prevention of the multi metabolic syndrome termed "metabolic syndrome", and their conditions mentioned above. Later when insulin production seizes, type 2 diabetes mellitus develops. In one embodiment, the compounds according to formula (I) may used for the treatment of type 2 diabetes.

The omega-3 lipid compounds according to formula (I) may also be used for the treatment of other types of diabetes selected from the group consisting of, secondary diabetes, such as pancreatic, extrapancreatic/endocrine or drug-induced diabetes, or exceptional forms of diabetes, such as lipoatrophic, myatonic or a disease caused by disturbance of the insulin receptors.

Suitably, omega-3 lipid compounds of formula (I), as hereinbefore defined, may activate nuclear receptors, preferably PPAR (peroxisome proliferator-activated receptor) α and/or γ.

The omega-3 lipid compounds of formula (I) may also be used for the treatment and/or prevention of obesity. Obesity is usually linked to an increased insulin resistance and obese people run a high risk of developing type 2 diabetes which is a major risk factor for development of cardiovascular diseases. Obesity is a chronic disease that afflict an increasing proportion of the population in Western societies and is associated, not only with a social stigma, but also with decreasing life span and numerous problems, for instance diabetes mellitus, insulin resistance and hypertension. The present invention thus fulfils a long-felt need for a drug that will reduce total body weight, or the amount of adipose tissue, of preferably obese humans, towards their ideal body weight without significant adverse side effects.

Additionally, nonalcoholic fatty liver disease is a common condition associated with metabolic syndrome. More specific fatty liver is primary associated with hypertinsulinemia and insulin-resistance. In one embodiment of the invention an omega-3 lipid compound of formula (I) may act as an insulin-sensitizing agent and reduce liver steatosis.

Moreover, fatty liver disease occurs in two major forms—alcoholic and nonalcoholic. Both terms are marked by accumulation of fat in the liver with variable amounts of liver injury, inflammation, and fibrosis. The spectrum of fatty liver disease ranges from simple steatosis (considered benign and non-progressive), to steatohepatitis (fatty liver with liver cell injury and inflammation), to progressive hepatic fibrosis and cirrhosis. All these conditions are included in the prevention and/or treatment with an omega-3 lipid compound of formula (I) according to the invention.

Furthermore, the omega-3 lipid compounds of formula (I), as hereinbefore defined, are valuable for the treatment and prophylaxis of multiple risk factors known for cardiovascular diseases, such as hypertension, hypertriglyceridemia and high coagulation factor VII phospholipid complex activity. The omega-3 lipid compounds of formula (I) may be used for the treatment of elevated blood lipids in humans, acting as an lipid lowering or decreasing drug.

The present invention also provides the use of an omega-3 lipid compound of formula (I) for the manufacture of a medicament for lowering triglycerides in the blood of mammals and/or evelating the HDL cholesterol levels in the serum of a human patients.

In a further aspect, the present invention relates to the use of an omega-3 lipid compound according to formula (I) for the manufacture of a medicament or pharmaceutical for the treatment and/or the prevention of at least one of; atherosclerosis or IgA Nephropathy, prophylaxis of multiple risk factors for cardiovascular diseases, heart failure, atrial fibrillation and/or a post-myocardial infarct, stroke, cerebral or transient ischaemic attacks related to atherosclerosis of several arteries, treatment of TBC or HIV, and treatment of HTG in HIV patients.

α/γ and/or α/δ, preferably a PPAR α/γ activator or modulator. The present invention also includes the case than a compound of formula (I) is a PPAR pan-agonists (i.e. an alpha, beta and gamma agonists).

Methods for Preparing the Compounds According to the Invention

The omega-3 lipid compound of formula (I) where $R_1$ (or $R_2$) is a hydrogen may be prepared through the following processes (Scheme 1). Omega-3 lipid compounds represented by the general formula (I) where $R_1$ is a hydrogen and $R_2$ denotes a $C_1$-$C_6$ alkyl group, a benzyl, a halogen, a benzyl, an alkenyl, an alkynyl are prepared by reacting a long chain polyunsaturated ester with a strong non-nucleophilic base like lithium diisopropylamine, potassium/sodium hexamethyldisilazide or KH/NaH in DMF in a solvent such as tetrahydrofuran, diethylether at temperatures of −60 to −78° C., to provide the ester enolate (process 1).

Method I

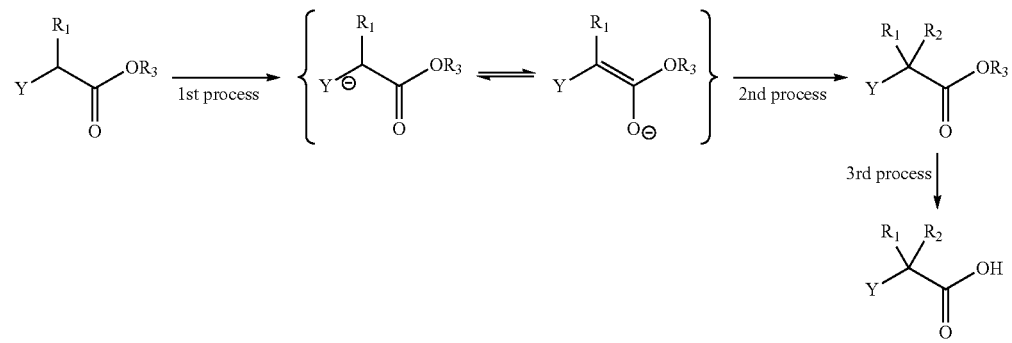

$R_3$ = alkyl group (methyl, ethyl, propyl)

In one embodiment, the present invention also provides the use of an omega-3 lipid compound according to formula (I) for the manufacture of a medicament or pharmaceutical for the treatment and/or the prevention of psoriasis, multiple sclerosis and/or rheumatoid arthrit.

Omega-3 lipid compounds of formula (I), or compositions including omega-3 lipid compounds of formula (I), is a least one of a human peroxisome proliferant-activated receptor (PPAR) α, γ and/or δ activator or modulator. As previously known, the PPARα receptor is more promiscuous compared to PPARγ, meaning that PPARα will accept a greater variety of fatty acids as ligands compared to PPARγ. However, since patients with metabolic syndrome or type 2 diabetes are usually obese or overweight and have pathologic blood lipids, mainly elevated triglycerides and low High-Density Cholesterol (HDL-chol) activation of the PPARα receptor is important. Therefore, in a more specific embodiment of the invention, the compound of formula (I) is a selective human peroxisome proliferant-activated receptor (PPAR) α activator or modulator. Moreover, an ideal drug for treatment of metabolic syndrome or type 2 diabetes may act as ligand to both these receptors. Thus, the present invention provides the use of a compound of formula (I) as a dual human peroxisome proliferant-activated receptor (PPAR) activator or modulator, This ester enolate is reacted with an electrophilic reagent like an alkylhalide exemplified by ethyliodine, benzylcloride, an acyl halide exemplified by; acetyl chloride, benzoyl bromide, a carboxylic anhydride exemplified by acetic anhydride or a electrophilic halogenation reagent exemplified by N-fluorobenzene sulfonimide (NFSI), N-bromosuccinimide or iodine etc. to provide the substituted derivative (process 2). The 2-halo substituted derivatives can be reacted with a nucleophilic reagent such as tiols to provide 2-alkylthio-derivatives.

The ester is further hydrolysed in a solvent like ethanol or methanol to the carboxylic acid derivative by addition of a base like lithium/sodium/potassium hydroxide in water at temperatures between 15° C. and reflux.

Claisen condensation of the long chain polyunsaturated ester occurs during the treatment of ester with a strong base. (This condensation product might possess interesting biologically activity. Thus, in one embodiment of the invention the condensation (intermediate) product mentioned above, as well as the use of this product for treatment and/or prevention of diseases according to the present invention, are disclosed.)

Moreover, in a further embodiment, compounds represented by the general formula (I) are synthesised through following processes (Scheme 2).

Method II:

Scheme 2:

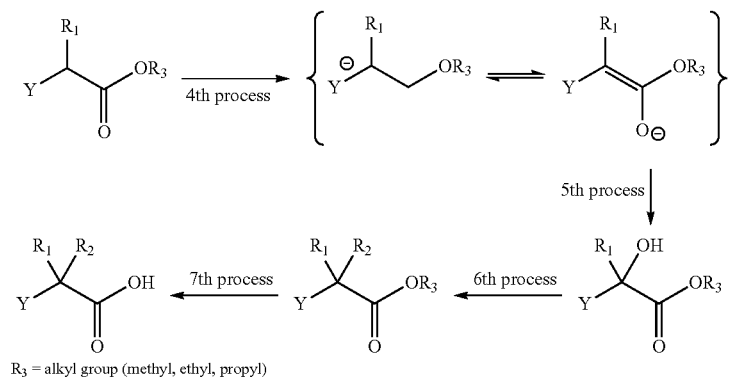

R₃ = alkyl group (methyl, ethyl, propyl)

Compounds represented by the general formula (I) where $R_1$ is a hydrogen and $R_2$ denotes a hydroxy, an alkoxy group, an acyloxy are prepared by reacting a long chain polyunsaturated ester with a strong non-nucleophilic base like lithium diisopropylamine or potassium/sodium hexamethyldisilazide in a solvent such as tetrahydrofuran, diethylether at temperatures of −60 to −78° C., to provide the ester enolate (process 4). This ester enolate is reacted with an oxygen source like dimethyldioxirane, 2-(phenylsulfonyl)-3-phenyloxaziridine, molecular oxygen with different additives like trimethylphosphite or different catalysts like a Ni(II) complex to provide alpha-hydroxy ester (process 5). Reaction of the secondary alcohol with a base like sodiumhydride in a solvent like THF or DMF generates an alkoxide that is reacted with different electrophilic reagents as alkyliodide for example; methyl iodide, ethyl iodide, benzylbromide or an acyl halide, for example; acetyl chloride, benzoyl bromide (process 6). The ester is hydrolysed in a solvent like ethanol or methanol to the carboxylic acid derivative by addition of a base like lithium/sodium/potassium hydroxide in water at temperatures between 15° C. to reflux (process 7).

The alpha-hydroxy ester is a useful intermediate for the introduction of other functional groups in the α-position according to the invention. The hydroxyl function can be activated by conversion to a halide or tosylate prior to reaction with different nucleophiles like ammonia, amines, thiols, etc. The Mitsunobu reaction is also useful for the conversion of a hydroxylgroup into other functional groups. (Mitsunobu, O, Synthesis, 1981, 1).

Compounds represented by the general formula (I) where $R_1$ is a hydrogen and $R_2$ denotes an alkyl, phenyl, hydroxymethyl, carboxyl, alkoxycarbonyl, hydroxymethyl, hydroxy, an alkoxy group, an acyloxy can be prepared by reacting a long chain polyunsaturated tosylate, mesylate or halide with dialkylmalonate or substituted dialkyl malonates. Method III, scheme 3. Hydrolysis of the diester and decarboxylation gives alpha-substituted products.

Method III

Scheme 3

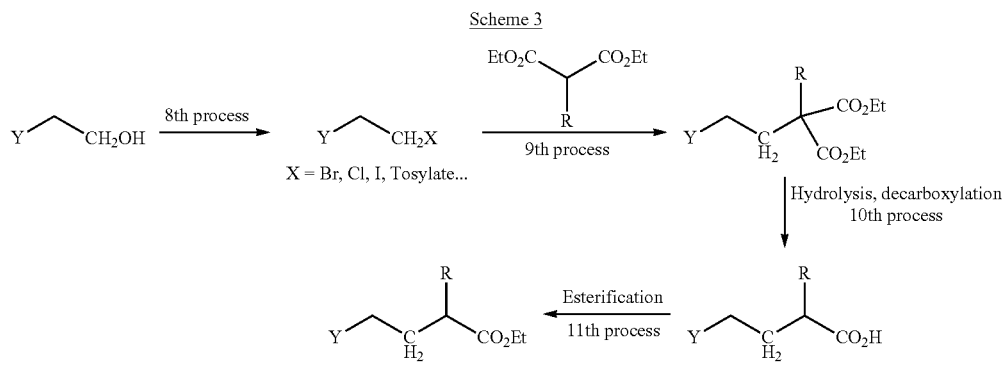

The long chain polyunsaturated tosylates used in method III can be prepared from the corresponding long chain polyunsaturated alcohol. These alcohols may be prepared directly from the carboxylic esters of the naturally occurring unsaturated fatty acids; alpha-linolenic acid, conjugated linoleic acid, eicosapentaenoic acid, etc. by reduction with a reducing agent like lithium aluminiumhydride or diisobultylaluminiumhydride at −10 to 0° C. Using the alcohol derived from ethyl(all-Z)-5,8,11,14,17-eicosapentaenoate in the reaction sequence described in method III, 2-substituted DPA derivatives will be prepared. The alcohols can also be prepared by degradation of the polyunsaturated fatty acids EPA and DHA as described by Holmeide et al. (*J. Chem. Soc., Perkin Trans. 1*, 2000, 2271). In this case one can start with purified EPA or DHA, but it is also possible to start with fish oil containing EPA and DHA in mixture. The reason for this is that DHA reacts faster in an iodolactonisation reaction than EPA to form an iodo δ-lactone (Corey et al, *Proc. Natl. Acad. Sci. USA*, 1983, 3581, Wright et al, *J. Org. Chem.*, 1987, 4399), Kuklev et al, *Phytochemistry*, 1992, 2401). (all-Z)-3,6,9,12,15-octadecapentaenol can be prepared from DHA by this literature method. Using this alcohol as a reagent in methods III will afford 2-substituted EPA derivatives.

Combining method III with method I can give disubstituted derivatives.

Method IV.

The compounds of formula (I) wherein X is a carboxylic acid and in the form of a phospholipid can be prepared through the following processes.

reaction of the fatty acid (2 equivalents) with glycerol (1 equivalent) in the presence of 1,3-dicyclohexylcarbondiimide (DCC) and 4-dimethylaminopyridine (DMAP).

The compounds of formula (I) wherein X is a carboxylic acid and in the form of a monoglyceride can be prepared through the following processes. Acylation of 1,2-O-isopropylidene-sn-glycerol with a fatty acid using DCC and DMAP in chloroform gives a monodienoylglycerol. Deprotection of the isopropylidene group can be done by treating the protected glycerol with an acidic (HCl, acetic acid etc.) (O'Brian, *J Org. Chem.*, 1996, 5914).

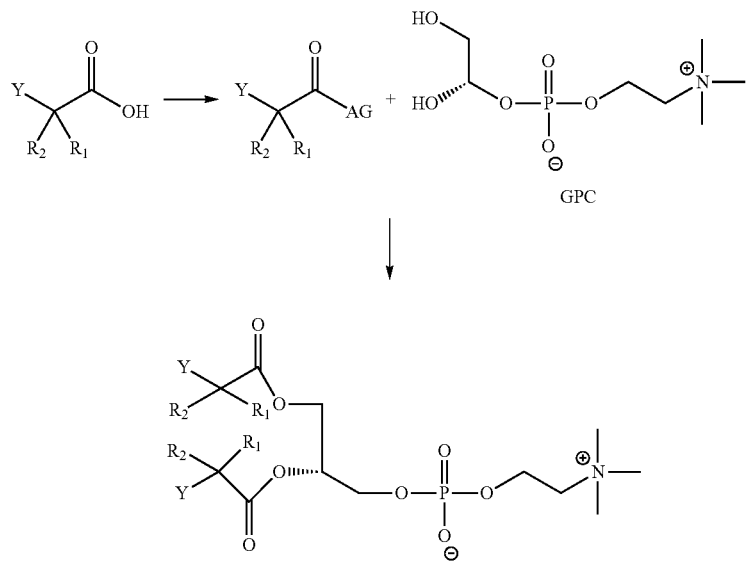

Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent (Hermetter; *Chemistry and Physics of lipids*, 1981, 28, 111). Sn-Glycero-3-phosphocholine, as cadmium (II) adduct can also be reacted with the imidazolide activated fatty acid in the presence of DBU (1,8-diazabicyclo[5.4.0]undec-7-ene] to prepare the phosphatidylcholine of the respective fatty acid (International application number PCT/GB2003/002582). Enzymatic transphosphatidylation can effect the transformation of phosphstidylcholine to phosphatidyletanolamine (Wang et al, *J. Am. Chem. Soc.*, 1993, 115, 10487).

Polyunsaturated containing phospholipids may be prepared by various ways, mainly by chemical synthesis of phospholipids as described, by enzymatic esterification and trans-esterification of phospholipids or enzymatic transphosphatidylation of phospholipids. (Hosokawa, *J. Am. Oil Chem. Soc.* 1995, 1287, Lilja-Hallberg, Biocatalysis, 1994, 195). For such enzymatic applications a preferred embodiment of the invention is a compound according to formula I wherein $R_1$ or $R_2$ are hydrogen.

The compounds of formula (I) wherein X is a carboxylic acid and in the form of a triglyceride can be prepared through the following processes. Excess of the novel fatty acid can be coupled to glycerol using dimethylaminopyridine (DMAP) and 2-(1H-benzotriazol-1-yl)-N,N,N',N'-tetramethyluroniumhexafluorophosphate (HBTU).

The compounds of formula (I) wherein X is a carboxylic acid and in the form of a diglyceride can be prepared by

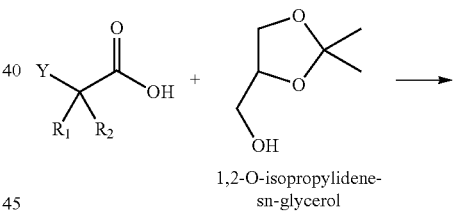

1,2-O-isopropylidene-sn-glycerol

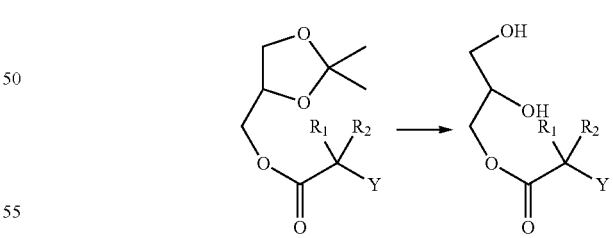

There are several common synthetic methods for the preparation of monoglycerides with the fatty acid in 2-position. One method utilizes esterification of the fatty acid with glycidol in the presence of 1-(3-dimethylaminopropyl)-3-ethylcarbodiimidehydrochloride (EDC) and 4-dimethylaminopyridine (DMAP) to produce a glycidyl derivative. Treatment of the glycidyl derivative with trifluoroacetic anhydride (TFAA) prior to trans-esterification the monoglyceride is obtained (Parkkari et al, *Bioorg. Med. Chem. Lett.* 2006, 2437).

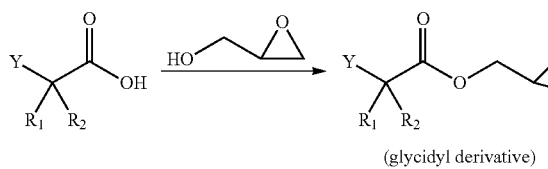

(glycidyl derivative)

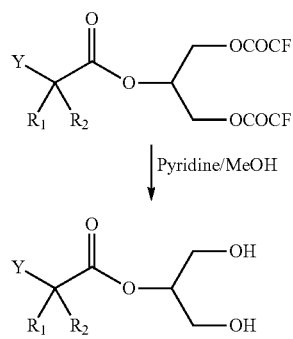

Further common methods for the preparation of mono-, di- and tri-glycerides of fatty acid derivatives are described in international patent application, PCT/FR02/02831.

It is also possible to use enzymatic processes (lipase reactions) for the transformation of a fatty acid to a mono-, di-, tri-glyceride. A 1,3-regiospecific lipase from the fungus *Mucor miehei* can be used to produce triglycerides or diglycerides from polyunsaturated fatty acids and glycerol. A different lipase, the non-regiospecific yeast lipase from *Candida antartica* is highly efficient in generating triglycerides from polyunsaturated fatty acids (Haraldsson, *Pharmazie*, 2000, 3). For this enzymatic application a preferred embodiment of the invention is a compound according to formula I wherein $R_1$ and $R_2$ are hydrogen.

Synthesis Protocols

The invention will now be described in more detail by the following examples, which are not to be constructed as limiting the invention. In the following examples the structures were verified by NMR and by Mass Spectrometry (MS). The NMR spectra were recorded in $CDCl_3$. J values are given in Hz.

Ethyl (all-Z)-2-ethyl-7,10,13,16,19-docosapentaenoate (14)

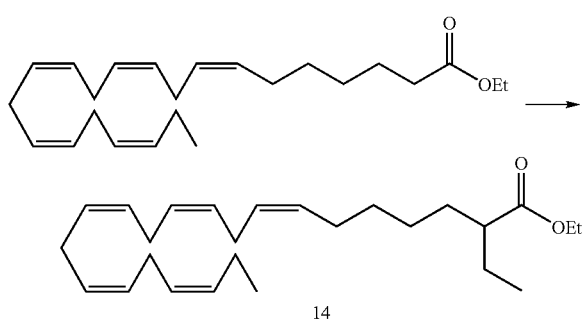

Butyllithium (0.96 ml, 1.54 mmol, 1.6 M in hexane) was added dropwise to a stirred solution of diisopropylamine (0.23 ml, 1.60 mmol) in dry THF (5 ml) under $N_2$ at 0° C. The resulting solution was stirred at 0° C. for 20 min., cooled to −78° C. and stirred an additional 10 min. before dropwise addition of ethyl (all-Z)-7,10,13,16,19-docosapentaenoate (0.50 g, 1.40 mmol) in dry THF (5 mL) during 10 min. The green solution was stirred at −78° C. for 10 min. before ethyl iodide (0.16 ml, 2.09 mmol) was added. The resulting solution was allowed to reach ambient temperature over one hour, portioned between water (10 mL) and heptane (10 mL). The aqueous layer was extracted with heptane (20 mL) and the combined organic layer was washed with 1M HCl and dried ($Na_2SO_4$). Concentration under reduced pressure and purification by flash chromatography (Heptane:EtOAc 98:2) afforded 0.37 g (68%) of the title compound 14 as a colorless oil.

$^1$H-NMR (200 MHz, $CDCl_3$): δ 0.83-0.99 (m, 6H), 1.20-1.60 (m, 111H), 2.05 (m, 4H), 2.19 (m, 1H), 2.81 (m, 8H), 4.11 (q, 2H), 5.35 (m, 10H);

$^{13}$C-NMR (50 MHz, $CDCl_3$): δ 11.72, 14.18, 14.28, 20.47, 25.43, 25.45, 25.54, 26.99, 29.45, 30.22, 31.91, 37.70, 47.19, 59.82, 85.73, 126.94, 127.72, 127.79, 127.85, 128.05, 128.09, 128.36, 128.44, 129.97, 176.17;

MS (electrospray): 409.3 [M+Na].

Ethyl (all-Z)-2-hydroxy-7,10,13,16,19-docosapentaenoate (65)

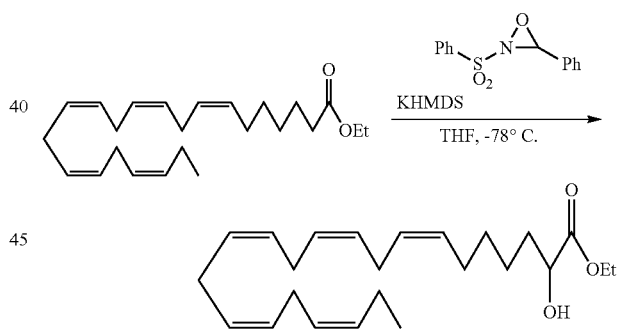

A solution of KHMDS (533.9 mg, 2.68 mmol) in THF, 10 mL, was cooled to −78° C. under $N_2$-atmosphere before a solution of (all-Z)-7,10,13,16,19-docosapentaenoate (478.8 mg, 1.33 mmol) in THF, 2.5 mL, was added drop wise. The mixture was stirred at −78° C. for 30 minutes before a solution of trans-2-phenylsulfonyl)-3-phenyloxaziridine (Davis' reagent) (525.3 mg, 2.01 mmol) in THF, 1.5 mL, was added drop wise. The reaction mixture was stirred at −78° C. for 1 hr 50 minutes before it was quenched with $NH_4Cl$ sat, 20 mL, after warming to room temperature the mixture was extracted with diethyl ether, 50 mL×2, the organic phase was washed with brine, 20 mL, dried ($Na_2SO_4$), filtered and evaporated in vacuo. The resulting crude product was subjected to flash chromatography on silica gel eluting with heptane/EtOAc (100:1)-(95:5) yielding 293 mg (59%) of the product 65 as a colorless liquid.

¹H NMR (200 MHz, CDCl₃) δ 0.95 (t, J=7.5 Hz, 3H), 1.28 (t, J=7.1 Hz, 3H), 1.38-1.46 (m, 4H), 1.49-1.81 (m, 2H), 2.02-2.13 (m, 4H), 2.76-2.85 (m, 9H), 4.12 (dd, J=2.5, 6.9 Hz, 1H), 4.22 (q, J=7.1 Hz, 2H), 5.32-5.41 (m, 10H)
¹³C NMR (50 MHz, CDCl₃) δ 14.1, 14.2, 20.4, 24.4, 25.5, 25.6, 27.0, 29.3, 34.3, 61.5, 70.3, 127.0, 127.8, 127.87, 127.92, 128.08, 128.15, 128.4, 128.5, 129.9, 132.0, 175.3 (2 signals hidden)
MS (electrospray); 397 [M+Na]⁺

Ethyl (all-Z)-2-ethoxy-7,10,13,16,19-docosapentaenoate (17)

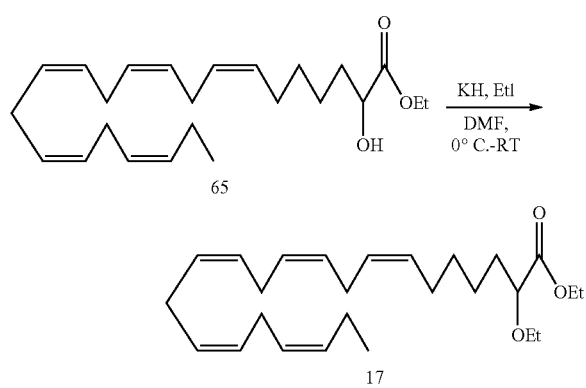

A suspension of 35% KH (92.4 mg, 0.806 mmol KH) in DMF, 3 mL, was cooled under N₂-atmosphere to 0° C. and a solution of ethyl (all-Z)-2-hydroxy-7,10,13,16,19-docosapentaenoate (65) (101 mg, 0.27 mmol) in DMF, 2 mL, was added drop wise. The mixture was stirred for 30 minutes at 0° C. before EtI (0.22 mL, 2.73 mmol) was added. The mixture was then allowed to slowly reach room temperature and stirred for 4 hrs. The reaction was quenched with NH₄Cl sat., 20 mL, and extracted with diethyl ether, 50 mL×2. The organic phase was washed with brine, 20 mL, dried (Na₂SO₄), filtered and evaporated in vacuo and subjected to flash chromatography on silica gel eluting with heptane:EtOAc (100:1)-(95:5) yielding 19.4 mg (18%) of the product 17 as a colorless liquid.

¹H NMR (300 MHz, CDCl₃) δ 0.95 (t, J=7.5 Hz, 3H), 1.20 (t, J=7.0 Hz, 3H), 1.26 (t, J=7.1 Hz, 3H), 1.31-1.47 (m, 5H), 1.66-1.72 (m, 2H), 2.03-2.11 (m, 5H), 2.77-2.84 (m, 6H), 3.33-3.47 (m, 1H), 3.55-3.65 (m, 1H), 3.78 (t, J=6.4 Hz, 1H), 4.14-4.22 (m, 2H), 5.27-5.39 (m, 10H)
¹³C NMR (75 MHz, CDCl₃) δ 14.3, 15.2, 20.6, 25.0, 25.5, 25.6 (2 signals), 27.0, 29.3, 32.9, 60.6, 65.9, 79.0, 127.0, 127.9 (2 signals), 128.0, 128.1, 128.2, 128.4, 128.5, 130.0, 132.0, 173.2 (2 signals hidden)
MS (electrospray); 425 [M+Na]⁺

(all-Z)-2-ethoxy-7,10,13,16,19-docosapentaenoic acid (69)

-continued

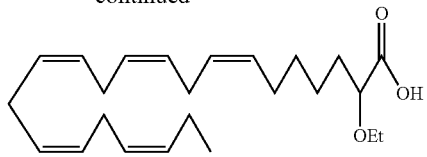

To a solution of Ethyl (all-Z)-2-ethoxy-7,10,13,16,19-docosapentaenoate (17) (66.1 mg, 0.164 mmol) in EtOH (5 ml) was added a solution of LiOH.H₂O (57.7 mg, 1.38 mmol) in water (5 ml). The reaction mixture was stirred under N₂-atmosphere at 80° C. for 19½ hrs. After cooling 1 M HCl was added (to pH ~1). The resulting mixture was extracted with diethyl ether (50 ml), dried (MgSO₄) and evaporated in vacuo yielding 55 mg (90%) of the title compound as a light yellow oil.

¹H NMR (200 MHz, CDCl₃) δ 0.95 (t, J=7.5 Hz, 3H), 1.24 (t, J=7.0 Hz, 3H), 1.38-1.41 (m, 4H), 1.75-1.85 (m, 2H), 2.03-2.13 (m, 4H), 2.80-2.83 (m, 8H), 3.46-3.71 (m, 2H), 3.88 (t, J=5.8 Hz, 1H), 5.23-5.44 (m, 10H)
MS (electrospray); 373 [M−H]⁻

Ethyl (all-Z)-2-ethyl-9,12,15-octadecatrienoate (2)

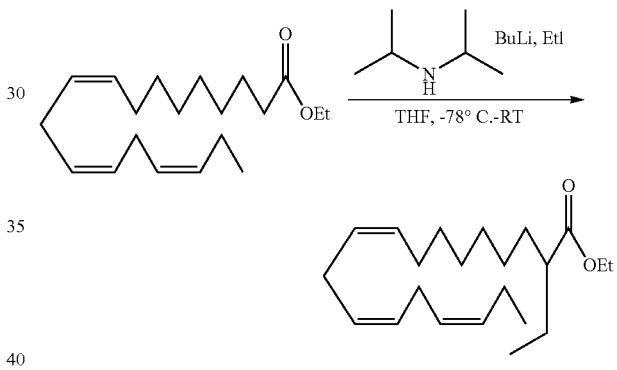

To a solution of diisopropyl amine (265 μL, 1.88 mmol) in dry THF, 5 mL, under N₂-atmosphere at 0° C. was added drop wise 1.6 M BuLi in hexane (1.15 mL, 1.84 mmol). The resulting mixture was stirred at −78° C. for 20 minutes before a solution of ethyl (all-Z)-9,12,15-octadecatrienoate (502 mg, 1.64 mmol) in THF, 5 mL, was added drop wise. The resulting reaction mixture was stirred for 30 minutes at −78° C. before EtI (0.20 mL, 2.48 mmol) was added drop wise. The ice bath was removed an the reaction mixture was stirred for 3 hrs and 45 minutes before it was quenched with water, 25 mL, and extracted with diethyl ether, 50 mL×2. The organic phase was washed with 1 M HCl (aq), 20 mL, dried (Na₂SO₄), filtered and evaporated in vacuo. The resulting crude product was subjected to flash chromatography on silica gel eluting with heptane/EtOAc (100:1) yielding 216 mg (39%) of ethyl (all-Z)-2-ethyl-9,12,15-octadecatrienoate (2) as a colorless liquid.

¹H NMR (200 MHz, CDCl₃) δ 0.84 (t, J=7.4 Hz, 3H), 0.93 (t, J=7.5 Hz, 3H), 1.21 (t, J=7.1 Hz, 3H), 1.25 (m, 8H), 1.33-1.65 (m, 4H), 2.02 (q, J=7.0 Hz, 4H), 2.13-2.27 (m, 1H), 2.76 (t, J=5.6 Hz, 4H), 4.10 (q, J=7.1 Hz, 2H), 5.20-5.41 (m, 6H)
¹³C NMR (50 MHz, CDCl₃) δ 11.7, 14.2, 14.3, 20.5, 25.4, 25.5, 27.1, 27.3, 29.0, 29.4, 29.5, 32.0, 47.2, 59.8, 127.0, 127.6, 128.1, 130.1, 131.8, 176.2 (2 signals hidden)
MS (electrospray); 357 [M+Na]⁺

(all-Z)-2-ethyl-9,12,15-octadecatrienoic acid (70)

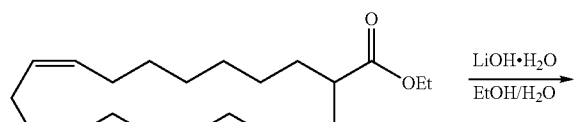

To a solution of ethyl (all-Z)-2-ethyl-9,12,15-octadecatrienoate (2) (111 mg, 0.312 mmol) in EtOH (10 ml) was added a solution of LiOH.H$_2$O (108 mg, 2.57 mmol) in water (10 ml). The reaction mixture was stirred under N$_2$-atmosphere at 80° C. for 15 hrs. After cooling 1 M HCl was adde (to pH ~2). The resulting mixture was extracted with diethyl ether (50 ml), dried (MgSO$_4$) and evaporated in vacuo yielding 81 mg (79%) of the title compound as a yellow oil.

$^1$H NMR (200 MHz, CDCl$_3$) δ 0.83-0.99 (m, 6H), 1.20-1.29 (m, 8H), 1.41-1.78 (m, 4H), 1.99-2.13 (m, 4H), 2.21-2.30 (m, 1H), 2.76-2.82 (m, 4H), 5.23-5.44 (m, 6H)

MS (electrospray); 305 [M−H]$^−$

Ethyl (all-Z)-2-iodo-9,12,15-octadecatrienoate (60)

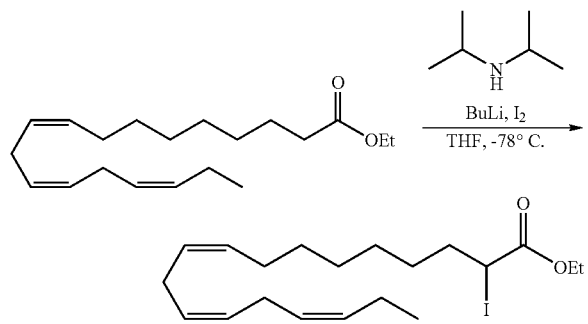

To a solution of diisopropyl amine (322 μL, 2.28 mmol) in dry THF, 5 mL, under N$_2$-atmosphere at 0° C. was added drop wise 1.6 M BuLi in hexane (1.25 mL, 2.0 mmol). The resulting mixture was stirred at −78° C. for 20 minutes before a solution of ethyl (all-Z)-9,12,15-octadecatrienoate (501 mg, 1.63 mmol) in THF, 5 mL, was added drop wise. The resulting yellow reaction mixture was stirred for 35 minutes at −78° C. before a solution of I$_2$ (704 mg, 2.77 mmol) in THF, 5 mL was added drop wise. The reaction mixture was stirred at −78° C. for 25 minutes before it was quenched with 1 M HCl, 20 mL, and extracted with heptane, 50 mL. The organic phase was washed with 10% Na$_2$S$_2$O$_3$(aq), 25 mL, dried (Na$_2$SO$_4$), filtered and evaporated in vacuo. The resulting crude product was subjected to flash chromatography on silica gel eluting with heptane/EtOAc (100:1) yielding 152 mg (22%) of ethyl (all-Z)-2-iodo-9,12,15-octadecatrienoate (60) as a colorless liquid.

$^1$H NMR (200 MHz, CDCl$_3$) δ 0.95 (t, J=7.5 Hz, 3H), 1.25 (t, J=7.1 Hz, 3H), 1.30 (m, 8H), 1.89-2.09 (m, 6 H), 2.78 (t, J=5.5 Hz, 4H), 4.13-4.28 (m, 3H), 5.25-5. (m, 6 H)

$^{13}$C NMR (50 MHz, CDCl$_3$) δ 13.7, 14.2, 20.5, 21.4, 25.5, 25.6, 27.1, 28.5, 28.9, 26.3, 29.4, 36.0, 61.6, 127.0, 127.8, 128.2, 128.3, 130.1, 131.9, 171.4

MS (electrospray); 455 [M+Na]$^+$

Ethyl (all-Z)-2-thiomethyl-9,12,15-octadecatrienoate (7)

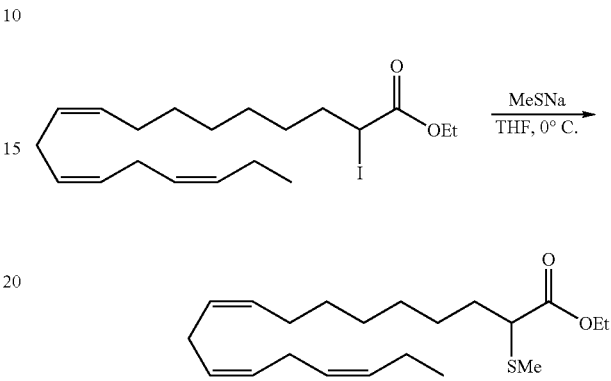

Ethyl (all-Z)-2-iodo-9,12,15-octadecatrienoate (60) (146 mg, 0.338 mmol) was dissolved in THF, 5 mL, and cooled to 0° C. under N$_2$-atmosphere before MeSNa was added. The reaction mixture was stirred at 0° C. for 1 hr before it was diluted with heptane, 50 mL, washed with water, 2×20 mL, dried (Na$_2$SO$_4$), filtered and evaporated in vacuo. The resulting crude product was subjected to flash chromatography on silica gel eluting with heptane/EtOAc (100:1)-(95:5) yielding 110 mg (92%) of ethyl (all-Z)-2-thiomethyl-9,12,15-octadecatrienoate (7) as a colorless liquid.

$^1$H NMR (200 MHz, CDCl$_3$) δ 0.94 (t, J=7.5 Hz, 3H), 1.23 (t, J=7.1 Hz, 3H), 1.29 (m, 8H), (m, 1H), (m, 1H), 2.09 (s, 3H), 1.97-2.13 (m, 8H), 2.77 (t, J=5.6 Hz, 4H), 3.12 (dd, J=6.8, 8.3 Hz, 1H), 4.17 (q, J=7.1 Hz, 2H), 5.26-5.37 (m, 6H)

$^{13}$C NMR (50 MHz, CDCl$_3$) δ 13.7, 14.2, 20.5, 25.5, 25.6, 27.1, 27.2, 28.97, 29.04, 29.4, 30.6, 47.3, 60.9, 127.1, 127.7, 128.17, 128.23, 130.1, 131.9, 172.4 (1 signal hidden)

MS (electrospray); 375 [M+Na]$^+$

Ethyl (all-Z)-2-hydroxy-9,12,15-octadecatrienoate (61)

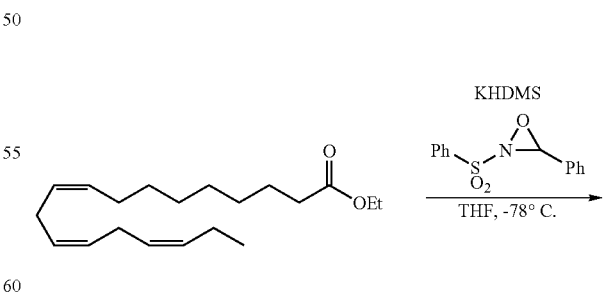

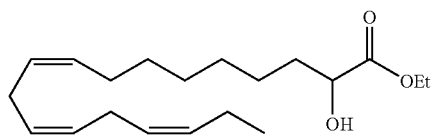

A solution of KHMDS (5.24 g, 26.2 mmol) in THF, 100 mL, was cooled to −78° C. under N$_2$-atmosphere before a solution of ethyl (all-Z)-9,12,15-octadecatrienoate (4.01 g, 13.1 mmol) in THF, 25 mL, was added drop wise. The mixture was stirred at −78° C. for 30 minutes before a solution of trans-2-phenylsulfonyl)-3-phenyloxaziridine (Davis' reagent) (5.13 g, 19.6 mmol) in THF, 15 mL, was added drop wise. The reaction mixture was stirred at −78° C. for 1½ hrs. before it was quenched with NH$_4$Cl sat, 30 mL, after warming to room temperature the mixture was extracted with diethyl ether, 100 mL×2, the organic phase was washed with brine, 30 mL, dried (Na$_2$SO$_4$), filtered and evaporated in vacuo. The resulting crude product was subjected to flash chromatography on silica gel eluting with heptane/EtOAc (100:1)-(95:5) yielding 2.67 g (63%) of ethyl (all-Z)-2-hydroxy-9,12,15-octadecatrienoate (61) as a colorless liquid.

$^1$H NMR (200 MHz, CDCl$_3$) δ 0.92 (t, J=7.5 Hz, 3H), 1.24 (t, J=7.1 Hz, 3H), 1.28 (m, 8H), 1.53-1.75 (m, 2H), 1.96-2.10 (m, 4H), 2.76 (t, J=5.6 Hz, 5H), 4.11 (dd, J=4.0, 6.7 Hz, 1H), 4.19 (q, J=7.1 Hz, 2H), 5.22-5.41 (m, 6H)

$^{13}$C NMR (50 MHz, CDCl$_3$) δ 14.09, 14.14, 20.4, 24.6, 25.4, 25.5, 27.1, 29.0, 29.1, 29.4, 34.3, 61.4, 70.3, 127.0, 127.7, 128.11, 128.14, 130.1, 131.8, 175.3

MS (electrospray); 345 [M+Na]$^+$

Ethyl (all-Z)-2-ethoxy-9,12,15-octadecatrienoate (5)

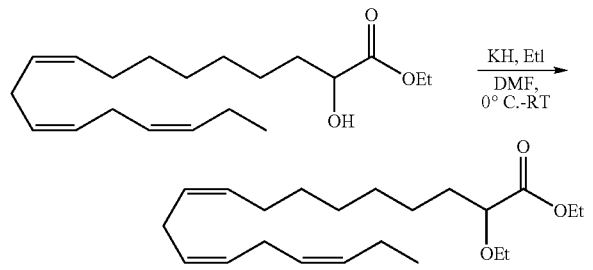

A suspension of 35% KH (84.3 mg, 0.735 mmol KH) in DMF, 2 mL, was cooled under N$_2$-atmosphere to 0° C. and a solution of ethyl (all-Z)-2-hydroxy-9,12,15-octadecatrienoate (61) (119.7 mg, 0.37 mmol) in DMF, 2 mL, was added drop wise. The mixture was stirred for 30 minutes at 0° C. before EtI (0.15 mL, 1.87 mmol) was added. The mixture was then allowed to slowly reach room temperature and stirred over night. The reaction was quenched with NH$_4$Cl sat., 20 mL, and extracted with diethyl ether, 50 mL×2. The organic phase was washed with brine, 20 mL, dried (Na$_2$SO$_4$), filtered and evaporated in vacuo and subjected to flash chromatography on silica gel eluting with heptane:EtOAc (100:1)-(95:5) yielding 31.5 mg (24%) of the product 5 as a colorless liquid.

$^1$H NMR (200 MHz, CDCl$_3$) δ 0.95 (t, J=7.5 Hz, 3H), 1.20 (t, J=7.0 Hz, 3H), 1.22-1.30 (m, 11H), 1.63-1.71 (m, 2H), 1.98-2.12 (m, 4H), 2.78 (t, J=5.5 Hz, 4H), 3.33-3.45 (m, 1H), 3.52-3.64 (m, 1H), 3.78 (t, J=6.4 Hz, 1H), 4.12-4.24 (m, 2H), 5.27-5.40 (m, 6H)

$^{13}$C NMR (50 MHz, CDCl$_3$) δ 14.2, 15.1, 20.5, 25.2, 25.5, 25.6, 27.2, 29.0, 29.1, 29.2, 29.5, 33.0, 60.6, 65.9, 79.0, 127.1, 127.7, 128.2 (2 signals), 130.2, 131.9, 173.3

MS (electrospray); 373 [M+Na]$^+$

Ethyl (all-Z)-2-phtalimide-9,12,15-octadecatrienoate (62)

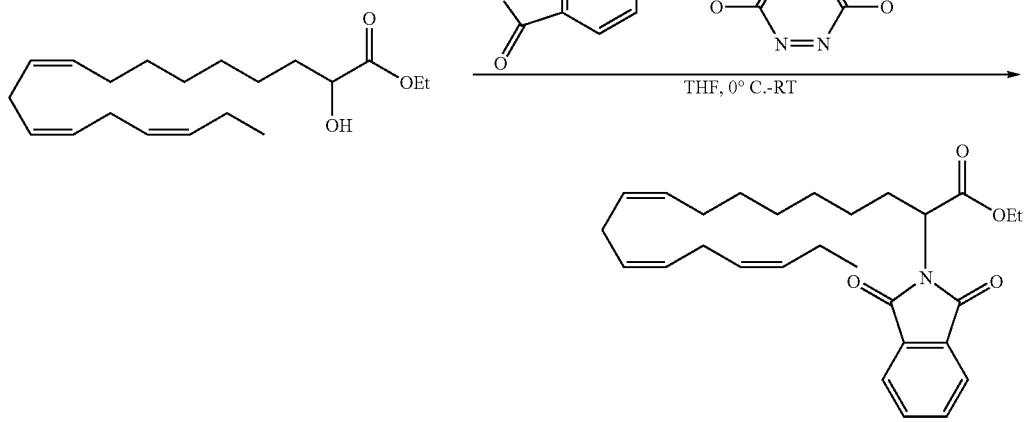

A solution of ethyl (all-Z)-2-hydroxy-9,12,15-octadecatrienoate (61) (176.8 mg, 0.548 mmol), phtalimide (97.6 mg, 0.663 mmol) and triphenylphosphine (178.3 mg, 0.680 mmol) in THF was cooled to 0° C. under N$_2$-atmosphere before addition of diisopropyl azodicarboxylate (DIAD) (128 µL, 0.660 mmol). The ice bath was removed and the mixture was stirred for 22 hrs. The mixture was evaporated in vacuo and subjected to flash chromatography on silica gel eluting with heptane:EtOAc (95:5)-(4:1) yielding 153.8 mg (62%) of ethyl (all-Z)-2-phtalimide-9,12,15-octadecatrienoate (62) as a colorless liquid.

$^1$H NMR (200 MHz, CDCl$_3$) δ 0.92 (t, J=7.5 Hz, 3H), 1.18 (t, J=7.1 Hz, 3H), 1.29 (m, 8H), 1.97-2.10 (m, 4H), 2.17-2.24 (m, 2H), 2.72-2.79 (m, 4H), 4.17 (q, J=7.1 Hz, 2H), 4.79 (dd, J=9.6, 6.0 Hz, 1H), 5.24-5.35 (m, 6H), 7.68-7.74 (m, 2H), 7.79-7.85 (m, 2H)

$^{13}$C NMR (50 MHz, CDCl$_3$) δ 14.0, 14.2, 20.4, 25.4, 25.5, 26.2, 27.0, 28.5, 28.8, 28.9, 29.4, 52.3, 61.6, 123.4, 127.0, 127.6, 128.11, 128.16, 130.1, 131.7, 131.8, 134.0, 167.6, 169.3

MS (electrospray); 474 [M+Na]$^+$

Ethyl (all-Z)-2-amino-9,12,15-octadecatrienoate (12)

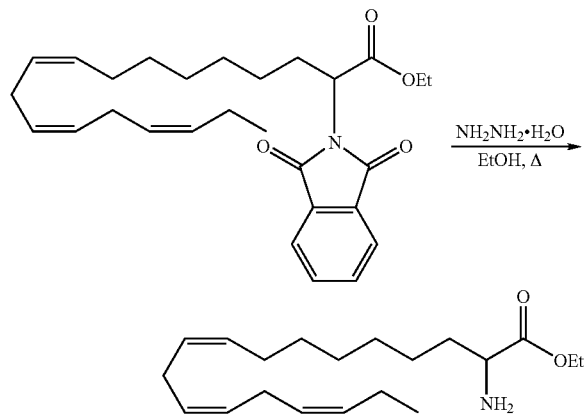

A solution of ethyl (all-Z)-2-phtalimide-9,12,15-octadecatrienoate (62) (104.6 mg, 0.232 mmol) in EtOH, 4 mL, was added hydrazine hydrate (17 µL, 0.35 mmol) and the mixture was refluxed under $N_2$-atmosphere for 15 hrs. The reaction mixture was cooled, evaporated in vacuo and subjected to flash chromatography on silica gel eluting with $CH_2Cl_2$:2M $NH_3$ in MeOH (97.5:2.5) to yield 58.4 mg (78%) of ethyl (all-Z)-2-amino-9,12,15-octadecatrienoate (12) as a colorless liquid.

$^1$H NMR (200 MHz, CDCl$_3$) δ 0.92 (t, J=7.5 Hz, 3H), 1.21 (t, J=7.1 Hz, 3H), 1.27 (m, 8H), 1.37-1.69 (m, 4H), 1.95-2.09 (m, 4H), 2.74 (t, J=5.6 Hz, 4H), 3.36 (bs, 1H), 4.11 (q, J=7.1 Hz, 2H), 5.22-5-37 (m, 6H)

$^{13}$C NMR (50 MHz, CDCl$_3$) δ 14.1 (2 C), 20.4, 25.4, 25.45, 25.49, 27.1, 29.0, 29.2, 29.4, 34.8, 54.3, 60.6, 127.0, 127.6, 128.11, 128.15, 130.1, 131.8, 176.1

MS (electrospray); 322 [M+H]$^+$, 344 [M+Na]$^+$

Ethyl (all-Z)-2-diethylamino-9,12,15-octadecatrienoate (10) and Ethyl (all-Z)-2-ethylamino-9,12,15-octadecatrienoate (11)

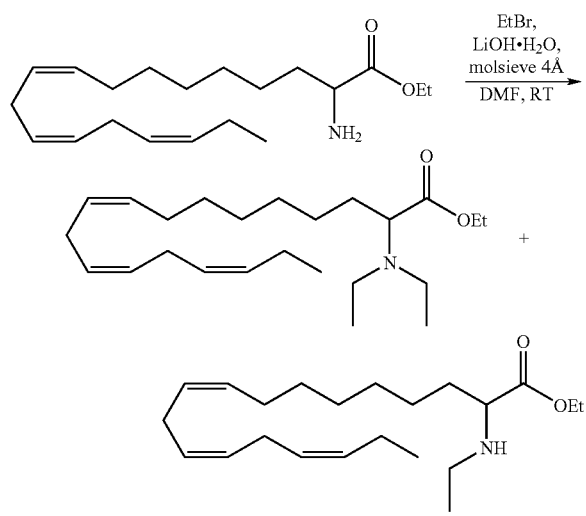

A mixture of ethyl (all-Z)-2-amino-9,12,15-octadecatrienoate (12) (551.7 mg, 1.72 mmol), LiOH.H$_2$O (144.6 mg, 3.45 mmol) and molsieve 4 Å (507 mg) in DMF, 4 mL, was added ethylbromide (2.6 mL, 34.8 mmol) and the resulting mixture was stirred at ambient temperature for 46 hrs. The mixture was diluted with diethyl ether, 100 mL, and filtered. The organic phase was washed with 1 M NaOH, 20 mL, and brine, 20 mL, dried (Na$_2$SO$_4$), filtered and evaporated in vacuo and subjected to flash chromatography on silica gel eluting with heptane:EtOAc (95:5)-CH$_2$Cl$_2$:2M NH$_3$ in MeOH (98:2) to yield 357 mg (55%) of the diethylamino ester 10 as a colorless liquid and 161 mg (27%) of the ethylamino ester 11 as a yellow liquid.

Ethyl (all-Z)-2-diethylamino-9,12,15-octadecatrienoate (10)

$^1$H NMR (200 MHz, CDCl$_3$) δ 0.93 (t, J=7.5 Hz, 3H), 0.99 (t, J=7.1 Hz, 6H), 1.22 (t, J=7.1 Hz, 3H), 1.27 (m, 8H), 1.51-1.70 (m, 2H), 1.96-2.11 (m, 4H), 2.43 (sextet, J=6.8 Hz, 2H), 2.66 (q, J=7.3 Hz, 2H), 2.71-2.79 (m, 4H), 3.28 (t, J=7.4 Hz, 1H), 4.10 (q, J=7.1 Hz, 2H), 5.22-5.38 (m, 6H)

$^{13}$C NMR (50 MHz, CDCl$_3$) δ 13.9, 14.2, 14.4, 20.5, 25.4, 25.5, 26.3, 27.1, 29.1, 29.3, 29.5, 29.9, 44.4, 59.7, 63.0, 127.0, 127.6, 128.2 (2C), 130.2, 131.8, 173.5

MS (electrospray); 378 [M+H]$^+$, 400 [M+Na]$^+$

Ethyl (all-Z)-2-ethylamino-9,12,15-octadecatrienoate (11)

$^1$HNMR (200 MHz, CDCl$_3$) δ0.91 (t, J=7.5 Hz, 3H), 1.02 (t, J=7.1 Hz, 3H), 1.24 (m, 11H), 1.55 (m, 3H), 1.94-2.08 (m, 4H), 2.35-2.65 (m, 2H), 2.73 (t, J=5.6 Hz, 4H), 3.14 (t, J=6.6 Hz, 1H), 4.11 (q, J=7.1 Hz, 2H), 5.17-5.38 (m, 6H)

$^{13}$C NMR (50 MHz, CDCl$_3$) δ 14.1, 14.2, 15.2, 20.4, 25.4, 25.5, 25.6, 27.0, 28.9, 29.2, 29.4, 33.5, 42.3, 60.3, 61.3, 127.0, 127.6, 128.09, 128.11, 130.1, 131.8, 175.5

MS (electrospray); 350 [M+H]$^+$, 372 [M+Na]$^+$

(all-Z)-4,7,10,13,16,19-docosahexaenol (63)

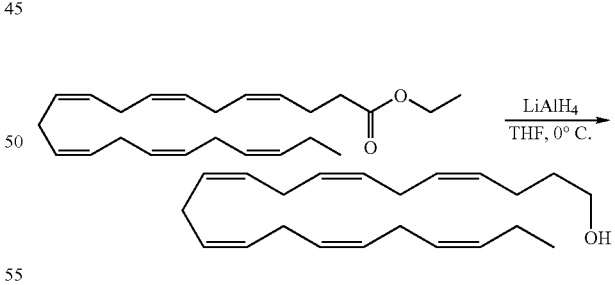

A solution of ethyl (all-Z)-4,7,10,13,16,19-docosahexaenoate (10.72 g, 30.0 mmol) in THF, 30 mL, was added drop wise to a suspension of LiAlH$_4$ in THH, 140 mL, under N$_2$-atmosphere at 0° C. The resulting mixture was stirred at 0° C. for 50 minutes, before it was quenched with water, 50 mL, added 1M HCl, 100 mL, and stirred at room temperature for 1 hr. The phases were separated and the water phase was extracted with diethyl ether, 100 mL×2. The organic phase was washed with 1M HCl, 50 mL, dried (Na$_2$SO$_4$), filtered and evaporated in vacuo yielding 8.56 g (91%) of (all-Z)-4,7,10,13,16,19-docosahexaenol (63) as a colorless liquid.

¹H NMR (200 MHz, CDCl₃) δ 1.00 (t, J=7.5 Hz, 3H), 1.63-1.73 (m, 2H), 1.83 (bs, 1H), 2.04-2.24 (m, 4H), 2.88 (bs, 10H), 3.67 (t, J=6.4 Hz, 2H), 5.41 (bs, 12H)

(all-Z)-4,7,10,13,16,19-docosahexaen-tosylate (64)

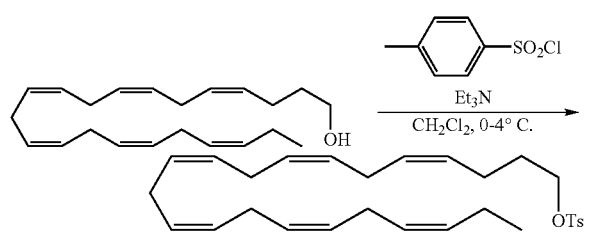

A solution of (all-Z)-4,7,10,13,16,19-docosahexaenol (63) (8.50 g, 27.0 mmol) and tosyl chloride (5.41 g, 28.4 mmol) in dry CH₂Cl₂, 30 mL, was cooled to 0° C. before addition of Et₃N (4.15 mL, 29.8 mmol). The reaction mixture was placed in the refrigerator. After 17 hrs an additional amount of tosyl chloride (774 mg, 4.06 mmol) and Et₃N (565 μL, 4.06 mmol) was added and the mixture was placed in the refrigerator for 2½ hrs. The reaction mixture was poured in ice-water and extracted with CH₂Cl₂, 50 mL×2, and evaporated in vacuo. The residue was dissolved in heptane, 100 mL, washed with water, 30 mL, 1M HCl, 30 mL×2, and brine, 30 mL, dried (Na₂SO₄), filtered and evaporated in vacuo. The residue was added pyridine, 1.6 mL, and water, 1.25 mL, and stirred at room temperature for 1 hr. The mixture was diluted with heptane, 100 mL, and washed with water, 25 mL, 1 M HCl, 25 mL×2, brine, 25 mL, dried (Na₂SO₄), filtered and evaporated in vacuo yielding 10.27 g (81%) of the tosylate 64 as a colorless oil.

¹H NMR (200 MHz, CDCl₃) δ 0.94 (t, J=7.5 Hz, 3H), 1.61-1.75 (m, 2H), 1.97-2.12 (m, 4H), 2.41 (s, 3H), 2.70-2.89 (m, 10H), 4.00 (t, J=6.4 Hz, 2H), 5.27-5.38 (m, 12H). 7.31 (d, 2H), 7.76 (d, 2H)

MS (electrospray); 491 [M+Na]⁺

(all-Z)-9,12,15-octadecatrienol (66)

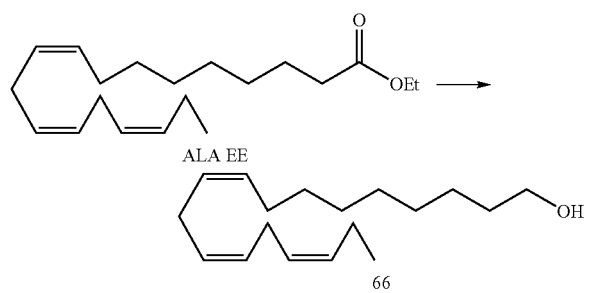

To a stirred suspension of LAH (0.130 g, 3.43 mmol) in dry THF (10 mL) held at 0° C. under inert atmosphere was added a solution of ethyl (all-Z)-9,12,15-octadecatrienoate (1.0 g, 3.26 mmol) in dry THF (15 mL) dropwise. The resulting solution was stirred at 0° C. for one hour, added 10% NH₄Cl (15 mL) and filtrated through a short pad of celite. The celite was washed with water (10 mL) and heptane (20 ml) and the layers were separated. The aqueous layer was extracted with heptane (20 mL) and the combined organic layer was washed with brine (20 mL) and dried (MgSO₄). This afforded 0.78 g (91%) of (all-Z)-9,12,15-octadecatrienol (66) as a colorless oil.

¹H-NMR (200 MHz, CDCl₃): δ 0.95 (t, 3H), 1.20-1.35 (m, 10H), 1.48-1.58 (m, 2H), 1.98-2.09 (m, 4H), 2.76-2.82 (m, 4H), 5.23-5.44 (m, 6H);

MS (electrospray): 287.3 [M+Na].

(all-Z)-9,12,15-octadecatrien-tosylate (67)

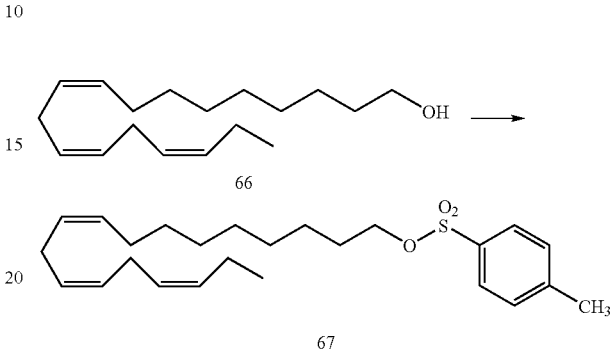

To a stirred solution of (all-Z)-9,12,15-octadecatrienol (66) (0.78 g, 2.95 mmol) in dry CH₂Cl₂ (15 mL) held at 0° C. under inert atmosphere was added toluene-4-sulfonyl chloride (1.12 g, 5.90 mmol) and Et₃N (0.82 mL, 5.90 mmol). The resulting solution was stirred at 0° C. for five hours and then 66 hours at ambient temperature. The mixture was poured into ice/water (40 mL) and the layers were separated. The aqueous layer was extracted with CH₂Cl₂ (20 mL) and the combined organic layer was concentrated. The crude product was added 2 mL pyridine and 1.6 mL water and the mixture was stirred at ambient temperature for 30 minutes. Heptane (70 mL) was added and the organic layer was washed with water (30 mL), 1M HCl (30 mL) and brine (30 mL). Drying (MgSO₄) and concentration under reduced pressure afforded 0.68 g (55%) of the tosylate 67 as a colorless oil.

¹H-NMR (200 MHz, CDCl₃): δ 0.91 (t, 3H), 1.15-1.35 (m, 10H), 1.53-1.60 (m, 2H), 1.98-2.12 (m, 4H), 2.43 (s, 3H), 2.70-2.80 (m, 4H), 5.22-5.40 (m, 6H), 7.31 (d, 2H), 7.76 (d, 2H);

MS (electrospray): 441.2 [M+Na].

Ethyl (all-Z)-2-ethyl, 2-ethoxycarbonyl-11,14,17-eicosatrienoate (23)

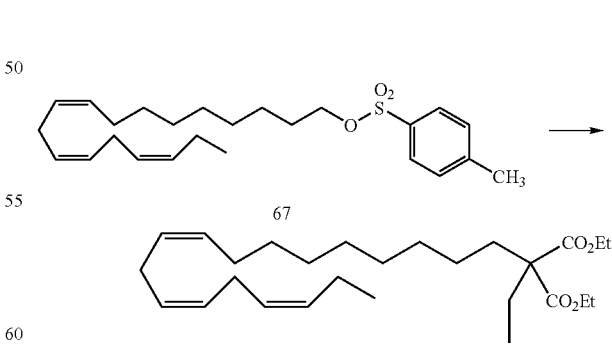

A stirred suspension of NaH (60%, 0.098 g, 2.44 mmol) in dry THF (15 mL) and dry DMF (3 mL) held at 0° C. under inert atmosphere was added diethyl ethylmalonate (0.61 mL, 3.25 mmol) dropwise. The resulting mixture was stirred at 0°

C. for ten minutes, given ambient temperature and stirred for another 20 minutes. The tosylate 67 (0.68 g, 1.62 mmol) in dry THF (3 mL) was added, followed by NaI (0.098 g, 0.65 mmol). The resulting solution was then stirred at 70° C. for four hours, cooled and portioned between 10% NH$_4$Cl (30 mL) and heptane (30 mL). The aqueous layer was extracted with heptane (20 mL) and the combined organic layer was washed with brine (30 mL) and dried (Na$_2$SO$_4$). This afforded 0.70 g (quant. yield) of the title compound 23 as colorless oil.

$^1$H-NMR (200 MHz, CDCl$_3$): δ 0.91 (t, 3H), 1.18-1.30 (m, 19H), 1.80-2.10 (m, 10H), 2.75-2.81 (m, 4H), 4.16 (m, 4H), 5.28-5.38 (m, 6H);

MS (electrospray): 457.3 [M+Na].

(all-Z)-2-ethyl, 2-carboxy-11,14,17-eicosatrienoic acid (24)

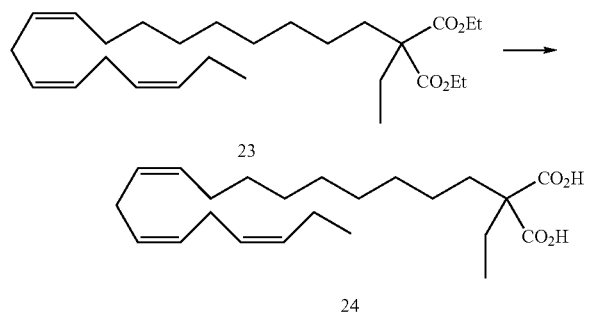

Ethyl (all-Z)-2-ethyl, 2-ethoxycarbonyl-11,14,17-eicosatrienoate (23) (0.70 g, 1.61 mmol) was dissolved in 96% ethanol (20 mL) and added 5M KOH (2.6 mL, 13 mmol). The resulting mixture was stirred at reflux for 19 hours, cooled and concentrated under reduced pressure. The resulting crude product was added 1M HCl (20 mL) and extracted twice with diethyl ether (30 mL). The combined organic layer was washed with brine (30 mL) and dried (MgSO$_4$). Concentration under reduced pressure afforded 0.60 g (quant. yield) of the title compound 24 as a pale brown oil.

MS (electrospray): 377.2 [M−H].

(all-Z)-2-ethyl-11,14,17-eicosatrienoic acid (68)

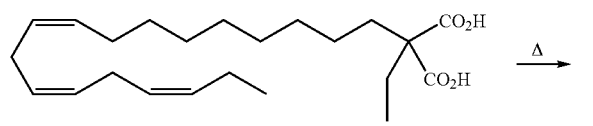

Neat (all-Z)-2-ethyl, 2-carboxy-11,14,17-eicosatrienoic acid (24) (0.60 g, 1.59 mmol) under inert atmosphere was given 160° C. for two hours, cooled and purified by flash chromatography (heptane:EtOAc 9:1 then 4:1). This afforded 0.33 g (62%) of the title (all-Z)-2-ethyl-11,14,17-eicosatrienoic acid (68) as a colourless oil.

$^1$H-NMR (200 MHz, CDCl$_3$): δ 0.84-0.99 (m, 8H), 1.15-1.35 (m, 101H), 1.35-1.70 (m, 4H), 2.00-2.15 (m, 4H), 2.20-2.30 (m, 1H), 2.75-2.85 (m, 4H), 5.25-5.45 (m, 6H);

MS (electrospray): 333.2 [M−H].

Ethyl (all-Z)-2-ethyl-11,14,17-eicosatrienoate (28)

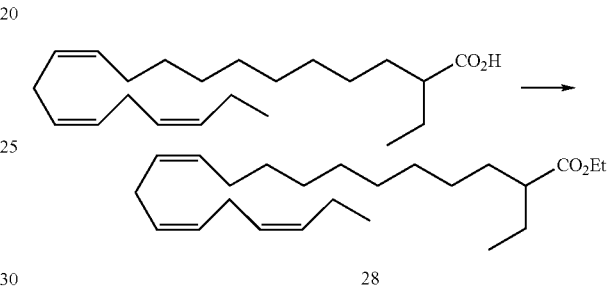

(all-Z)-2-ethyl-11,14,17-eicosatrienoic acid (0.15 g, 0.45 mmol) was dissolved in abs EtOH (5 mL), added a drop of concentrated H$_2$SO$_4$ and stirred at reflux under inert atmosphere for 18 hours. The mixture was cooled, concentrated and purified by flash chromatography (heptane:EtOAc 95:5). This afforded 0.13 g (80%) of the title compound 28 as a colorless oil.

$^1$H-NMR (200 MHz, CDCl$_3$): δ 0.85 (t, 3H), 0.94 (t, 3H), 1.18-1.34 (m, 13H), 1.45-1.59 (m, 4H), 1.97-2.08 (m, 4H), 2.25 (m, 1H), 2.74-2.85 (m, 4H), 4.09 (q, 4H), 5.24-5.42 (m, 6H);

$^{13}$C-NMR (50 MHz, CDCl$_3$): δ 11.76, 14.21, 14.30, 20.49, 25.46, 25.56, 27.18, 27.37, 29.22, 29.41, 29.42, 29.50, 29.59, 32.06, 47.29, 59.83, 127.06, 127.59, 128.18, 128.21, 130.27, 131.85, 176.33;

MS (electrospray): 385.3 [M+Na]$^+$.

2-((all-Z)-2-ethyl-5,8,11,14,17-eicosapentaenoyl)-sn-glycerol (71)

Step 1: Glycidyl (all-Z)-2-ethyl-5,8,11,14,17-eicosapentaenoate

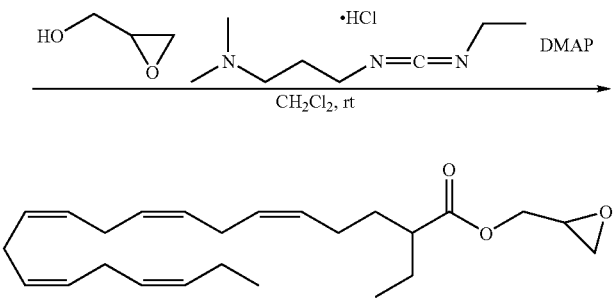

A solution of (all-Z)-2-ethyl-5,8,11,14,17-eicosapentaenoic acid (1.00 g, 3.03 mmol), glycidol (167 μl, 2.52 mmol), N-ethyl-N'-(3-dimethylaminopropyl)carbodiimide hydrochloride (585 mg, 3.05 mmol) and DMAP (372 mg, 3.05 mmol) in dry $CH_2Cl_2$ (10 ml) was stirred for 18 hrs under $N_2$-atmosphere at room temperature. The mixture was evaporated in vacuo. The residue was purified by flash chromatography on silica gel eluting with heptane-heptane:EtOAc (95: 5) yielded 647 mg (55%) of the title product as a slightly yellow liquid.

$^1$H NMR (200 MHz, $CDCl_3$) δ 0.85-0.99 (m, 6H), 1.42-1.80 (m, 5H), 2.03-2.09 (m, 4H), 2.28-2.42 (m, 1H), 2.60-2.64 (m, 1H), 2.79-2.82 (m, 8H), 3.14-3.21 (m, 1H), 3.88-3.97 (m, 1H), 4.36-4.46 (m, 1H), 5.23-5.51 (m, 10H)

MS (electrospray); 409 [M+Na]$^+$

Step 2: 1,3-di(trifluoroacetate)-2-((all-Z)-2-ethyl-5,8,11,14,17-eicosapentaenoyl)-sn-glycerol

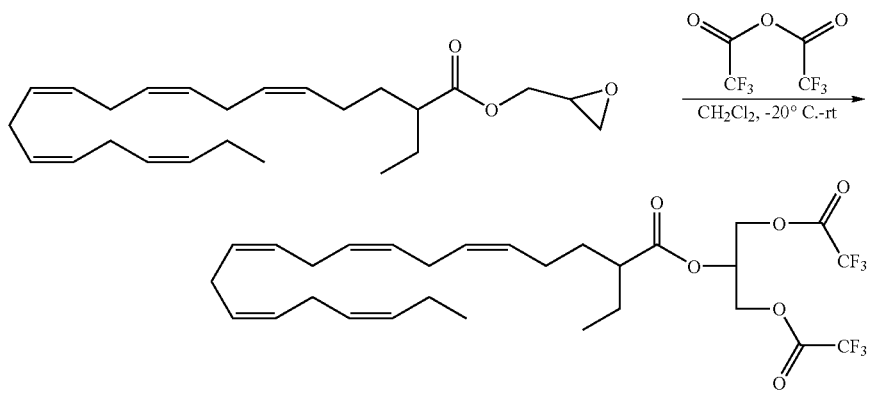

A solution of glycidyl (all-Z)-2-ethyl-5,8,11,14,17-eicosapentaenoate (641 mg, 1.66 mmol) in dry, alcohol-free $CH_2Cl_2$ (6.5 ml) was cooled to −20° C. under $N_2$-atmosphere. A solution of trifluoroacetic acid anhydride (TFAA) (0.93 ml, 6.69 mmol) in dry $CH_2Cl_2$ (6.5 ml) was added portion wise. The cooling bath was removed and the mixture was stirred for 70 minutes. The solvent and unreacted TFAA was evaporated in vacuo (t<40° C.) and the residue was dissolved in toluene (15 ml) and passed through a silica gel pad (16.5 g) eluting with toluene (350 ml). This yielded 607 mg (61%) of the crude title product as a yellow oil.

$^1$H NMR (200 MHz, $CDCl_3$) δ 0.83-0.99 (m, 6H), 1.54-1.67 (m, 4H), 1.99-2.13 (m, 4H), 2.27-2.38 (m, 1H), 2.63-2.82 (m, 8H), 4.44 (dd, J=11.8 Hz, 5.7 Hz, 2H), 4.62 (dd, J=11.9 Hz, 4.1 Hz, 2H), 5.20-5.45 (m, 11H)

Step 3: 2-((all-Z)-2-ethyl-5,8,11,14,17-eicosapentaenoyl)-sn-glycerol

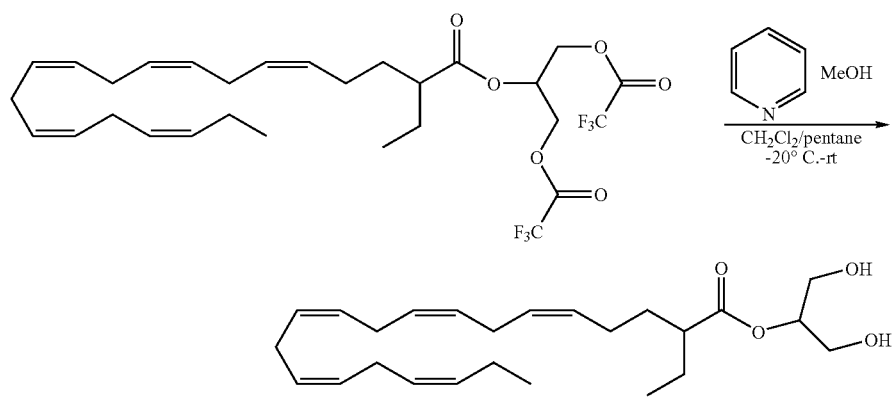

A solution of 1,3-di(trifluoroacetate)-2-((all-Z)-2-ethyl-5,8,11,14,17-eicosapentaenoyl)-sn-glycerol (607 mg, 1.02 mmol) in pentane/$CH_2Cl_2$ (2:1, 10 ml) was cooled to −20° C. under $N_2$-atmosphere. A solution of pyridine (0.83 ml, 10.3 mmol) and MeOH (0.62 ml, 15.3 mmol) in pentane/$CH_2Cl_2$ (2:1, 9 ml) was added drop wise. The cooling bath was removed and the mixture was stirred for 4 hrs. The resulting mixture was evaporated in vacuo. Flash chromatography on silica gel eluting with heptane-heptane:EtOAc 1:1 yielded 352 mg (86%) of the title product as a slightly yellow oil.

$^1$H NMR (200 MHz, $CDCl_3$) δ 0.86-0.99 (m, 6H), 1.43-1.81 (m, 4H); 1.94 (bs, 2H), 2.02-2.13 (m, 4H), 2.29-2.43 (m, 1H), 2.79-2.83 (m, 8H), 3.81 (d, J=4.8 Hz, 4H), 4.89-4.98 (m, 1H), 5.22-5.43 (m, 10H)

MS (electrospray); 427 [M+Na]$^+$

1,2,3-tris((all-Z)-2-ethyl-5,8,11,14,17-eicosapentaenoyl)-sn-glycerol (72)

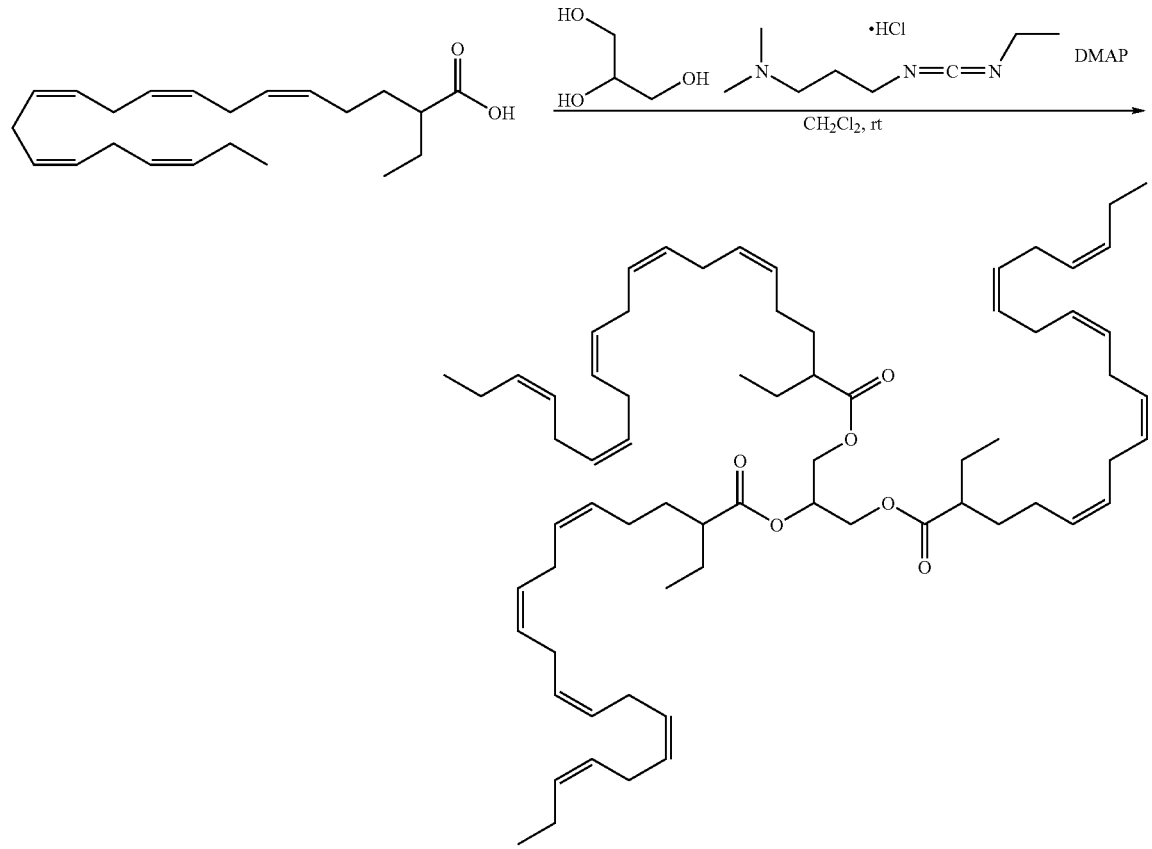

(all-Z)-2-ethyl-5,8,11,14,17-eicosapentaenoic acid (501 mg, 1.52 mmol), DMAP (185 mg, 1.52 mmol), N-ethyl-N′-(3-dimethylamino-propyl)carbodiimide hydrochloride (295 mg, 1.54 mmol) and dry $CH_2Cl_2$ (5 ml) were added to a solution of glycerol (31.6 mg, 0.343 mmol) in DMF (2 ml). The resulting mixture was stirred for 17½ hrs under $N_2$-atmosphere at room temperature. Diethyl ether (50 ml) was added and the resulting mixture was washed with 1M HCl (20 ml) and brine (20 ml), dried ($Na_2SO_4$) and evaporated in vacuo. Repeated flash chromatography on silica gel eluting with heptane-heptane:EtOAc (100:1)-(95:5) yielded 206 mg (58%) of the title product as a colorless oil.

$^1$H NMR (200 MHz, $CDCl_3$) δ 0.83-0.99 (m, 18H), 1.43-1.77 (m, 12H), 1.98-2.13 (m, 12H), 2.23-2.37 (m, 3H), 2.77-2.85 (m, 24H), 4.04-4.18 (m, 2H), 4.28-4.42 (m, 2H), 5.23-5.49 (m, 31H)

MS (electrospray); 1051 [M+Na]$^+$

The compounds listed in tables 1-3 can be obtained similarly to the above described examples:

TABLE 1

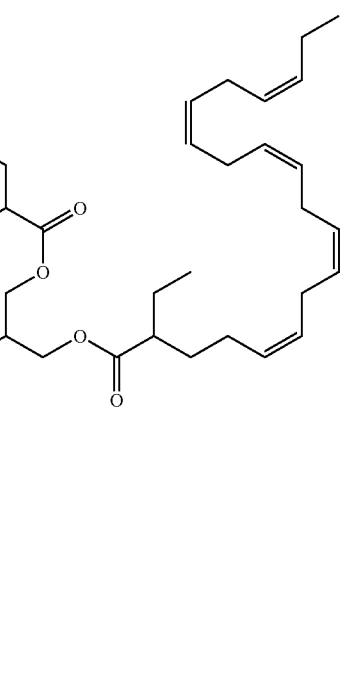

| Example | R1 | R2 | X | Methods |
|---|---|---|---|---|
| | $CH_3$ | H | * | I or III |
| | $CH_2CH_3$ | H | * | I or III |

TABLE 1-continued

| Example | R1 | R2 | X | Methods |
|---|---|---|---|---|
| | $CH_3$ | $CH_3$ | * | I or (III and |
| | $CH_2CH_3$ | $CH_2CH_3$ | * | I or (III and |

TABLE 1-continued

![structure with R1, R2, X]

| Example | R1 | R2 | X | Methods |
|---|---|---|---|---|
| | CH₃ | CH₂CH₃ | * | I or (III and |
| | CH₂CH₂CH₃ | H | * | I or III |
| | OCH₃ | H | * | II |
| | OCH₂CH₃ | H | * | II |
| | OCH₂CH₂CH₃ | H | * | II |
| | SCH₃ | H | * | I or II |
| | SCH₂CH₃ | H | * | I or II |
| | SCH₂CH₂CH₃ | H | * | I or II |
| | NHCH₃ | H | * | II |
| | NHCH₂CH₃ | H | * | II |
| | N(CH₃)₂ | H | * | II |
| | N(CH₂CH₃)₂ | H | * | II |
| | OH | H | * | II |

The possibility when R₁ and R₂ are inverse is also included. * wherein X represents a carboxylic acid or a derivative thereof, a carboxylate, a carboxylic anhydride or a carboxamide.

TABLE 2

![structure with R1, R2, X]

| Example | R1 | R2 | X | Methods |
|---|---|---|---|---|
| | CH₃ | H | ** | I or III |
| | CH₂CH₃ | H | ** | I or III |
| | CH₃ | CH₃ | ** | I or III |
| | CH₂CH₃ | CH₂CH₃ | * | I or (III and |
| | CH₃ | CH₂CH₃ | * | I or (III and |
| | CH₂CH₂CH₃ | H | ** | I or III |
| | OCH₃ | H | * | II or III |
| | OCH₂CH₃ | H | * | II or I |
| | OCH₂CH₂CH₃ | H | * | II or I |
| | SCH₃ | H | * | I or I |
| | SCH₂CH₃ | H | * | I or I |
| | SCH₂CH₂CH₃ | H | * | I or I |
| | NHCH₃ | H | * | II |
| | NHCH₂CH₃ | H | * | II |
| | N(CH₃)₂ | H | * | II |
| | N(CH₂CH₃)₂ | H | * | II |

The possibility when R₁ and R₂ are inverse is also included. * wherein X represents a carboxylic acid or a derivative thereof, a carboxylate, a carboxylic anhydride or a carboxamide. ** wherein X represents a carboxylic anhydride, a carboxamide, a mono- di or triglyceride, or a phospholipid.

TABLE 3

![structure with R1, R2, X]

| Example | R1 | R2 | X | Methods |
|---|---|---|---|---|
| | CH₃ | H | * | I |
| | CH₂CH₃ | H | * | I |
| | CH₃ | CH₃ | * | I |
| | CH₂CH₃ | CH₂CH₃ | * | I |
| | CH₃ | CH₂CH₃ | * | I |
| | CH₂CH₂CH₃ | H | * | I |
| | OCH₃ | H | * | II |
| | OCH₂CH₃ | H | * | II |

TABLE 3-continued

![structure with R1, R2, X]

| Example | R1 | R2 | X | Methods |
|---|---|---|---|---|
| | OCH₂CH₂CH₃ | H | * | II |
| | SCH₃ | H | * | I or II |
| | SCH₂CH₃ | H | * | I or II |
| | SCH₂CH₂CH₃ | H | * | I or II |
| | NHCH₃ | H | * | II |
| | NHCH₂CH₃ | H | * | II |
| | N(CH₃)₂ | H | * | II |
| | N(CH₂CH₃)₂ | H | * | II |
| | OH | H | * | II |

The possibility when R₁ and R₂ are inversely is also included. * wherein X represents a carboxylic acid or a derivative thereof, a carboxylate, a carboxylic anhydride or a carboxamide.

The invention shall no be limited to the shown embodiments and examples.

The invention claimed is:

1. An omega-3 lipid compound of formula (I):

(I)

wherein

R₁ and R₂ are the same or different and are chosen from hydrogen, an alkyl group, a halogen atom, an alkoxy group, an acyl group, an acyloxy group, an alkenyl group, an alkynyl group, an aryl group, an alkylthio group, a carboxy group, an alkylsulfinyl group, an alkylsulfonyl group, an amino group, and an alkylamino group;

X is chosen from a carboxylic acid, a salt thereof, or a derivative thereof, wherein the derivative is a phospholipid, triglyceride, diglyceride, or monoglyceride; an ethyl carboxylate; a carboxylic anhydride; and a carboxamide; and Y is chosen from a C₁₆ to C₂₂ alkene with two or more double bonds, having E and/or Z configuration;

with the provisos that:

R₁ and R₂ are not simultaneously hydrogen or fluorine; and the compound of formula (1) is not:
- a 2-substituted (all-Z)-4,7,10,13,16,19-docosahexaenoic acid in the form of a carboxylic acid, a carboxylate, a carboxylic anhydride or a carboxamide;
- α-methyl 4,7,10,13,16,19-docosahexaenoic acid, or its ethyl ester;
- α-methyl-5,8,11,14,17 eicosapentaenoic acid, or its ethyl ester;
- α-ethyl-5,8,11,14,17 eicosapentaenoic acid, or its ethyl ester;
- 2,2-dimethyl-5,8,11,14,17 eicosapentaenoic acid, or its ethyl ester;
- (all-Z)-2-benzyl-5,8,11,14,17 eicosapentaenoic acid, or its ethyl ester;
or
- (all-Z)-2-carboxy-6,9,12,15,18,21-tetracosahexaenoic acid.

2. The compound according to claim 1, wherein Y is chosen from a $C_{16}$-$C_{20}$ alkene with 2-6 double bonds in Z configuration.

3. The compound according to claim 2, wherein the 2-6 double bonds are methylene interrupted double bonds.

4. The compound according to claim 1, wherein Y is a $C_{16}$-$C_{20}$ alkene with 3-5 double bonds in Z configuration.

5. The compound according to claim 2, wherein the 2-6 double bonds are methylene interrupted double bonds.

6. The compound according to claim 1, wherein Y is a $C_{20}$ alkene with 5 double bonds in Z configuration.

7. The compound according to claim 1, wherein Y is a $C_{16}$ alkene with 3 double bonds in Z-configuration.

8. The compound according to claim 1, chosen from the following categories:

Category A-(all-Z)-9,12,15-octadecatrienoic acid (alpha-linolenic acid, ALA)

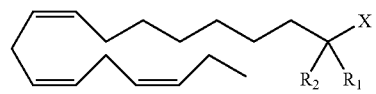

Y=$C_{16}$ alkene with 3 double bonds in Z-configuration in positions 9, 12, and 15;

Category B-(all-Z)-7,10,13,16,19-docosapentaenoic acid (clupanodonic acid, DPA)

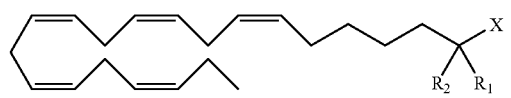

Y=$C_{20}$ alkene with 5 double bonds in Z-configuration in positions 7, 10, 13, 16, and 19;

Category C-(all-Z)-11,14,17-eicosatrienoic acid

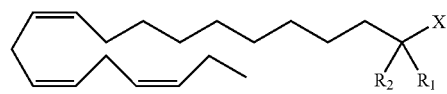

Y=$C_{18}$ alkene with 3 double bonds in Z-configuration in positions 11, 14, and 17;

Category D-(4E, 8Z, 11Z, 14Z, 17Z)-eicosapentaenoic acid

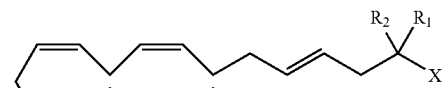

Y=$C_{18}$ alkene with 5 double bonds in positions 4, 8, 11, 14, and 17, where the double bonds in position 8, 11, 14, and 17 are in Z-configuration, and the double bond in position 4 is in E configuration;

Category E-(all-Z)-5,8,11,14,17-eicosapentaenoic acid (EPA)

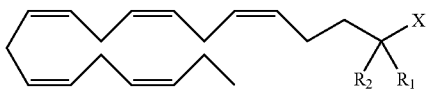

Y=$C_{18}$ alkene with 5 double bonds in Z-configuration in positions 5, 8, 11, 14, and 17; and Category F-(4E, 7Z, 10Z, 13Z, 16Z, 19Z)-docosahexaenoic acid (trans-DHA)

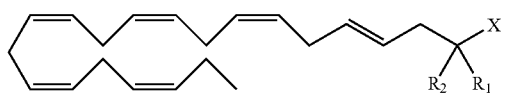

Y=$C_{20}$ alkene with 6 double bonds in positions 4, 7, 10, 13, 16, and 19, where the double bonds in position 7, 10, 13, 16, and 19 are in Z-configuration, and the double bond in position 4 is in E configuration.

9. The compound according to claim 1 in the form of a salt

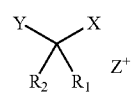

wherein X is $COO^-$, $Z^+$ is chosen from $Li^+$, $Na^+$, $K^+$, $NH_4^+$,

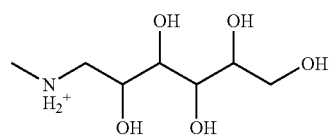

Meglumine,

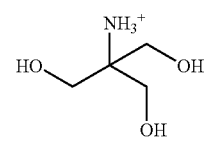

Tris(hydroxymethyl)aminomethane,

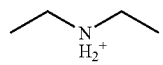

Diethylamine, and

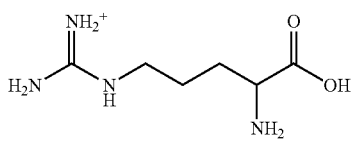 [SMILES: NC(=[NH2+])NCCCC(N)C(=O)O]

Arginine; or

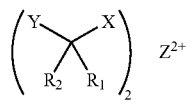

wherein X=COO⁻,
$Z^{2+}$ is chosen from $Mg^{2+}$, $Ca^{2+}$,

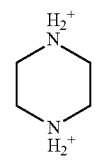

Ethylenediamine,
and

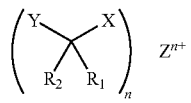

Piperazine; or

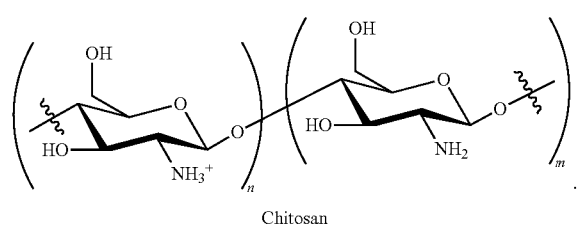

wherein X is COO⁻,
$Z^{n+}$ is

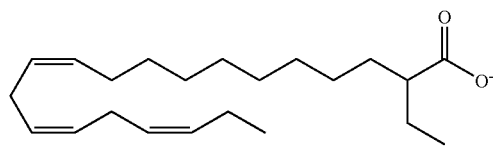

Chitosan

10. The compound according to claim 9, wherein the compound is chosen from:
(all-Z)-2-ethyl-11,14,17-eicosatrienoic acid meglumine salt

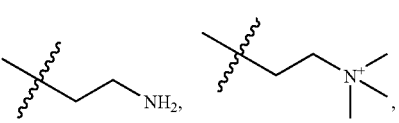

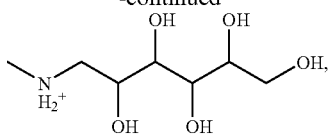

(all-Z)-2-ethyl-9,12,15-octadecatrienoic acid magnesium salt

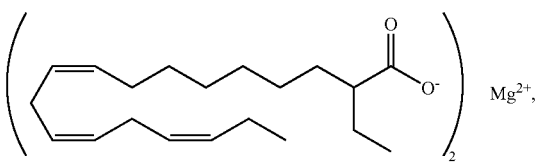

(all-Z)-2-ethyl-7,10,13,16,19-docosapentaenoic acid tris(hydroxymethy)aminomethane salt

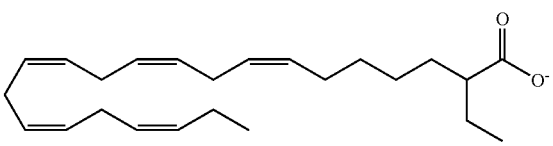

and
(all-Z)-2-ethyl-7,10,13,16,19-docosapentaenoic acid ammonium salt

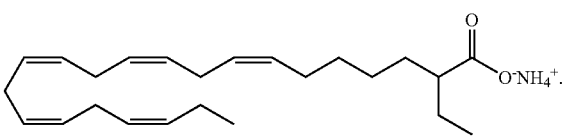

11. The compound according to claim 1, wherein X is a carboxylic acid in the form of a phospholipid, represented by formula (II)

(II)

wherein
Z is

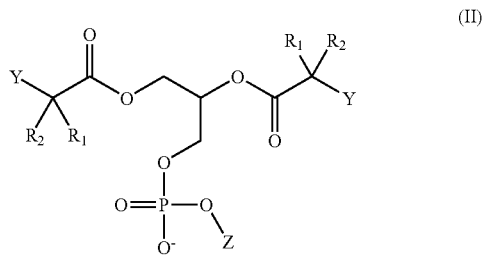

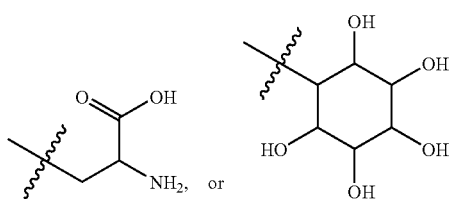

or represented by formula (III)

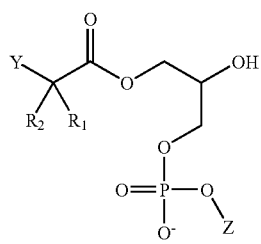

wherein
Z is

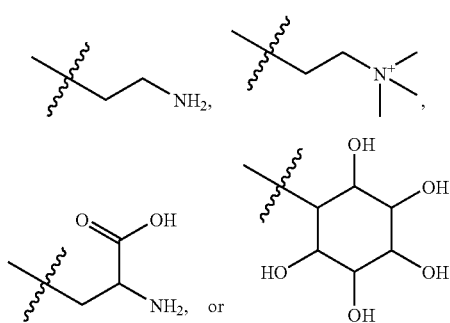

or represented by formula (IV)

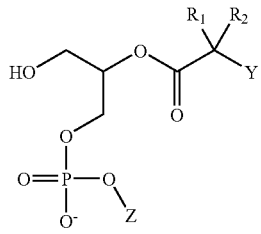

wherein
Z is

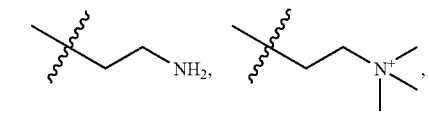

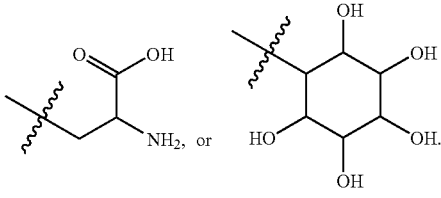

12. The compound according to claim 1, wherein X is a carboxylic acid in the form of a triglyceride, represented by formula (V)

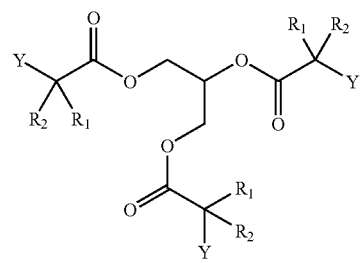

or,
wherein X is a carboxylic acid in the form of a 1-monoglyceride, represented by formula (VI)

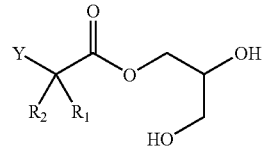

or,
wherein X is a carboxylic acid in the form of a 2-monoglyceride, represented by formula (VII)

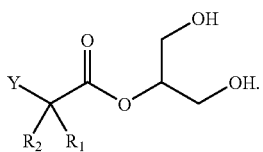

13. An omega-3 lipid compound derived from: from:
(all-Z)-6,9,12,15-octadecatetraenoic acid;
(all-Z)-6,9,12,15,18,21-tetracosahexaenoic acid;
(5E,8Z,11Z,14Z,17Z)-5,8,11,14,17-eicosapentaenoic acid; or
(all-Z)-8,11,14,17-eicosatetraenoic acid
in the form of a carboxylic acid, a salt thereof, or a derivative thereof, wherein the derivative is a phospholipid, triglyceride, diglyceride, or monoglyceride; an ethyl carboxylate; a carboxylic anhydride; or a carboxamide,
wherein the compound is substituted at carbon 2, counted from the functional group of the omega-3 lipid compound, with at least one substituent chosen from:

hydrogen, a hydroxy group, an alkyl group, a halogen atom, an alkoxy group, an acyl group, an acyloxy group, an alkenyl group, an alkynyl group, an aryl group, an alkylthio group, a carboxy group, an alkylsulfinyl group, an alkylsulfonyl group, an amino group, and an alkylamino group, with the provisos that the omega-3 lipid compound is not substituted with two hydrogen atoms or two fluorine atoms;
α-methyl-5,8,11,14,17 eicosapentaenoic acid, or its ethyl ester;
α-ethyl-5,8,11,14,17 eicosapentaenoic acid, or its ethyl ester;
2,2-dimethyl-5,8,11,14,17 eicosapentaenoic acid, or its ethyl ester;
(all-Z)-2-benzyl-5,8,11,14,17 eicosapentaenoic acid, or its ethyl ester; or
(all-Z)-2-carboxy-6,9,12,15,18,21-tetracosahexaenoic acid.

14. An omega-3 lipid compound, which is derived from (all-Z)-5,8,11,14,17-eicosapentaenoic acid (EPA), represented by the formula (VIII)

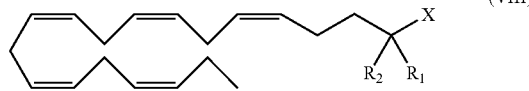
(VIII)

wherein X is chosen from a carboxylic acid, a salt thereof, or a derivative thereof, wherein the derivative is a phospholipid, triglyceride, diglyceride, or monoglyceride; an ethyl carboxylate; a carboxylic anhydride; and a carboxamide, wherein $R_1$ and $R_2$ are the same or different and are chosen from hydrogen, a hydroxy group, a $C_3$-$C_7$ alkyl group, a halogen atom, an alkoxy group, an acyloxy group, an acyl group, an alkenyl group, an alkynyl group, an alkylthio group, an alkoxycarbonyl group, a carboxy group, an alkylsulfinyl group, an alkylsulfonyl group, an amino group, and an alkylamino group, with the proviso that $R_1$ and $R_2$ are not simultaneously hydrogen, and the compound is not α-methyl-5,8,11,14,17 eicosapentaenoic acid, or its ethyl ester;
α-ethyl-5,8,11,14,17 eicosapentaenoic acid, or its ethyl ester; or
2,2-dimethyl-5,8,11,14,17 eicosaaentaenoic acid, or its ethyl ester.

15. The compound according to claim 14, wherein $R_1$ and $R_2$ are chosen from hydrogen, a $C_3$-$C_7$ alkyl group, a $C_1$-$C_7$ alkoxy group, a $C_1$-$C_7$ alkylthio group, an amino group, a $C_1$-$C_7$ alkylamino group, a $C_1$-$C_7$ alkoxycarbonyl group, and a carboxy group.

16. The compound according to claim 14, wherein the compound is chosen from:
1,2-Di((all-Z)-2-ethyl-5,8,11,14,17-eicosapentaenoyl)-sn-glycero-3-phosphocholine

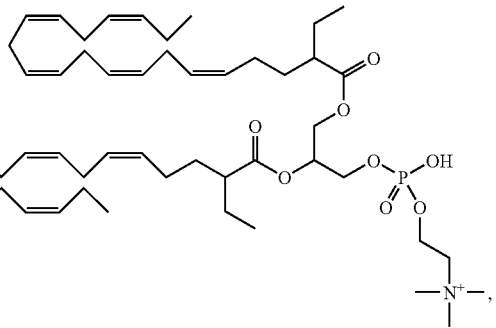

2-(all-Z)-2-ethyl-5,8,11,14,17-eicosapentaenoyl-sn-glycero-3-phosphoethanolamine

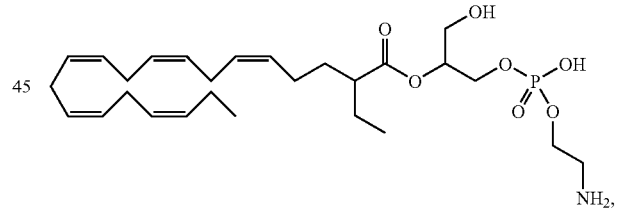

1,2,3-tris((all-Z)-2-ethyl-5,8,11,14,17-eicosapentaenoyl)-sn-glycerol

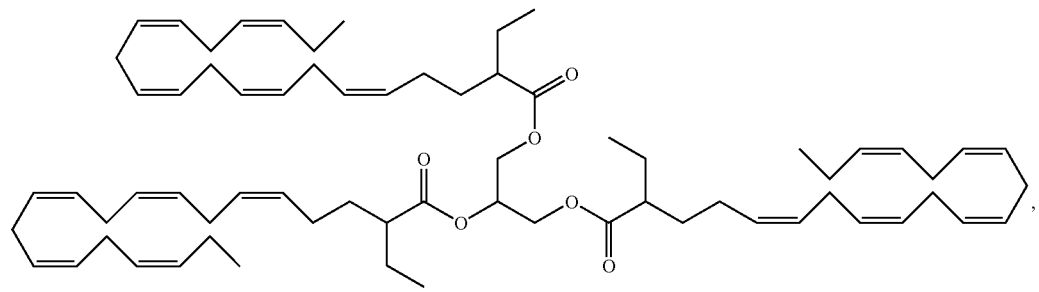 [SMILES: CC/C=C\C/C=C\C/C=C\C/C=C\C/C=C\CCC(CC)C(=O)OCC(COC(=O)C(CC)CC/C=C\C/C=C\C/C=C\C/C=C\C/C=C\CC)OC(=O)C(CC)CC/C=C\C/C=C\C/C=C\C/C=C\C/C=C\CC ; ","]

and
2-((all-Z)-2-ethyl-5,8,11,14,17-eicosapentaenoyl)-sn-glyceral

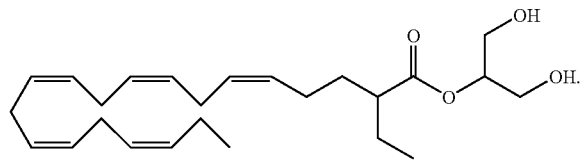 [SMILES: CC/C=C\C/C=C\C/C=C\C/C=C\C/C=C\CCC(CC)C(=O)OC(CO)CO]

17. The compound according to claim 1, wherein the alkyl group is chosen from methyl, ethyl, n-propyl, isopropyl, n-butyl, iso-butyl, sec-butyl, and n-hexyl.

18. The compound according to claim 17, wherein the alkyl group is chosen from n-propyl, isopropyl, n-butyl, iso-butyl, sec-butyl, n-and hexyl.

19. The compound according to claim 1, wherein the halogen atom is fluorine.

20. The compound according to claim 1, wherein the alkoxy group is chosen from methoxy, ethoxy, propoxy, isopropoxy, sec-butoxy, phenoxy, benzyloxy, $OCH_2CF_3$, and $OCH_2CH_2OCH_3$.

21. The compound according to claim 1, wherein the alkylthio group is chosen from methylthio, ethylthio, isopropylthio, and phenylthio.

22. The compound according to claim 1, wherein the carboxamide group is chosen from a primary carboxamide, N-methyl carboxamide, N,N-dimethyl carboxamide, N-ethyl carboxamide, and N,N-diethyl carboxamide.

23. The compound according to claim 1, wherein Y is a $C_{16}$ alkene with 3 methylene interrupted double bonds in Z configuration, one of $R_1$ and $R_2$ is methyl, ethyl, or propyl, and the other one is hydrogen.

24. The compound according to claim 1, wherein Y is a $C_{16}$ alkene with 3 methylene interrupted double bonds in Z configuration, one of $R_1$ and $R_2$ is methoxy, ethoxy, or propoxy, and the other one is hydrogen.

25. The compound according to claim 1, wherein is a $C_{16}$ alkene with 3 methylene interrupted double bonds in Z configuration, one of $R_1$ and $R_2$ is thiomethyl, thioethyl, or thiopropyl, and the other one is hydrogen.

26. The compound according to claim 1, wherein Y is a $C_{16}$ alkene with 3 methylene interrupted double bonds in Z configuration, one of $R_1$ and $R_2$ is ethylamino or diethylamino, and the other one is hydrogen.

27. The compound according to claim 1, wherein Y is a $C_{16}$ alkene with 3 methylene interrupted double bonds in Z configuration, one of $R_1$ and $R_2$ is amino and the other one is hydrogen.

28. The compound according to any one of the claims 23-27, wherein the double bonds are located in positions 9, 12, and 15 of the omega-3 lipid compound.

29. The compound according to claim 1, wherein Y is a $C_{20}$ alkene with 5 methylene interrupted double bonds in Z configuration, one of $R_1$ and $R_2$ is methyl, ethyl, or propyl, and the other one is hydrogen.

30. The compound according to claim 1, wherein Y is a $C_{20}$ alkene with 5 methylene interrupted double bonds in Z configuration, one of $R_1$ and $R_2$ is methoxy, ethoxy, or propoxy, and the other one is hydrogen.

31. The compound according to claim 1, wherein Y is a $C_{20}$ alkene with 5 methylene interrupted double bonds in Z configuration, one of $R_1$ and $R_2$ is thiomethyl, thioethyl, or thiopropyl, and the other one is hydrogen.

32. The compound according to any one of the claims 29-31, wherein the double bonds are located in positions 7, 10, 13, 16 and 19 of the omega-3 lipid compound.

33. The compound according to claim 1, wherein $R_1$ and $R_2$ are different.

34. The compound according to claim 33 in racemic form.

35. The compound according to claim 33 in the form of its R stereoisomer.

36. The compound according to claim 33 in the form of its S stereoisomer.

37. A pharmaceutical composition comprising a compound according to claim 1.

38. The pharmaceutical composition according to claim 37, further comprising a pharmaceutically acceptable carrier, an excipient, a diluent, or any combination thereof.

39. The pharmaceutical composition according to claim 37, formulated for oral administration.

40. The pharmaceutical composition according to claim 39 in the form of a capsule, a sachet, or a solid dosage form.

41. The pharmaceutical composition according to any one of the claim 37, formulated to provide a daily dosage of 1 mg to 10 g of the compound.

42. A pharmaceutical composition according to claim 37 for use as a medicament.

43. A lipid composition comprising an omega-3 lipid compound according to claim 1.

44. The lipid composition according to claim 43, wherein at least 60% by weight of the lipid composition is comprised of the compound.

45. The lipid composition according to claim 43, further comprising fatty acids chosen from (all-Z)-5,8,11,14,17-eicosapentaenoic acid (EPA), (all-Z)-4,7,10,13,16,19-docosahexaenoic acid (DHA), (all-Z)-6,9,12,15,18-heneicosapentaenoic acid (HPA), and/or (all-Z)-7,10,13,16,19-docosapentaenoic acid (DPA).

46. The lipid composition according to claim 45, wherein the fatty acids are present in their alpha substituted form.

47. The lipid composition according to claim 43, further comprising a pharmaceutically acceptable antioxidant.

48. The lipid composition according to claims 47, wherein the antioxidant is tocopherol.

49. The lipid composition according to claim 43 for use as a medicament.

50. A method for the treatment of peripheral insulin resistance and/or a diabetic condition elevated triglyceride levels, and/or non-HDL cholesterol, LDL cholesterol and VLDL cholesterol levels, a hyperlipidemic condition, obesity or an overweight condition, a fatty liver disease, or an inflammatory disease or condition comprising administering a compound according to claim 1.

51. A method for the reduction of plasma insulin, blood glucose and/or serum triglycerides, for increasing serum HDL levels in humans or for reduction of body weight comprising administering a compound according to claim 1.

* * * * *

UNITED STATES PATENT AND TRADEMARK OFFICE
CERTIFICATE OF CORRECTION

| | | |
|---|---|---|
| PATENT NO. | : 8,399,516 B2 | Page 1 of 1 |
| APPLICATION NO. | : 12/446615 | |
| DATED | : March 19, 2013 | |
| INVENTOR(S) | : Morten Bryhn et al. | |

It is certified that error appears in the above-identified patent and that said Letters Patent is hereby corrected as shown below:

In the Claims:

Claim 1, column 60, line 51, "formula (1)" should read -- formula (I) --.

Claim 9, column 63, line 19, "$Mg^{2+}$, $Ca^{24+}$" should read -- $Mg^{2+}$, $Ca^{2+}$ --.

Claim 16, column 68, line 20, "sn-glycero-3" should read -- sn-glycerol-3 --.

Claim 16, column 68, line 40, "sn-glycero-3" should read -- sn-glycerol-3 --.

Claim 16, column 69, line 3, "sn-glyceral" should read -- sn-glycerol --.

Claim 25, column 69, line 41, "wherein is a $C_{16}$" should read -- wherein Y is a $C_{16}$ --.

Claim 48, column 70, line 46, "according to claims 47" should read -- according to claim 47 --.

Signed and Sealed this
Twenty-eighth Day of May, 2013

Teresa Stanek Rea
*Acting Director of the United States Patent and Trademark Office*